(12) United States Patent
Kraft

(10) Patent No.: US 10,172,850 B2
(45) Date of Patent: *Jan. 8, 2019

(54) SUBSTITUTED DIKETOPIPERAZINE ANALOGS FOR USE AS DRUG DELIVERY AGENTS

(71) Applicant: MannKind Corporation, Valencia, CA (US)

(72) Inventor: Kelly Sullivan Kraft, Poughquag, NY (US)

(73) Assignee: MannKind Corporation, Westlake Village, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/488,915

(22) Filed: Apr. 17, 2017

(65) Prior Publication Data

US 2017/0216280 A1    Aug. 3, 2017

Related U.S. Application Data

(60) Continuation of application No. 14/945,168, filed on Nov. 18, 2015, now Pat. No. 9,655,850, which is a division of application No. 14/536,168, filed on Nov. 7, 2014, now Pat. No. 9,220,687, which is a continuation of application No. 13/649,430, filed on Oct. 11, 2012, now Pat. No. 8,906,926, which is a continuation of application No. 12/649,210, filed on Dec. 29, 2009, now Pat. No. 8,314,106.

(60) Provisional application No. 61/141,207, filed on Dec. 29, 2008.

(51) Int. Cl.
| | |
|---|---|
| *C07D 241/08* | (2006.01) |
| *A61K 31/495* | (2006.01) |
| *A61K 38/28* | (2006.01) |
| *A61K 38/26* | (2006.01) |
| *A61K 38/00* | (2006.01) |
| *A61K 9/00* | (2006.01) |
| *A61K 9/16* | (2006.01) |

(52) U.S. Cl.
CPC .......... *A61K 31/495* (2013.01); *A61K 9/0073* (2013.01); *A61K 9/1617* (2013.01); *A61K 9/1694* (2013.01); *A61K 38/26* (2013.01); *A61K 38/28* (2013.01); *C07D 241/08* (2013.01); *A61K 38/00* (2013.01); *A61K 2121/00* (2013.01)

(58) Field of Classification Search
CPC ...... A61K 38/28; A61K 38/26; A61K 31/495; A61K 9/0073; A61K 9/1617; A61K 9/1694; A61K 2121/00; C07D 241/08
See application file for complete search history.

(56) References Cited

U.S. PATENT DOCUMENTS

| | | |
|---|---|---|
| 2,549,303 A | 4/1951 | Friden |
| 2,754,276 A | 7/1956 | Joseph et al. |
| D189,076 S | 10/1960 | Altman |
| 3,337,740 A | 8/1967 | Gray et al. |
| 3,407,203 A | 10/1968 | Buijle |
| 3,518,340 A | 6/1970 | Raper |
| 3,622,053 A | 11/1971 | Ryden |
| 3,673,698 A | 7/1972 | Guerard |
| 3,669,113 A | 8/1972 | Altounyan et al. |
| 3,823,816 A | 7/1974 | Controullis et al. |
| 3,823,843 A | 7/1974 | Stephens et al. |
| 3,856,142 A | 12/1974 | Vessalo |
| 3,873,651 A | 3/1975 | Mosley, Jr. et al. |
| 3,906,950 A | 9/1975 | Cocozza |
| 3,921,637 A | 11/1975 | Bennie et al. |
| 3,976,773 A | 8/1976 | Curran et al. |
| 3,980,074 A | 9/1976 | Watt et al. |
| 3,998,226 A | 12/1976 | Harris |
| 4,013,075 A | 3/1977 | Cocozza |
| 4,018,619 A | 4/1977 | Webster et al. |
| 4,022,749 A | 5/1977 | Kuechler |
| 4,040,536 A | 8/1977 | Schwarz |
| 4,047,525 A | 9/1977 | Kulessa et al. |
| 4,066,756 A | 1/1978 | Orr et al. |
| 4,078,128 A | 3/1978 | Hoyt et al. |
| 4,091,077 A | 5/1978 | Smith et al. |
| 4,098,273 A | 7/1978 | Glenn |
| 4,102,953 A | 7/1978 | Johnson et al. |
| 4,110,240 A | 8/1978 | Leo et al. |
| 4,148,308 A | 4/1979 | Sayer |
| 4,153,689 A | 5/1979 | Hirai |
| D252,707 S | 8/1979 | Besnard |
| 4,168,002 A | 9/1979 | Crosby |
| 4,171,000 A | 10/1979 | Uhle |
| 4,175,556 A | 11/1979 | Freezer |
| 4,187,129 A | 2/1980 | Bost et al. |
| 4,196,196 A | 4/1980 | Tiholiz |
| 4,206,758 A | 6/1980 | Hallworth et al. |
| 4,210,140 A | 7/1980 | James et al. |
| 4,211,769 A | 7/1980 | Okada |

(Continued)

FOREIGN PATENT DOCUMENTS

| | | |
|---|---|---|
| CA | 2536047 A1 | 3/2005 |
| CA | 2551182 C | 8/2010 |

(Continued)

OTHER PUBLICATIONS

Cheatham et al. "Prandial Technosphere®/Insulin inhalation provides significantly better control of meal-related glucose excursions than prandial subcutaneous insulin." Presented at the Diabetes Technology Society meeting, Oct. 2004.

(Continued)

*Primary Examiner* — Erich A Leeser
(74) *Attorney, Agent, or Firm* — K&L Gates LLP; Louis C. Cullman; Hal Gibson

(57) ABSTRACT

Disclosed are drug delivery systems for the delivery of small molecule and macromolecular drugs. More particularly, disclosed are substituted analogs of 3,6-di(alkyl-4 aminobutyl)-2,5-diketopiperazine (which may also be referred to DKP), their use in the formulation of both small molecule and macromolecular drugs including therapeutic, prophylactic and diagnostic agents, stabilizing agents and systems for their delivery.

16 Claims, 7 Drawing Sheets

(56) References Cited

U.S. PATENT DOCUMENTS

| | | | |
|---|---|---|---|
| 4,268,460 A | 5/1981 | Boiarski et al. |
| 4,272,398 A | 6/1981 | Jaffe |
| 4,275,820 A | 6/1981 | LeBlond |
| 4,289,759 A | 9/1981 | Heavener |
| 4,294,829 A | 10/1981 | Suzuki |
| 4,300,546 A | 11/1981 | Kruber |
| 4,356,167 A | 10/1982 | Kelly |
| D269,463 S | 6/1983 | Young et al. |
| 4,407,525 A | 10/1983 | Hoppe |
| 4,456,007 A | 6/1984 | Nakao et al. |
| 4,481,139 A | 11/1984 | Folkers et al. |
| 4,483,922 A | 11/1984 | Carpenter |
| D276,654 S | 12/1984 | Snellman-Wasenius et al. |
| 4,487,327 A | 12/1984 | Grayson |
| 4,524,769 A | 6/1985 | Wetterlin |
| 4,526,804 A | 7/1985 | Escallon |
| 4,534,345 A | 8/1985 | Wetterlin |
| D282,209 S | 1/1986 | Newell et al. |
| 4,581,020 A | 4/1986 | Mittleman |
| 4,592,348 A | 6/1986 | Waters, IV et al. |
| 4,613,500 A | 9/1986 | Suzuki |
| 4,615,817 A | 10/1986 | McCoy |
| 4,624,861 A | 11/1986 | Yale et al. |
| 4,637,996 A | 1/1987 | Konishi |
| D288,852 S | 3/1987 | Miyoshi |
| 4,659,696 A | 4/1987 | Hirai et al. |
| 4,668,218 A | 5/1987 | Virtanen |
| 4,671,954 A | 6/1987 | Goldberg et al. |
| 4,681,752 A | 7/1987 | Melillo |
| D295,321 S | 4/1988 | Hallworth |
| 4,742,156 A | 5/1988 | Wright |
| 4,757,066 A | 7/1988 | Shiokari et al. |
| 4,792,451 A | 12/1988 | Kim |
| 4,811,731 A | 3/1989 | Newell et al. |
| D301,273 S | 5/1989 | Leonard |
| 4,835,312 A | 5/1989 | Itoh et al. |
| 4,841,964 A | 6/1989 | Hurka et al. |
| 4,847,091 A | 7/1989 | Illum |
| 4,849,227 A | 7/1989 | Cho |
| 4,861,627 A | 8/1989 | Mathiowitz |
| 4,866,051 A | 9/1989 | Hunt et al. |
| 4,873,087 A | 10/1989 | Morishita et al. |
| 4,887,722 A | 12/1989 | Greenward, Sr. |
| 4,900,730 A | 2/1990 | Miyauchi |
| 4,907,583 A | 3/1990 | Wetterlin et al. |
| 4,925,673 A | 5/1990 | Steiner |
| 4,926,852 A | 5/1990 | Zoltan et al. |
| 4,927,555 A | 5/1990 | Colarusso, Jr. |
| 4,927,928 A | 5/1990 | Shroot et al. |
| 4,946,828 A | 8/1990 | Markussen |
| 4,981,295 A | 1/1991 | Belman et al. |
| 4,981,625 A | 1/1991 | Rhim et al. |
| 4,983,402 A | 1/1991 | Steiner et al. |
| 4,984,158 A | 1/1991 | Hillsman |
| 4,991,605 A | 2/1991 | Keritsis |
| 4,998,624 A | 3/1991 | Capes et al. |
| 5,006,343 A | 4/1991 | Benson |
| D316,902 S | 5/1991 | Hoefling |
| 5,017,383 A | 5/1991 | Ozawa et al. |
| 5,019,400 A | 5/1991 | Gombotz et al. |
| 5,021,376 A | 6/1991 | Nienburg et al. |
| 5,027,806 A | 7/1991 | Zoltan et al. |
| 5,042,975 A | 8/1991 | Chien |
| D321,570 S | 11/1991 | Blasdell et al. |
| 5,067,500 A | 11/1991 | Keritsis |
| 5,069,204 A | 12/1991 | Smith et al. |
| 5,074,418 A | 12/1991 | Buan et al. |
| 5,075,027 A | 12/1991 | Dixit et al. |
| 5,098,590 A | 3/1992 | Dixit et al. |
| 5,105,291 A | 4/1992 | Matsumoto et al. |
| D326,517 S | 5/1992 | Funai et al. |
| 5,110,007 A | 5/1992 | Law et al. |
| 5,110,823 A | 5/1992 | Hamaguchi et al. |
| 5,118,666 A | 6/1992 | Habener |
| 5,120,712 A | 6/1992 | Habener |
| 5,124,291 A | 6/1992 | Bremer et al. |
| 5,131,539 A | 7/1992 | Karita et al. |
| 5,139,878 A | 8/1992 | Kim |
| 5,145,684 A | 9/1992 | Liversidge et al. |
| 5,152,284 A | 10/1992 | Valentini et al. |
| D331,106 S | 11/1992 | Fuchs |
| 5,167,506 A | 12/1992 | Kilis et al. |
| 5,170,801 A | 12/1992 | Casper et al. |
| 5,188,837 A | 2/1993 | Domb |
| 5,196,049 A | 3/1993 | Coombs et al. |
| 5,201,308 A | 4/1993 | Newhouse |
| 5,203,768 A | 4/1993 | Haak et al. |
| 5,204,108 A | 4/1993 | Illum |
| 5,208,998 A | 5/1993 | Dyler, Jr. |
| 5,215,739 A | 6/1993 | Kamishita et al. |
| D337,636 S | 7/1993 | Kocinski |
| D338,062 S | 8/1993 | Yair |
| D338,268 S | 8/1993 | Kobayashi et al. |
| 5,239,992 A | 8/1993 | Bougamont et al. |
| 5,239,993 A | 8/1993 | Evans |
| 5,244,653 A | 9/1993 | Berke et al. |
| 5,250,287 A | 10/1993 | Cocozza |
| D340,975 S | 11/1993 | Sladek |
| 5,260,306 A | 11/1993 | Boardman et al. |
| 5,270,305 A | 12/1993 | Palmer |
| 5,287,850 A | 2/1994 | Haber et al. |
| D344,796 S | 3/1994 | Sochon et al. |
| D344,797 S | 3/1994 | Sochon et al. |
| D345,013 S | 3/1994 | Huck et al. |
| 5,301,666 A | 4/1994 | Lerk et al. |
| 5,306,453 A | 4/1994 | Shulman |
| D347,057 S | 5/1994 | Yair |
| D348,100 S | 6/1994 | Clarke |
| 5,320,094 A | 6/1994 | Laube et al. |
| D348,928 S | 7/1994 | Ashley et al. |
| D348,929 S | 7/1994 | Paton |
| 5,327,883 A | 7/1994 | Williams et al. |
| 5,328,464 A | 7/1994 | Kriesel et al. |
| 5,331,953 A | 7/1994 | Andersson et al. |
| 5,333,106 A | 7/1994 | Lanpher et al. |
| D349,572 S | 8/1994 | Jagnandan et al. |
| D350,193 S | 8/1994 | Huck et al. |
| 5,337,740 A | 8/1994 | Armstrong et al. |
| D350,602 S | 9/1994 | Hobbs et al. |
| D350,821 S | 9/1994 | Wright et al. |
| 5,351,683 A | 10/1994 | Chiesi et al. |
| 5,352,461 A | 10/1994 | Feldstein et al. |
| 5,354,562 A | 10/1994 | Platz |
| 5,358,734 A | 10/1994 | Lenox et al. |
| D352,107 S | 11/1994 | Meier et al. |
| 5,360,614 A | 11/1994 | Fox et al. |
| 5,363,842 A | 11/1994 | Mishelevich et al. |
| 5,364,838 A | 11/1994 | Rubsamen |
| 5,372,128 A | 12/1994 | Haber et al. |
| D355,029 S | 1/1995 | Kinneir et al. |
| 5,385,904 A | 1/1995 | Andersson et al. |
| 5,394,868 A | 3/1995 | Ambrosio et al. |
| 5,401,516 A | 3/1995 | Milstein et al. |
| D357,603 S | 4/1995 | Wolff |
| 5,404,871 A | 4/1995 | Goodman et al. |
| D358,880 S | 5/1995 | Mulhauser et al. |
| 5,413,804 A | 5/1995 | Rhodes |
| 5,415,162 A | 5/1995 | Casper et al. |
| D359,153 S | 6/1995 | Viggiano |
| D359,555 S | 6/1995 | Funai et al. |
| 5,424,286 A | 6/1995 | Eng |
| 5,437,271 A | 8/1995 | Hodson et al. |
| 5,443,841 A | 8/1995 | Milstein et al. |
| D362,500 S | 9/1995 | Cook et al. |
| 5,447,150 A | 9/1995 | Bacon |
| 5,447,151 A | 9/1995 | Bruna et al. |
| 5,447,728 A | 9/1995 | Milstein et al. |
| 5,451,410 A | 9/1995 | Milstein et al. |
| D363,775 S | 10/1995 | Hobbs |
| 5,454,871 A | 10/1995 | Liaw et al. |
| 5,455,335 A | 10/1995 | Kahne et al. |
| 5,458,135 A | 10/1995 | Patton et al. |
| 5,469,750 A | 11/1995 | Lloyd et al. |
| 5,469,971 A | 11/1995 | Chilton et al. |

(56) References Cited

U.S. PATENT DOCUMENTS

| | | |
|---|---|---|
| 5,476,093 A | 12/1995 | Laniken |
| 5,477,285 A | 12/1995 | Riddle et al. |
| D365,876 S | 1/1996 | Chawla |
| 5,482,032 A | 1/1996 | Smith et al. |
| 5,482,927 A | 1/1996 | Maniar et al. |
| 5,483,954 A | 1/1996 | Mecikalski |
| 5,484,606 A | 1/1996 | Dhaber et al. |
| 5,487,378 A | 1/1996 | Robertson et al. |
| 5,492,112 A | 2/1996 | Mecikalski et al. |
| D368,364 S | 4/1996 | Reitano et al. |
| 5,503,144 A | 4/1996 | Bacon |
| 5,503,852 A | 4/1996 | Steiner et al. |
| 5,505,194 A | 4/1996 | Adjei et al. |
| 5,506,203 A | 4/1996 | Backstorm et al. |
| D370,255 S | 5/1996 | Yamamoto et al. |
| 5,514,646 A | 5/1996 | Chance et al. |
| 5,518,998 A | 5/1996 | Backstorm et al. |
| 5,524,613 A | 6/1996 | Haber et al. |
| 5,532,461 A | 7/1996 | Crummenauer et al. |
| 5,533,502 A | 7/1996 | Piper |
| 5,533,505 A | 7/1996 | Kallstrand et al. |
| 5,541,155 A | 7/1996 | Leone-Bay |
| 5,542,411 A | 8/1996 | Rex |
| 5,542,539 A | 8/1996 | Early |
| 5,545,618 A | 8/1996 | Buckley et al. |
| 5,547,929 A | 8/1996 | Anderson, Jr. et al. |
| 5,562,909 A | 10/1996 | Allcock et al. |
| 5,562,918 A | 10/1996 | Stimpson |
| 5,568,884 A | 10/1996 | Bruna |
| 5,570,810 A | 11/1996 | Lambelet, Jr. et al. |
| 5,571,795 A | 11/1996 | Kahne et al. |
| 5,574,008 A | 11/1996 | Johnson et al. |
| 5,577,497 A | 11/1996 | Mecikalski et al. |
| 5,578,323 A | 11/1996 | Milstein et al. |
| 5,584,417 A | 12/1996 | Graf et al. |
| D377,215 S | 1/1997 | Rand |
| D377,686 S | 1/1997 | Waldeck et al. |
| 5,595,175 A | 1/1997 | Malcher et al. |
| 5,596,701 A | 1/1997 | Augusteijn et al. |
| D377,861 S | 2/1997 | Jacober |
| 5,598,835 A | 2/1997 | von Schrader |
| 5,601,846 A | 2/1997 | Milstein et al. |
| 5,610,271 A | 3/1997 | Dooley et al. |
| 5,614,492 A | 3/1997 | Habener |
| 5,615,670 A | 4/1997 | Rhodes et al. |
| 5,617,844 A | 4/1997 | King |
| 5,619,984 A | 4/1997 | Hodson et al. |
| 5,622,164 A | 4/1997 | Kilis et al. |
| 5,622,166 A | 4/1997 | Eisele et al. |
| 5,623,724 A | 4/1997 | Gurkovich et al. |
| 5,623,920 A | 4/1997 | Bryant |
| D379,506 S | 5/1997 | Maher |
| 5,629,020 A | 5/1997 | Leone-Bay |
| 5,631,224 A | 5/1997 | Efendic et al. |
| 5,632,971 A | 5/1997 | Yang |
| 5,634,900 A | 6/1997 | Makino et al. |
| 5,639,441 A | 6/1997 | Sievers et al. |
| 5,641,861 A | 6/1997 | Dooley et al. |
| D381,416 S | 7/1997 | Hansson et al. |
| 5,642,727 A | 7/1997 | Datta et al. |
| 5,642,728 A | 7/1997 | Andersson et al. |
| 5,643,957 A | 7/1997 | Leone-Bay et al. |
| 5,645,051 A | 7/1997 | Schultz |
| 5,651,359 A | 7/1997 | Bougamont et al. |
| 5,653,961 A | 8/1997 | McNally et al. |
| 5,655,516 A | 8/1997 | Goodman et al. |
| 5,655,523 A | 8/1997 | Hodson et al. |
| 5,657,748 A | 8/1997 | Braithwaite |
| 5,658,878 A | 8/1997 | Backstorm et al. |
| 5,660,169 A | 8/1997 | Kallstrand et al. |
| 5,672,581 A | 9/1997 | Rubsamen et al. |
| 5,673,686 A | 10/1997 | Villax et al. |
| 5,679,377 A | 10/1997 | Bernstein et al. |
| 5,687,710 A | 11/1997 | Ambrosio et al. |
| 5,690,910 A | 11/1997 | Ahmed et al. |
| 5,693,338 A | 12/1997 | Milstein |
| 5,699,789 A | 12/1997 | Hendricks |
| D389,238 S | 1/1998 | Kirk, III et al. |
| D389,570 S | 1/1998 | Savolainen |
| 5,705,483 A | 1/1998 | Galloway et al. |
| D390,651 S | 2/1998 | Smith et al. |
| D390,653 S | 2/1998 | Blasdell et al. |
| 5,714,007 A | 2/1998 | Pletcher et al. |
| 5,714,167 A | 2/1998 | Milstein et al. |
| 5,715,811 A | 2/1998 | Ohki et al. |
| 5,727,333 A | 3/1998 | Folan |
| 5,727,546 A | 3/1998 | Clarke et al. |
| 5,740,793 A | 4/1998 | Hodson et al. |
| 5,740,794 A | 4/1998 | Smith et al. |
| 5,746,197 A | 5/1998 | Williams |
| 5,746,227 A | 5/1998 | Rose et al. |
| 5,747,445 A | 5/1998 | Backstrom et al. |
| 5,752,505 A | 5/1998 | Ohki et al. |
| 5,755,218 A | 5/1998 | Johansson et al. |
| D395,147 S | 6/1998 | Vidgren et al. |
| D395,499 S | 6/1998 | Eisele et al. |
| 5,758,638 A | 6/1998 | Kreamer |
| 5,763,396 A | 6/1998 | Weiner et al. |
| 5,766,620 A | 6/1998 | Heiber et al. |
| 5,766,633 A | 6/1998 | Milstein et al. |
| 5,769,073 A | 6/1998 | Eason et al. |
| 5,772,085 A | 6/1998 | Bryant et al. |
| RE35,862 E | 7/1998 | Steiner et al. |
| 5,775,320 A | 7/1998 | Patton et al. |
| 5,785,049 A | 7/1998 | Smith et al. |
| 5,785,989 A | 7/1998 | Stanley et al. |
| D397,435 S | 8/1998 | Naumann |
| 5,792,451 A | 8/1998 | Sarubbi et al. |
| 5,794,613 A | 8/1998 | Piskorski |
| 5,797,391 A | 8/1998 | Cook et al. |
| D398,992 S | 9/1998 | Feret |
| 5,799,821 A | 9/1998 | Lambelet, Jr. et al. |
| 5,807,315 A | 9/1998 | Va Antwerp et al. |
| 5,809,997 A | 9/1998 | Wolf |
| 5,811,127 A | 9/1998 | Milstein et al. |
| 5,813,397 A | 9/1998 | Goodman et al. |
| 5,817,343 A | 10/1998 | Burke |
| 5,824,345 A | 10/1998 | Milstein et al. |
| 5,839,429 A | 11/1998 | Marnfeldt et al. |
| 5,840,279 A | 11/1998 | Narodylo et al. |
| 5,840,340 A | 11/1998 | Milstein et al. |
| 5,846,447 A | 12/1998 | Beatty |
| 5,848,589 A | 12/1998 | Welnetz |
| 5,849,322 A | 12/1998 | Ebert et al. |
| 5,857,457 A | 1/1999 | Hyppola |
| 5,858,099 A | 1/1999 | Sun et al. |
| 5,865,012 A | 2/1999 | Hansson et al. |
| 5,868,774 A | 2/1999 | Reil |
| 5,874,064 A | 2/1999 | Edwards et al. |
| 5,875,776 A | 3/1999 | Vaghefi |
| 5,877,174 A | 3/1999 | Ono et al. |
| 5,881,719 A | 3/1999 | Gottenauer et al. |
| 5,881,721 A | 3/1999 | Bunce et al. |
| 5,884,620 A | 3/1999 | Gonda et al. |
| 5,888,477 A | 3/1999 | Gonda et al. |
| 5,896,855 A | 4/1999 | Hobbs et al. |
| 5,901,703 A | 5/1999 | Ohki et al. |
| 5,904,139 A | 5/1999 | Hauser |
| D410,541 S | 6/1999 | Moulin |
| D411,005 S | 6/1999 | Coe |
| 5,908,639 A | 6/1999 | Simpkin et al. |
| 5,912,011 A | 6/1999 | Makino et al. |
| 5,918,594 A | 7/1999 | Asking et al. |
| 5,919,897 A | 7/1999 | Dooley et al. |
| 5,921,237 A | 7/1999 | Eisele et al. |
| 5,922,253 A | 7/1999 | Herbert et al. |
| 5,924,419 A | 7/1999 | Kotliar |
| 5,929,027 A | 7/1999 | Takama et al. |
| D412,572 S | 8/1999 | Gray |
| D412,744 S | 8/1999 | Braithwaite |
| D412,978 S | 8/1999 | Cameron |
| D412,979 S | 8/1999 | Weinstein et al. |
| 5,934,273 A | 8/1999 | Andersson et al. |
| 5,942,242 A | 8/1999 | Mizushima et al. |

(56) References Cited

U.S. PATENT DOCUMENTS

| | | |
|---|---|---|
| 5,972,242 A | 8/1999 | Mizushima et al. |
| 5,948,749 A | 9/1999 | Igarashi et al. |
| 5,952,008 A | 9/1999 | Backstrom et al. |
| 5,954,047 A | 9/1999 | Armer et al. |
| 5,965,701 A | 10/1999 | Junien |
| 5,971,951 A | 10/1999 | Ruskewicz |
| D416,085 S | 11/1999 | Forssell et al. |
| D416,621 S | 11/1999 | Forssell et al. |
| D416,998 S | 11/1999 | Hodson et al. |
| D417,271 S | 11/1999 | Denyer et al. |
| 5,975,347 A | 11/1999 | Lambelet, Jr. et al. |
| 5,976,569 A | 11/1999 | Milstein |
| 5,976,574 A | 11/1999 | Gordon |
| 5,977,071 A | 11/1999 | Galloway et al. |
| 5,980,865 A | 11/1999 | Ahmed et al. |
| 5,981,488 A | 11/1999 | Hoffman |
| 5,983,893 A | 11/1999 | Wetterlin |
| 5,985,248 A | 11/1999 | Gordon et al. |
| 5,985,309 A | 11/1999 | Edwards et al. |
| 5,990,077 A | 11/1999 | Drucker |
| D417,732 S | 12/1999 | Dagsland et al. |
| D417,912 S | 12/1999 | Dagsland et al. |
| 5,996,577 A | 12/1999 | Ohki et al. |
| 5,997,848 A | 12/1999 | Patton et al. |
| 6,001,336 A | 12/1999 | Gordon |
| 6,006,747 A | 12/1999 | Eisele et al. |
| 6,006,753 A | 12/1999 | Efendic |
| D418,600 S | 1/2000 | Haerle |
| D420,736 S | 2/2000 | Moulin |
| 6,026,809 A | 2/2000 | Abrams et al. |
| 6,029,663 A | 2/2000 | Eisele et al. |
| D421,800 S | 3/2000 | Doat |
| 6,039,208 A | 3/2000 | Lambelet et al. |
| 6,043,214 A | 3/2000 | Jensen et al. |
| 6,045,828 A | 4/2000 | Bystorm et al. |
| 6,051,256 A | 4/2000 | Platz et al. |
| 6,051,551 A | 4/2000 | Hughes et al. |
| 6,055,980 A | 5/2000 | Mecikalski et al. |
| 6,056,169 A | 5/2000 | Bruna et al. |
| 6,060,069 A | 5/2000 | Hill et al. |
| 6,063,910 A | 5/2000 | Debenedetti et al. |
| 6,071,497 A | 6/2000 | Steiner et al. |
| 6,073,629 A | 6/2000 | Hardy et al. |
| 6,076,521 A | 6/2000 | Lindahl et al. |
| 6,077,543 A | 6/2000 | Gordon et al. |
| 6,080,762 A | 6/2000 | Allen et al. |
| 6,085,745 A | 6/2000 | Levander et al. |
| D428,486 S | 7/2000 | Schuckmann |
| 6,087,334 A | 7/2000 | Beeley et al. |
| 6,087,351 A | 7/2000 | Nye |
| 6,089,228 A | 7/2000 | Smith et al. |
| 6,095,136 A | 8/2000 | Virtanen |
| 6,098,618 A | 8/2000 | Jennings et al. |
| 6,098,619 A | 8/2000 | Britto et al. |
| 6,102,035 A | 8/2000 | Asking et al. |
| 6,105,571 A | 8/2000 | Coffee |
| 6,105,574 A | 8/2000 | Jahnsson |
| 6,109,261 A | 8/2000 | Clarke et al. |
| 6,109,481 A | 8/2000 | Alexander et al. |
| 6,099,517 A | 9/2000 | Daughtery |
| 6,116,237 A | 9/2000 | Schultz |
| 6,116,238 A | 9/2000 | Jackson et al. |
| 6,116,239 A | 9/2000 | Volgyesi |
| 6,119,684 A | 9/2000 | Nohl et al. |
| 6,119,688 A | 9/2000 | Whaley et al. |
| 6,131,567 A | 10/2000 | Gonda et al. |
| 6,132,766 A | 10/2000 | Sankaram et al. |
| 6,133,235 A | 10/2000 | Galloway et al. |
| 6,142,145 A | 11/2000 | Dagsland |
| 6,152,130 A | 11/2000 | Abrams |
| 6,153,613 A | 11/2000 | Ono et al. |
| 6,155,423 A | 12/2000 | Katzne et al. |
| 6,156,114 A | 12/2000 | Bell et al. |
| 6,158,431 A | 12/2000 | Poole |
| 6,159,360 A | 12/2000 | Gerteis et al. |
| RE37,053 E | 2/2001 | Hanes et al. |
| 6,182,655 B1 | 2/2001 | Keller et al. |
| 6,187,291 B1 | 2/2001 | Weinstein et al. |
| 6,191,102 B1 | 2/2001 | DiMarchi et al. |
| 6,192,876 B1 | 2/2001 | Denyer et al. |
| 6,193,844 B1 | 2/2001 | McLaughlin et al. |
| 6,193,957 B1 | 2/2001 | Ahmed |
| D438,612 S | 3/2001 | Suh |
| D439,325 S | 3/2001 | Frost |
| D439,656 S | 3/2001 | Andersson et al. |
| 6,198,847 B1 | 3/2001 | Washizawa |
| D441,446 S | 5/2001 | Dagsland et al. |
| D441,859 S | 5/2001 | Pera |
| D442,685 S | 5/2001 | Sladek |
| 6,235,725 B1 | 5/2001 | Ahmed |
| D444,226 S | 6/2001 | Geert-Jensen et al. |
| 6,247,598 B1 | 6/2001 | Hosaka et al. |
| 6,250,300 B1 | 6/2001 | Andersson et al. |
| 6,254,854 B1 | 7/2001 | Edwards et al. |
| 6,257,232 B1 | 7/2001 | Andersson et al. |
| 6,258,816 B1 | 7/2001 | Singh et al. |
| 6,263,871 B1 | 7/2001 | Brown et al. |
| 6,269,952 B1 | 8/2001 | Watt et al. |
| 6,273,084 B1 | 8/2001 | Frid |
| 6,273,085 B1 | 8/2001 | Eisele et al. |
| 6,273,086 B1 | 8/2001 | Ohki et al. |
| 6,277,819 B1 | 8/2001 | Efendic |
| 6,279,511 B1 | 8/2001 | Loughnane |
| D448,076 S | 9/2001 | von Shuckmann |
| 6,286,506 B1 | 9/2001 | MacAndrew et al. |
| 6,286,507 B1 | 9/2001 | Jahnsson |
| 6,294,204 B1 | 9/2001 | Rossling et al. |
| D449,684 S | 10/2001 | Christup et al. |
| 6,298,846 B1 | 10/2001 | Ohki et al. |
| 6,298,847 B1 | 10/2001 | Datta et al. |
| D450,117 S | 11/2001 | Braithwaite et al. |
| D451,597 S | 12/2001 | Suh |
| 6,328,034 B1 | 12/2001 | Eisele et al. |
| 6,331,318 B1 | 12/2001 | Milstein |
| D452,910 S | 1/2002 | Braithwaite et al. |
| 6,335,316 B1 | 1/2002 | Hughes et al. |
| D453,264 S | 2/2002 | Acevedo, Jr. |
| 6,347,629 B1 | 2/2002 | Braithwaite |
| 6,348,447 B1 | 2/2002 | Hellstorm et al. |
| 6,357,442 B1 | 3/2002 | Casper et al. |
| 6,358,058 B1 | 3/2002 | Strupat et al. |
| 6,358,924 B1 | 3/2002 | Hoffman |
| 6,360,743 B1 | 3/2002 | Andersson et al. |
| 6,360,929 B1 | 3/2002 | McCarthy |
| D455,208 S | 4/2002 | Bacon et al. |
| 6,363,932 B1 | 4/2002 | Forchione et al. |
| 6,365,190 B1 | 4/2002 | Gordon et al. |
| 6,372,258 B1 | 4/2002 | Platz et al. |
| 6,375,975 B1 | 4/2002 | Modi |
| 6,380,357 B2 | 4/2002 | Hermeling et al. |
| 6,386,195 B1 | 5/2002 | Coffee |
| 6,388,053 B1 | 5/2002 | Galloway et al. |
| 6,394,085 B1 | 5/2002 | Hardy et al. |
| 6,395,300 B1 | 5/2002 | Straub et al. |
| 6,395,744 B1 | 5/2002 | Adams et al. |
| 6,395,774 B1 | 5/2002 | Milstein |
| 6,410,513 B1 | 6/2002 | Galloway et al. |
| D460,173 S | 7/2002 | Harrison et al. |
| 6,415,784 B1 | 7/2002 | Christup et al. |
| 6,418,926 B1 | 7/2002 | Chawla |
| 6,423,344 B1 | 7/2002 | Platz et al. |
| D461,239 S | 8/2002 | Cassidy |
| 6,427,688 B1 | 8/2002 | Ligotke et al. |
| 6,428,771 B1 | 8/2002 | Steiner et al. |
| 6,428,805 B1 | 8/2002 | Dohi et al. |
| 6,432,383 B1 | 8/2002 | Modi |
| 6,436,443 B2 | 8/2002 | Edwards et al. |
| 6,439,227 B1 | 8/2002 | Myrman et al. |
| 6,440,463 B1 | 8/2002 | Feldstein et al. |
| 6,441,172 B1 | 8/2002 | Nefzi et al. |
| D463,544 S | 9/2002 | Engelberth et al. |
| 6,443,143 B1 | 9/2002 | Ishida et al. |
| 6,444,226 B1 | 9/2002 | Steiner et al. |
| 6,446,626 B1 | 9/2002 | Virtanen |

(56) References Cited

U.S. PATENT DOCUMENTS

| | | |
|---|---|---|
| 6,446,627 B1 | 9/2002 | Bowman et al. |
| 6,447,750 B1 | 9/2002 | Cutie et al. |
| 6,447,751 B1 | 9/2002 | Weinstein et al. |
| 6,447,753 B2 | 9/2002 | Edwards et al. |
| 6,451,337 B1 | 9/2002 | Smith et al. |
| 6,457,470 B1 | 10/2002 | Coffee |
| 6,468,507 B1 | 10/2002 | Cutie et al. |
| 6,470,884 B2 | 10/2002 | Horlin |
| 6,479,049 B1 | 11/2002 | Platz et al. |
| 6,484,715 B1 | 11/2002 | Ritsche et al. |
| 6,484,717 B1 | 11/2002 | Dagsland et al. |
| D469,527 S | 1/2003 | Keller et al. |
| 6,503,480 B1 | 1/2003 | Edwards et al. |
| 6,509,006 B1 | 1/2003 | Platz et al. |
| 6,509,313 B1 | 1/2003 | Smith |
| D469,866 S | 2/2003 | Albulet et al. |
| 6,514,482 B1 | 2/2003 | Bartus et al. |
| 6,518,239 B1 | 2/2003 | Kuo et al. |
| 6,523,536 B2 | 2/2003 | Fugelsang et al. |
| D471,273 S | 3/2003 | Albulet et al. |
| 6,528,096 B1 | 3/2003 | Musa et al. |
| 6,532,437 B1 | 3/2003 | Clardy et al. |
| 6,536,427 B2 | 3/2003 | Davies et al. |
| D473,298 S | 4/2003 | Bowman et al. |
| D473,640 S | 4/2003 | Cuffaro et al. |
| 6,540,672 B1 | 4/2003 | Simonsen et al. |
| 6,540,982 B1 | 4/2003 | Adjei et al. |
| 6,540,983 B1 | 4/2003 | Adjei et al. |
| 6,543,448 B1 | 4/2003 | Smith et al. |
| 6,546,929 B2 | 4/2003 | Burr et al. |
| 6,555,127 B2 | 4/2003 | Steiner |
| 6,555,521 B2 | 4/2003 | Hermeling et al. |
| D474,536 S | 5/2003 | Albulet et al. |
| D475,133 S | 5/2003 | McLuckie |
| 6,557,549 B2 | 5/2003 | Schmidt et al. |
| 6,561,186 B2 | 5/2003 | Casper et al. |
| 6,567,686 B2 | 5/2003 | Sexton |
| 6,568,390 B2 | 5/2003 | Nichols et al. |
| 6,569,406 B2 | 5/2003 | Stevenson et al. |
| 6,571,793 B1 | 6/2003 | Nilsson et al. |
| 6,572,893 B2 | 6/2003 | Gordon et al. |
| 6,575,160 B1 | 6/2003 | Volgyesi |
| 6,575,162 B1 | 6/2003 | Rand |
| 6,578,571 B1 | 6/2003 | Watt |
| 6,582,728 B1 | 6/2003 | Platz et al. |
| 6,583,111 B1 | 6/2003 | DiMarchi |
| D477,665 S | 7/2003 | Myrman et al. |
| 6,589,560 B2 | 7/2003 | Foster et al. |
| 6,591,832 B1 | 7/2003 | DeJonge |
| 6,592,904 B2 | 7/2003 | Platz et al. |
| 6,595,205 B2 | 7/2003 | Andersson et al. |
| 6,595,208 B1 | 7/2003 | Coffee et al. |
| D478,983 S | 8/2003 | Whitehall et al. |
| 6,606,992 B1 | 8/2003 | Schuler et al. |
| D479,745 S | 9/2003 | Albulet et al. |
| 6,613,308 B2 | 9/2003 | Bartus et al. |
| 6,615,987 B1 | 9/2003 | Greenhill et al. |
| 6,620,910 B1 | 9/2003 | Calas et al. |
| 6,626,173 B2 | 9/2003 | Genova et al. |
| D480,806 S | 10/2003 | Engelberth et al. |
| 6,630,169 B1 | 10/2003 | Bot et al. |
| 6,632,258 B1 | 10/2003 | Wheelock et al. |
| 6,632,456 B1 | 10/2003 | Backstrom et al. |
| 6,635,283 B2 | 10/2003 | Edwards et al. |
| 6,637,431 B2 | 10/2003 | Ekelius et al. |
| 6,640,050 B2 | 10/2003 | Nichols et al. |
| 6,644,309 B2 | 11/2003 | Casper et al. |
| 6,645,468 B2 | 11/2003 | Cutie et al. |
| 6,645,504 B1 | 11/2003 | Weiner et al. |
| 6,652,838 B2 | 11/2003 | Weinstein et al. |
| 6,652,885 B2 | 11/2003 | Steiner et al. |
| D483,860 S | 12/2003 | Knoch |
| 6,655,379 B2 | 12/2003 | Clark et al. |
| 6,655,380 B1 | 12/2003 | Andersson et al. |
| 6,655,381 B2 | 12/2003 | Keane et al. |
| 6,660,716 B1 | 12/2003 | Yakubu-Madus et al. |
| 6,663,898 B2 | 12/2003 | Milstein |
| 6,668,826 B1 | 12/2003 | Myrman et al. |
| 6,672,304 B1 | 1/2004 | Casper et al. |
| 6,676,931 B2 | 1/2004 | Dugger, III |
| 6,679,255 B2 | 1/2004 | Pera |
| 6,681,767 B1 | 1/2004 | Patton et al. |
| 6,681,768 B2 | 1/2004 | Haaije de Boer et al. |
| 6,685,967 B1 | 2/2004 | Patton et al. |
| 6,696,090 B1 | 2/2004 | Nilsson et al. |
| 6,698,421 B2 | 3/2004 | Attolini |
| 6,698,422 B2 | 3/2004 | Fugelsang et al. |
| 6,698,425 B1 | 3/2004 | Widerstorm |
| 6,701,917 B2 | 3/2004 | O'Leary |
| 6,703,361 B2 | 3/2004 | Weiner et al. |
| 6,703,365 B2 | 3/2004 | Galloway et al. |
| 6,703,381 B1 | 3/2004 | Ekwuribe et al. |
| 6,705,313 B2 | 3/2004 | Niccolai |
| 6,715,486 B2 | 4/2004 | Gieschen et al. |
| 6,715,487 B2 | 4/2004 | Nichols et al. |
| 6,718,972 B2 | 4/2004 | O'Leary |
| 6,720,407 B1 | 4/2004 | Hughes et al. |
| 6,722,363 B1 | 4/2004 | von Schuckmann |
| D489,448 S | 5/2004 | Shayan |
| 6,729,324 B2 | 5/2004 | Casper et al. |
| 6,729,328 B2 | 5/2004 | Raul |
| 6,737,045 B2 | 5/2004 | Patton |
| 6,745,761 B2 | 6/2004 | Christup et al. |
| 6,747,006 B2 | 6/2004 | Efendic |
| 6,748,946 B1 | 6/2004 | Rand et al. |
| 6,748,947 B2 | 6/2004 | Keane et al. |
| 6,752,145 B1 | 6/2004 | Bonney et al. |
| 6,755,190 B2 | 6/2004 | Rasmussen |
| D492,769 S | 7/2004 | Hatanaka |
| D493,220 S | 7/2004 | Burge et al. |
| D493,519 S | 7/2004 | Jonsson et al. |
| 6,774,112 B2 | 8/2004 | Gougoutas |
| 6,787,152 B2 | 9/2004 | Kirby et al. |
| 6,790,496 B1 | 9/2004 | Levander et al. |
| 6,792,945 B2 | 9/2004 | Davies et al. |
| 6,794,357 B1 | 9/2004 | Backstrom et al. |
| 6,797,258 B2 | 9/2004 | Platz et al. |
| 6,799,572 B2 | 10/2004 | Nichols et al. |
| 6,800,643 B2 | 10/2004 | Cuenoud et al. |
| 6,803,044 B1 | 10/2004 | Catania et al. |
| 6,821,949 B2 | 11/2004 | Bridon et al. |
| 6,823,863 B2 | 11/2004 | Huxham et al. |
| D499,802 S | 12/2004 | Pinon et al. |
| 6,830,046 B2 | 12/2004 | Blakley et al. |
| 6,835,372 B2 | 12/2004 | Kuo et al. |
| 6,838,075 B2 | 1/2005 | Stevenson et al. |
| 6,838,076 B2 | 1/2005 | Platton et al. |
| 6,847,595 B2 | 1/2005 | Tanaka |
| 6,848,443 B2 | 2/2005 | Schmidt et al. |
| 6,849,708 B1 | 2/2005 | Habener |
| 6,852,690 B1 | 2/2005 | Nauck et al. |
| 6,858,199 B1 | 2/2005 | Edwards et al. |
| 6,860,262 B2 | 3/2005 | Christup et al. |
| 6,866,037 B1 | 3/2005 | Aslin et al. |
| 6,871,646 B2 | 3/2005 | Keane et al. |
| 6,871,647 B2 | 3/2005 | Allan et al. |
| 6,880,554 B1 | 4/2005 | Coffee |
| 6,881,423 B2 | 4/2005 | Dohi et al. |
| 6,884,435 B1 | 4/2005 | O'Hagan et al. |
| 6,887,459 B1 | 5/2005 | Haeberlin |
| 6,887,849 B2 | 5/2005 | Bridon et al. |
| 6,889,687 B1 | 5/2005 | Olsson |
| 6,892,728 B2 | 5/2005 | Helgesson et al. |
| 6,896,906 B2 | 5/2005 | Hastedt et al. |
| D506,680 S | 6/2005 | Saelzer |
| 6,904,907 B2 | 6/2005 | Speldrich et al. |
| 6,906,030 B2 | 6/2005 | Milstein |
| 6,916,354 B2 | 7/2005 | Elliot |
| 6,918,991 B2 | 7/2005 | Chickering, III et al. |
| 6,921,458 B2 | 7/2005 | Chickering, III et al. |
| 6,921,528 B2 | 7/2005 | Edwards et al. |
| 6,923,175 B2 | 8/2005 | Poole et al. |
| D509,296 S | 9/2005 | Minshull et al. |
| D509,898 S | 9/2005 | Bunce et al. |

(56) References Cited

U.S. PATENT DOCUMENTS

| | | |
|---|---|---|
| 6,948,496 B2 | 9/2005 | Eason et al. |
| 6,949,258 B2 | 9/2005 | Zhang |
| 6,951,215 B1 | 10/2005 | Hoffman |
| 6,953,812 B2 | 10/2005 | Joregenson et al. |
| D511,208 S | 11/2005 | Pardonge et al. |
| D511,977 S | 11/2005 | Saelzer |
| 6,962,006 B2 | 11/2005 | Chickering, III et al. |
| D512,777 S | 12/2005 | Beisner et al. |
| 6,979,437 B2 | 12/2005 | Bartus et al. |
| D514,222 S | 1/2006 | Andersson et al. |
| 6,981,499 B2 | 1/2006 | Andersson et al. |
| 6,989,155 B1 | 1/2006 | Ganderton et al. |
| 6,991,779 B2 | 1/2006 | Steiner et al. |
| D515,696 S | 2/2006 | Lucking et al. |
| D515,924 S | 2/2006 | Grant |
| D516,211 S | 2/2006 | Minshull et al. |
| 6,998,387 B1 | 2/2006 | Goke et al. |
| D518,170 S | 3/2006 | Clarke et al. |
| D518,171 S | 3/2006 | Anderson et al. |
| 7,022,674 B2 | 4/2006 | DeFelippis et al. |
| 7,025,056 B2 | 4/2006 | Eason et al. |
| 7,028,686 B2 | 4/2006 | Gonda et al. |
| 7,030,084 B2 | 4/2006 | Ekwuribe et al. |
| 7,032,593 B2 | 4/2006 | Johnston et al. |
| 7,035,294 B2 | 4/2006 | Dove et al. |
| 7,047,967 B2 | 5/2006 | Knudsen |
| 7,048,908 B2 | 5/2006 | Basu et al. |
| 7,060,274 B2 | 6/2006 | Blumberg et al. |
| 7,067,129 B2 | 6/2006 | Blumberg et al. |
| 7,077,130 B2 | 7/2006 | Nichols et al. |
| 7,080,642 B2 | 7/2006 | Hodson et al. |
| 7,084,243 B2 | 8/2006 | Glaesner et al. |
| 7,093,594 B2 | 8/2006 | Harrison et al. |
| 7,093,595 B2 | 8/2006 | Nesbitt |
| D527,817 S | 9/2006 | Ziegler et al. |
| 7,101,843 B2 | 9/2006 | Glaesner et al. |
| 7,101,866 B2 | 9/2006 | Biggadike et al. |
| 7,105,489 B2 | 9/2006 | Hathaway |
| 7,107,988 B2 | 9/2006 | Pinon et al. |
| 7,109,161 B1 | 9/2006 | Gayed |
| D529,604 S | 10/2006 | Young et al. |
| 7,125,566 B2 | 10/2006 | Etter |
| 7,128,067 B2 | 10/2006 | Byron et al. |
| 7,131,441 B1 | 11/2006 | Keller et al. |
| 7,132,115 B2 | 11/2006 | Musa et al. |
| 7,140,365 B2 | 11/2006 | Poole et al. |
| D533,268 S | 12/2006 | Olfati |
| 7,143,764 B1 | 12/2006 | Dagsland et al. |
| 7,143,765 B2 | 12/2006 | Asking et al. |
| 7,144,863 B2 | 12/2006 | DeFelippis et al. |
| 7,146,978 B2 | 12/2006 | Edwards et al. |
| 7,151,456 B2 | 12/2006 | Godfrey |
| 7,163,014 B2 | 1/2007 | Nichols et al. |
| D537,522 S | 2/2007 | Cox et al. |
| 7,171,965 B2 | 2/2007 | Young et al. |
| 7,172,768 B2 | 2/2007 | Hastedt et al. |
| 7,179,788 B2 | 2/2007 | DeFelippis et al. |
| D537,936 S | 3/2007 | Cox et al. |
| D538,423 S | 3/2007 | Berube et al. |
| 7,185,650 B2 | 3/2007 | Huber et al. |
| D540,671 S | 4/2007 | Born |
| D541,151 S | 4/2007 | Born |
| 7,198,806 B2 | 4/2007 | Berndt |
| 7,211,557 B2 | 5/2007 | DiMarchi et al. |
| 7,219,664 B2 | 5/2007 | Ruckdeschel et al. |
| 7,223,728 B2 | 5/2007 | Yakubu-Madus et al. |
| D544,093 S | 6/2007 | Eriksen |
| 7,231,919 B2 | 6/2007 | Giroux |
| 7,232,897 B2 | 6/2007 | Hotamisligil et al. |
| 7,234,459 B2 | 6/2007 | Del Bon |
| 7,234,460 B2 | 6/2007 | Greenleaf et al. |
| 7,234,464 B2 | 6/2007 | Goede et al. |
| 7,238,663 B2 | 7/2007 | DeFelippis et al. |
| 7,246,617 B1 | 7/2007 | Hammer et al. |
| D548,330 S | 8/2007 | Cox et al. |
| D548,618 S | 8/2007 | Ferguson et al. |
| D548,619 S | 8/2007 | Ferguson et al. |
| D548,833 S | 8/2007 | Young et al. |
| D549,111 S | 8/2007 | Ferguson et al. |
| 7,258,118 B2 | 8/2007 | Goede et al. |
| 7,259,233 B2 | 8/2007 | Dodd et al. |
| D550,835 S | 9/2007 | Tanaka et al. |
| 7,265,087 B1 | 9/2007 | Goke et al. |
| 7,270,124 B2 | 9/2007 | Rasmussen |
| D552,729 S | 10/2007 | Cox et al. |
| 7,276,534 B2 | 10/2007 | Milstein |
| 7,278,419 B2 | 10/2007 | Gonda |
| 7,278,426 B2 | 10/2007 | Mryman et al. |
| 7,278,843 B2 | 10/2007 | Feldstein et al. |
| 7,279,457 B2 | 10/2007 | Pohl et al. |
| 7,284,553 B2 | 10/2007 | Hochrainer |
| D557,799 S | 12/2007 | Greenhalgh et al. |
| 7,305,986 B1 | 12/2007 | Steiner |
| 7,306,787 B2 | 12/2007 | Tarara et al. |
| D560,793 S | 1/2008 | Pearl et al. |
| 7,314,859 B2 | 1/2008 | Green et al. |
| 7,316,748 B2 | 1/2008 | Li et al. |
| 7,331,340 B2 | 2/2008 | Barney |
| 7,334,577 B2 | 2/2008 | Gumaste et al. |
| 7,344,734 B2 | 3/2008 | Heijerman et al. |
| D566,549 S | 4/2008 | Russell |
| 7,368,102 B2 | 5/2008 | Tarara et al. |
| 7,373,938 B2 | 5/2008 | Nichols et al. |
| 7,377,277 B2 | 5/2008 | Hickey et al. |
| 7,387,122 B2 | 6/2008 | Nishibayashi et al. |
| 7,399,528 B2 | 7/2008 | Caponetti et al. |
| 7,401,712 B2 | 7/2008 | Kaye et al. |
| 7,401,713 B2 | 7/2008 | Ede et al. |
| 7,402,564 B1 | 7/2008 | Schteingart et al. |
| 7,414,720 B2 | 8/2008 | Wachtel et al. |
| D577,815 S | 9/2008 | Gokhale et al. |
| 7,422,013 B2 | 9/2008 | Burr et al. |
| D579,549 S | 10/2008 | Birath et al. |
| 7,448,375 B2 | 11/2008 | Gonda et al. |
| 7,448,379 B2 | 11/2008 | Yamashita et al. |
| 7,451,761 B2 | 11/2008 | Hickey et al. |
| 7,453,556 B2 | 11/2008 | Hochrainer et al. |
| D583,463 S | 12/2008 | Wood et al. |
| 7,461,653 B2 | 12/2008 | Oliva |
| 7,462,367 B2 | 12/2008 | Schmidt et al. |
| 7,464,706 B2 | 12/2008 | Steiner et al. |
| 7,469,696 B2 | 12/2008 | Yang et al. |
| 7,500,479 B2 | 3/2009 | Nichols et al. |
| 7,503,324 B2 | 3/2009 | Barney et al. |
| 7,504,538 B2 | 3/2009 | Chang et al. |
| 7,517,874 B2 | 4/2009 | Beckett et al. |
| 7,520,278 B2 | 4/2009 | Crowder et al. |
| 7,521,069 B2 | 4/2009 | Patton et al. |
| 7,533,668 B1 | 5/2009 | Widerstrom |
| D594,753 S | 6/2009 | Eadicicco et al. |
| 7,556,798 B2 | 7/2009 | Edwards et al. |
| 7,559,322 B2 | 7/2009 | Foley et al. |
| D597,418 S | 8/2009 | Stojek |
| D597,657 S | 8/2009 | Kinsey et al. |
| D598,785 S | 8/2009 | Stojek |
| 7,584,846 B2 | 9/2009 | Senter |
| 7,598,222 B2 | 10/2009 | Prouty, Jr. et al. |
| D604,832 S | 11/2009 | Smutney |
| D604,833 S | 11/2009 | Polidoro |
| D605,752 S | 12/2009 | Polidoro |
| D605,753 S | 12/2009 | Smutney |
| 7,625,865 B2 | 12/2009 | Colombo |
| 7,648,960 B2 | 1/2010 | Steiner et al. |
| D613,849 S | 4/2010 | Smutney |
| D614,045 S | 4/2010 | Gaudenzi et al. |
| D614,760 S | 4/2010 | Smutney et al. |
| 7,694,676 B2 | 4/2010 | Wachtel |
| 7,708,014 B2 | 5/2010 | Yamashita et al. |
| 7,709,639 B2 | 5/2010 | Stevenson |
| 7,713,937 B2 | 5/2010 | Schteingart et al. |
| 7,727,963 B2 | 6/2010 | Schteingart et al. |
| 7,735,485 B2 | 6/2010 | Yamashita et al. |
| D620,812 S | 8/2010 | Gaudenzi et al. |
| 7,794,754 B2 | 9/2010 | Feldstein et al. |

(56) References Cited

U.S. PATENT DOCUMENTS

| | | |
|---|---|---|
| 7,799,344 B2 | 9/2010 | Oberg |
| 7,803,404 B2 | 9/2010 | Hokenson |
| 7,820,676 B2 | 10/2010 | Leone-Bay et al. |
| D626,836 S | 11/2010 | Lien |
| D628,090 S | 11/2010 | Stuiber et al. |
| 7,833,549 B2 | 11/2010 | Steiner et al. |
| 7,833,550 B2 | 11/2010 | Steiner et al. |
| 7,842,662 B2 | 11/2010 | Schteingart et al. |
| D629,505 S | 12/2010 | Adamo |
| D629,506 S | 12/2010 | Adamo |
| D629,886 S | 12/2010 | Adamo |
| D629,887 S | 12/2010 | Adamo |
| D629,888 S | 12/2010 | Adamo |
| D635,241 S | 3/2011 | McLean |
| D635,242 S | 3/2011 | Adamo |
| D635,243 S | 3/2011 | Kinsey |
| 7,913,688 B2 | 3/2011 | Cross |
| D636,867 S | 4/2011 | Polidoro et al. |
| D636,868 S | 4/2011 | Kinsey et al. |
| D636,869 S | 4/2011 | Laurenzi et al. |
| 7,919,119 B2 | 4/2011 | Straub et al. |
| 7,943,178 B2 | 5/2011 | Steiner et al. |
| 7,943,572 B2 | 5/2011 | Cheatham et al. |
| 7,954,491 B2 | 6/2011 | Hrkach |
| 7,959,609 B2 | 6/2011 | Gaydos et al. |
| D641,076 S | 7/2011 | Grunstad et al. |
| D643,308 S | 8/2011 | Bergey |
| D645,954 S | 9/2011 | Hately |
| D647,195 S | 10/2011 | Clarke et al. |
| D647,196 S | 10/2011 | Clarke et al. |
| 8,037,880 B2 | 10/2011 | Zhu et al. |
| 8,037,881 B2 | 10/2011 | Pentafragas |
| 8,039,431 B2 | 10/2011 | Wilson et al. |
| 8,047,203 B2 | 11/2011 | Young et al. |
| D652,322 S | 1/2012 | Stuiber et al. |
| 8,109,267 B2 | 2/2012 | Villax et al. |
| 8,119,593 B2 | 2/2012 | Richardson |
| D655,622 S | 3/2012 | Sadler et al. |
| 8,133,514 B2 | 3/2012 | Milstein |
| 8,146,588 B2 | 4/2012 | Steiner et al. |
| 8,156,936 B2 | 4/2012 | Steiner et al. |
| D659,020 S | 5/2012 | Kemner |
| D659,022 S | 5/2012 | Kemner |
| D660,956 S | 5/2012 | Zuyderhoudt |
| 8,166,970 B2 | 5/2012 | Poole et al. |
| 8,172,817 B2 | 5/2012 | Michaels et al. |
| 8,196,576 B2 | 6/2012 | Kriksunov et al. |
| 8,201,555 B2 | 6/2012 | Chawla |
| 8,202,992 B2 | 6/2012 | Stevenson |
| D663,830 S | 7/2012 | Sears |
| D664,640 S | 7/2012 | Smutney et al. |
| 8,215,300 B2 | 7/2012 | Steiner et al. |
| 8,217,007 B1 | 7/2012 | Schteingart et al. |
| 8,227,409 B2 | 7/2012 | Kraft |
| 8,236,766 B2 | 8/2012 | Schteingart et al. |
| 8,252,916 B2 | 8/2012 | Simard et al. |
| 8,258,095 B2 | 9/2012 | Boss et al. |
| 8,278,308 B2 | 10/2012 | Leone-Bay et al. |
| 8,293,869 B2 | 10/2012 | Bossard |
| 8,314,106 B2 * | 11/2012 | Kraft .................. C07D 241/08 514/255.02 |
| D671,842 S | 12/2012 | Bergey |
| D674,893 S | 1/2013 | Kinsey et al. |
| 8,372,804 B2 | 2/2013 | Richardson |
| 8,377,869 B2 | 2/2013 | Richardson |
| 8,389,470 B2 | 3/2013 | Steiner |
| 8,394,414 B2 | 3/2013 | Steiner et al. |
| 8,408,200 B2 | 4/2013 | Clark et al. |
| 8,420,604 B2 | 4/2013 | Hokenson |
| 8,424,518 B2 | 4/2013 | Smutney |
| 8,485,180 B2 | 7/2013 | Smutney et al. |
| 8,486,894 B2 | 7/2013 | Schteingart et al. |
| 8,499,757 B2 | 8/2013 | Smutney |
| 8,512,932 B2 | 8/2013 | Wilson et al. |
| 8,522,775 B2 | 9/2013 | Malhotra et al. |
| 8,536,131 B2 | 9/2013 | Schteingart et al. |
| 8,538,707 B2 | 9/2013 | Adamo et al. |
| 8,539,946 B2 | 9/2013 | Esteve et al. |
| 8,551,528 B2 | 10/2013 | Grant et al. |
| 8,563,101 B2 | 10/2013 | Spallek |
| 8,636,001 B2 | 1/2014 | Smutney |
| 8,642,548 B2 | 2/2014 | Richardson et al. |
| 8,671,937 B2 | 3/2014 | Steiner et al. |
| 8,677,992 B2 | 3/2014 | Villax |
| 8,763,606 B2 | 7/2014 | Mosier et al. |
| 8,778,403 B2 | 7/2014 | Grant et al. |
| 8,783,249 B2 | 7/2014 | Poole et al. |
| D711,740 S | 8/2014 | Lien |
| 8,808,786 B2 | 8/2014 | Jinks et al. |
| 8,820,324 B2 | 9/2014 | Smith et al. |
| 8,900,555 B2 | 12/2014 | Kuo et al. |
| 8,909,487 B2 | 12/2014 | Adamo et al. |
| 8,925,726 B2 | 1/2015 | Bergey |
| 9,041,925 B2 | 5/2015 | Adamo et al. |
| 9,138,407 B2 | 9/2015 | Caponetti et al. |
| D771,237 S | 11/2016 | Smutney et al. |
| 9,655,850 B2 * | 5/2017 | Kraft .................. A61K 9/1617 |
| 2001/0020147 A1 | 9/2001 | Staniforth et al. |
| 2001/0039442 A1 | 11/2001 | Gorge et al. |
| 2002/0000225 A1 | 1/2002 | Schuler et al. |
| 2002/0015737 A1 | 2/2002 | Shih et al. |
| 2002/0033177 A1 | 3/2002 | Ohki et al. |
| 2002/0052381 A1 | 5/2002 | Bar-Or et al. |
| 2002/0053344 A1 | 5/2002 | Davies et al. |
| 2002/0053347 A1 | 5/2002 | Ziaee |
| 2002/0065239 A1 | 5/2002 | Caplan et al. |
| 2002/0088462 A1 | 7/2002 | Genova et al. |
| 2002/0101590 A1 | 8/2002 | Shimaoka |
| 2002/0144680 A1 | 10/2002 | Nilsson et al. |
| 2002/0161001 A1 | 10/2002 | Kanstrup et al. |
| 2003/0000524 A1 | 1/2003 | Andersson et al. |
| 2003/0010794 A1 | 1/2003 | Herdtle et al. |
| 2003/0013641 A1 | 1/2003 | Steiner et al. |
| 2003/0017211 A1 | 1/2003 | Steiner |
| 2003/0053960 A1 | 3/2003 | Heijerman et al. |
| 2003/0064097 A1 | 4/2003 | Patel et al. |
| 2003/0068378 A1 | 4/2003 | Chen et al. |
| 2003/0099636 A1 | 5/2003 | Epshtein et al. |
| 2003/0136405 A1 | 7/2003 | Goede et al. |
| 2003/0168370 A1 | 9/2003 | Merboth et al. |
| 2003/0194420 A1 | 10/2003 | Holl et al. |
| 2003/0216542 A1 | 11/2003 | Patton et al. |
| 2003/0235538 A1 | 12/2003 | Zirenberg |
| 2004/0022861 A1 | 2/2004 | Williams et al. |
| 2004/0024180 A1 | 2/2004 | Drauz |
| 2004/0025875 A1 | 2/2004 | Reber et al. |
| 2004/0034014 A1 | 2/2004 | Kanstrup et al. |
| 2004/0038865 A1 | 2/2004 | Gelber et al. |
| 2004/0053819 A1 | 3/2004 | Dodd et al. |
| 2004/0062722 A1 | 4/2004 | Gonda et al. |
| 2004/0076588 A1 | 4/2004 | Batycky et al. |
| 2004/0077528 A1 | 4/2004 | Steiner et al. |
| 2004/0096403 A1 | 5/2004 | Steiner |
| 2004/0107963 A1 | 6/2004 | Finlay et al. |
| 2004/0121964 A1 | 6/2004 | Madar et al. |
| 2004/0138099 A1 | 7/2004 | Draeger |
| 2004/0151059 A1 | 8/2004 | Robert, II et al. |
| 2004/0151774 A1 | 8/2004 | Pauletti et al. |
| 2004/0157928 A1 | 8/2004 | Kim et al. |
| 2004/0163648 A1 | 8/2004 | Burton |
| 2004/0182387 A1 | 9/2004 | Steiner et al. |
| 2004/0187869 A1 | 9/2004 | Bjorndal et al. |
| 2004/0204439 A1 | 10/2004 | Staniforth et al. |
| 2004/0204440 A1 | 10/2004 | Staniforth et al. |
| 2004/0211419 A1 | 10/2004 | Eason et al. |
| 2004/0211420 A1 | 10/2004 | Minshull et al. |
| 2004/0234615 A1 | 11/2004 | Sabetsky |
| 2004/0234616 A1 | 11/2004 | Sabetsky |
| 2004/0235956 A1 | 11/2004 | Quay |
| 2004/0241232 A1 | 12/2004 | Brown et al. |
| 2004/0247628 A1 | 12/2004 | Lintz et al. |
| 2004/0250812 A1 | 12/2004 | Davies et al. |
| 2005/0000518 A1 | 1/2005 | Dunkley et al. |
| 2005/0003003 A1 | 1/2005 | Basu et al. |

(56) References Cited

U.S. PATENT DOCUMENTS

| | | |
|---|---|---|
| 2005/0039743 A1 | 2/2005 | Taylor |
| 2005/0043228 A1 | 2/2005 | DeFelippis et al. |
| 2005/0043247 A1 | 2/2005 | Trunk et al. |
| 2005/0056281 A1 | 3/2005 | Snow |
| 2005/0070469 A1 | 3/2005 | Bloom |
| 2005/0080000 A1 | 4/2005 | Thurow et al. |
| 2005/0119604 A1 | 6/2005 | Bonney et al. |
| 2005/0124644 A1 | 6/2005 | Nilsson et al. |
| 2005/0147581 A1 | 7/2005 | Zamiri et al. |
| 2005/0153874 A1 | 7/2005 | Cheatham et al. |
| 2005/0155601 A1 | 7/2005 | Steiner et al. |
| 2005/0183723 A1 | 8/2005 | Pinon et al. |
| 2005/0187749 A1 | 8/2005 | Singley |
| 2005/0203002 A1 | 9/2005 | Tzannis et al. |
| 2005/0214251 A1 | 9/2005 | Pohl et al. |
| 2005/0252508 A1 | 11/2005 | Koerner |
| 2005/0265927 A1 | 12/2005 | Lee |
| 2005/0274378 A1 | 12/2005 | Bonney et al. |
| 2006/0000469 A1 | 1/2006 | Tseng |
| 2006/0003316 A1 | 1/2006 | Simard et al. |
| 2006/0040953 A1 | 2/2006 | Leone-Bay et al. |
| 2006/0041133 A1 | 2/2006 | Stevenson et al. |
| 2006/0062740 A1 | 3/2006 | Rand |
| 2006/0099269 A1 | 5/2006 | Cheatham et al. |
| 2006/0102511 A1 | 5/2006 | Pasbrig et al. |
| 2006/0120969 A1 | 6/2006 | Nilsson et al. |
| 2006/0153778 A1 | 7/2006 | Gelber et al. |
| 2006/0160722 A1 | 7/2006 | Green et al. |
| 2006/0165756 A1 | 7/2006 | Catani et al. |
| 2006/0219242 A1 | 10/2006 | Zierenberg |
| 2006/0239933 A1 | 10/2006 | Nilsson et al. |
| 2006/0239934 A1 | 10/2006 | Cheatham et al. |
| 2006/0243275 A1 | 11/2006 | Ruckdeschel et al. |
| 2006/0249419 A1 | 11/2006 | Taylor et al. |
| 2006/0260777 A1 | 11/2006 | Rashba-Step et al. |
| 2006/0283758 A1 | 12/2006 | Pasbrig |
| 2007/0006876 A1 | 1/2007 | Finlay et al. |
| 2007/0017506 A1 | 1/2007 | Bell et al. |
| 2007/0020191 A1 | 1/2007 | Boss et al. |
| 2007/0027063 A1 | 2/2007 | Boss et al. |
| 2007/0044793 A1 | 3/2007 | Kleinstreuer et al. |
| 2007/0049576 A1 | 3/2007 | Barlow et al. |
| 2007/0059373 A1 | 3/2007 | Oberg |
| 2007/0059374 A1 | 3/2007 | Hokenson et al. |
| 2007/0074989 A1 | 4/2007 | Merboth et al. |
| 2007/0077219 A1 | 4/2007 | Fahl et al. |
| 2007/0086952 A1 | 4/2007 | Steiner |
| 2007/0099454 A1 | 5/2007 | Gordon |
| 2007/0125375 A1 | 6/2007 | Finlay et al. |
| 2007/0128193 A1 | 6/2007 | O'Neil et al. |
| 2007/0151562 A1 | 7/2007 | Jones |
| 2007/0160789 A1 | 7/2007 | Merical et al. |
| 2007/0175314 A1 | 8/2007 | Wanne |
| 2007/0190163 A1 | 8/2007 | Malakhov et al. |
| 2007/0191462 A1 | 8/2007 | Hettiarachchi |
| 2007/0196503 A1 | 8/2007 | Wilson et al. |
| 2007/0207958 A1 | 9/2007 | Bridon et al. |
| 2007/0225587 A1 | 9/2007 | Burnell et al. |
| 2007/0235029 A1 | 10/2007 | Zhu et al. |
| 2007/0240708 A1 | 10/2007 | Schuckmann |
| 2007/0272763 A1 | 11/2007 | Dunne et al. |
| 2007/0277820 A1 | 12/2007 | Crowder et al. |
| 2007/0277821 A1 | 12/2007 | Oliva et al. |
| 2007/0295332 A1 | 12/2007 | Ziegler |
| 2007/0299074 A1 | 12/2007 | Netz et al. |
| 2008/0008764 A1 | 1/2008 | Milstein |
| 2008/0015457 A1 | 1/2008 | Silva |
| 2008/0039368 A1 | 2/2008 | Steiner et al. |
| 2008/0039402 A1 | 2/2008 | Mossalayi et al. |
| 2008/0047550 A2 | 2/2008 | Steiner et al. |
| 2008/0066739 A1 | 3/2008 | LeMahieu et al. |
| 2008/0108554 A1 | 5/2008 | Jackson et al. |
| 2008/0108574 A1 | 5/2008 | Barlow et al. |
| 2008/0115785 A1 | 5/2008 | Eason et al. |
| 2008/0127970 A1 | 6/2008 | Steiner et al. |
| 2008/0127974 A1 | 6/2008 | Lastow |
| 2008/0129791 A1 | 6/2008 | King et al. |
| 2008/0168987 A1 | 7/2008 | Denny et al. |
| 2008/0190424 A1 | 8/2008 | Lucking et al. |
| 2008/0197044 A1 | 8/2008 | Hickey et al. |
| 2008/0216824 A1 | 9/2008 | Ooida |
| 2008/0217199 A1 | 9/2008 | Burress et al. |
| 2008/0255468 A1 | 10/2008 | Derchak et al. |
| 2008/0260838 A1 | 10/2008 | Hokenson et al. |
| 2008/0260840 A1 | 10/2008 | Alessi |
| 2008/0295833 A1 | 12/2008 | Rohrschneider et al. |
| 2008/0312155 A1 | 12/2008 | Kitada et al. |
| 2008/0314384 A1 | 12/2008 | Harris et al. |
| 2008/0319333 A1 | 12/2008 | Gavish et al. |
| 2009/0025720 A1 | 1/2009 | Chen |
| 2009/0068274 A1 | 3/2009 | Edwards et al. |
| 2009/0084379 A1 | 4/2009 | Goeckner et al. |
| 2009/0084380 A1 | 4/2009 | Gieschen et al. |
| 2009/0134051 A1 | 5/2009 | Rapp et al. |
| 2009/0149727 A1 | 6/2009 | Truitt et al. |
| 2009/0151720 A1 | 6/2009 | Inoue et al. |
| 2009/0178676 A1 | 7/2009 | Villax et al. |
| 2009/0205657 A1 | 8/2009 | Barney et al. |
| 2009/0209502 A1 | 8/2009 | Haeberlin et al. |
| 2009/0232891 A1 | 9/2009 | Gelber et al. |
| 2009/0241949 A1 | 10/2009 | Smutney |
| 2009/0250058 A1 | 10/2009 | Lastow |
| 2009/0258818 A1 | 10/2009 | Surolia et al. |
| 2009/0314291 A1 | 12/2009 | Anderson et al. |
| 2009/0314292 A1 | 12/2009 | Overfield |
| 2009/0320837 A1 | 12/2009 | Smith et al. |
| 2010/0012120 A1 | 1/2010 | Herder |
| 2010/0051027 A1 | 3/2010 | Remmelgas et al. |
| 2010/0065048 A1 | 3/2010 | Walz et al. |
| 2010/0086609 A1 | 4/2010 | Steiner et al. |
| 2010/0113363 A1 | 5/2010 | Holst et al. |
| 2010/0163042 A1 | 7/2010 | Bhowmick et al. |
| 2010/0180894 A1 | 7/2010 | Jones et al. |
| 2010/0181225 A1 | 7/2010 | Spallek et al. |
| 2010/0190701 A1 | 7/2010 | Day et al. |
| 2010/0193380 A1 | 8/2010 | Sullivan et al. |
| 2010/0197565 A1 | 8/2010 | Smutney et al. |
| 2010/0212667 A1 | 8/2010 | Smith et al. |
| 2010/0235116 A1 | 9/2010 | Adamo et al. |
| 2010/0238457 A1 | 9/2010 | Adamo et al. |
| 2010/0278924 A1 | 11/2010 | Oberg |
| 2010/0288276 A1 | 11/2010 | Ganderton et al. |
| 2010/0326438 A1 | 12/2010 | Dunne |
| 2011/0000482 A1 | 1/2011 | Gumaste et al. |
| 2011/0003004 A1 | 1/2011 | Hokenson |
| 2011/0011394 A1 | 1/2011 | Edwards et al. |
| 2011/0023876 A1 | 2/2011 | Vehring et al. |
| 2011/0061653 A1 | 3/2011 | Schuckmann |
| 2011/0083667 A1 | 4/2011 | Briant |
| 2011/0155129 A1 | 6/2011 | Stedman et al. |
| 2011/0158935 A1 | 6/2011 | Kraft |
| 2011/0183901 A1 | 7/2011 | Cheatham |
| 2012/0014999 A1 | 1/2012 | Grant et al. |
| 2012/0040899 A1 | 2/2012 | Costello |
| 2012/0071510 A1 | 3/2012 | Leone-Bay et al. |
| 2012/0094905 A1 | 4/2012 | Costello |
| 2012/0115777 A1 | 5/2012 | Richardson |
| 2012/0122775 A1 | 5/2012 | Boss et al. |
| 2012/0160241 A1 | 6/2012 | Oliva |
| 2012/0164186 A1 | 6/2012 | Grant et al. |
| 2012/0178935 A1 | 7/2012 | Stevenson |
| 2012/0192865 A1 | 8/2012 | Steiner et al. |
| 2012/0207913 A1 | 8/2012 | Smyth |
| 2012/0240929 A1 | 9/2012 | Steiner et al. |
| 2012/0247235 A1 | 10/2012 | Adamo et al. |
| 2012/0247465 A1 | 10/2012 | Wachtel |
| 2012/0328676 A1 | 12/2012 | Leone-Bay et al. |
| 2013/0012710 A1 | 1/2013 | Freeman et al. |
| 2013/0053309 A1 | 2/2013 | Kraft |
| 2013/0104887 A1 | 5/2013 | Smutney et al. |
| 2013/0118491 A1 | 5/2013 | Richardson et al. |
| 2013/0125886 A1 | 5/2013 | Richardson et al. |
| 2013/0143801 A1 | 6/2013 | Steiner et al. |
| 2013/0189365 A1 | 7/2013 | Hokenson |

(56) References Cited

U.S. PATENT DOCUMENTS

| | | |
|---|---|---|
| 2013/0199527 A1 | 8/2013 | Smutney et al. |
| 2013/0243828 A1 | 9/2013 | Lipp et al. |
| 2013/0289278 A1 | 10/2013 | Kraft |
| 2013/0291866 A1 | 11/2013 | Smutney |
| 2013/0291867 A1 | 11/2013 | Smutney |
| 2013/0303445 A1 | 11/2013 | Wilson et al. |
| 2013/0338065 A1 | 12/2013 | Smutney |
| 2014/0007873 A1 | 1/2014 | Smutney |
| 2014/0014106 A1 | 1/2014 | Smutney |
| 2014/0083421 A1 | 3/2014 | Smutney |
| 2014/0096771 A1 | 4/2014 | Remmelgas et al. |
| 2014/0100158 A1 | 4/2014 | Richardson et al. |
| 2014/0187490 A1 | 7/2014 | Richardson et al. |
| 2014/0199398 A1 | 7/2014 | Grant et al. |
| 2014/0227359 A1 | 8/2014 | Leone-Bay et al. |
| 2014/0243530 A1 | 8/2014 | Stevenson et al. |
| 2014/0271888 A1 | 9/2014 | Grant et al. |
| 2014/0290654 A1 | 10/2014 | Poole et al. |
| 2014/0302151 A1 | 10/2014 | Leone-Bay et al. |
| 2014/0308358 A1 | 10/2014 | Oberg et al. |
| 2014/0315953 A1 | 10/2014 | Leone-Bay et al. |
| 2015/0031609 A1 | 1/2015 | Steiner et al. |
| 2015/0045295 A1 | 2/2015 | Smutney et al. |
| 2015/0052977 A1 | 2/2015 | Adamo et al. |
| 2015/0065422 A1 | 3/2015 | Kraft |
| 2015/0080298 A1 | 3/2015 | Costello et al. |
| 2015/0108023 A1 | 4/2015 | Bergey |
| 2015/0122258 A1 | 5/2015 | Steiner et al. |
| 2015/0150980 A1 | 6/2015 | Leone-Bay et al. |
| 2015/0174210 A1 | 6/2015 | Boss et al. |
| 2015/0196724 A1 | 7/2015 | Adamo et al. |
| 2015/0226656 A1 | 8/2015 | Adamo et al. |
| 2015/0231067 A1 | 8/2015 | Mann |
| 2015/0246188 A1 | 9/2015 | Steiner et al. |
| 2015/0283069 A1 | 10/2015 | Smutney et al. |
| 2015/0283213 A1 | 10/2015 | Costello et al. |
| 2015/0290132 A1 | 10/2015 | Gelber et al. |
| 2015/0359744 A1 | 12/2015 | Hokenson et al. |
| 2016/0008557 A1 | 1/2016 | Smutney et al. |
| 2016/0031833 A1 | 2/2016 | Wilson et al. |
| 2016/0067183 A1 | 3/2016 | Kraft |
| 2016/0095990 A1 | 4/2016 | Smutney et al. |
| 2016/0101049 A1 | 4/2016 | Wilson et al. |
| 2016/0151287 A1 | 6/2016 | Oberg et al. |
| 2016/0158156 A1 | 6/2016 | Fabio et al. |
| 2016/0175079 A1 | 6/2016 | Adamo et al. |
| 2016/0193432 A1 | 7/2016 | Harris et al. |
| 2016/0221967 A1 | 8/2016 | Stevenson et al. |
| 2016/0228659 A1 | 8/2016 | Smutney et al. |
| 2016/0243322 A1 | 8/2016 | Smutney et al. |
| 2016/0250297 A1 | 9/2016 | Leone-Bay et al. |
| 2016/0256640 A1 | 9/2016 | Overfield et al. |
| 2016/0287820 A1 | 10/2016 | Smutney et al. |
| 2016/0346212 A1 | 12/2016 | Hokenson et al. |
| 2016/0346394 A1 | 12/2016 | Grant et al. |
| 2017/0087217 A1 | 3/2017 | Cheatham et al. |
| 2017/0143804 A1 | 5/2017 | Boss et al. |
| 2017/0189395 A1 | 7/2017 | Grant et al. |
| 2017/0189492 A1 | 7/2017 | Boss et al. |
| 2017/0209525 A1 | 7/2017 | Leone-Bay et al. |
| 2017/0216538 A1 | 8/2017 | Kinsey et al. |
| 2017/0304404 A1* | 10/2017 | Costello ............... A61K 47/26 |

FOREIGN PATENT DOCUMENTS

| | | |
|---|---|---|
| CN | 101290219 A | 10/2008 |
| CN | 101851213 | 10/2010 |
| CN | 102436238 A | 5/2012 |
| DE | 2840442 C2 | 2/1982 |
| DE | 3639836 A1 | 6/1988 |
| DE | 19519840 A1 | 12/1996 |
| EP | 69715 | 1/1983 |
| EP | 122036 | 10/1984 |
| EP | 143524 | 6/1985 |
| EP | 180543 | 5/1986 |
| EP | 220958 | 5/1987 |
| EP | 237507 | 8/1987 |
| EP | 257915 | 2/1988 |
| EP | 308637 A1 | 3/1989 |
| EP | 360340 | 3/1990 |
| EP | 364235 | 4/1990 |
| EP | 387222 A | 9/1990 |
| EP | 388621 A | 9/1990 |
| EP | 606486 | 12/1993 |
| EP | 581473 A1 | 2/1994 |
| EP | 655237 | 5/1995 |
| EP | 666085 A1 | 8/1995 |
| EP | 748213 | 12/1996 |
| EP | 558879 B1 | 5/1997 |
| EP | 844007 | 12/1998 |
| EP | 1060741 A1 | 12/2000 |
| EP | 1114644 | 7/2001 |
| EP | 0837710 B1 | 11/2001 |
| EP | 640354 B1 | 12/2001 |
| EP | 1348428 A1 | 10/2003 |
| EP | 1364967 | 11/2003 |
| EP | 825885 B1 | 3/2004 |
| EP | 96911738 | 6/2004 |
| EP | 1598066 | 11/2005 |
| EP | 833652 B1 | 2/2008 |
| EP | 1923087 A2 | 5/2008 |
| EP | 2060268 A1 | 5/2009 |
| EP | 2314298 A1 | 4/2011 |
| GB | 475440 A | 11/1937 |
| GB | 716815 | 10/1954 |
| GB | 2072536 A | 10/1981 |
| GB | 2148841 A | 6/1985 |
| GB | 2240337 | 7/1991 |
| GB | 2253200 A | 9/1992 |
| GB | 2262452 | 6/1993 |
| GB | 2398065 A | 8/2004 |
| JP | S55-156085 U | 11/1980 |
| JP | 63-020301 | 1/1988 |
| JP | 2115154 A | 4/1990 |
| JP | 2-149545 | 2/1992 |
| JP | H07-041428 | 2/1995 |
| JP | 09-208485 | 8/1997 |
| JP | 10234827 A | 9/1998 |
| JP | 2002322294 | 11/2002 |
| JP | 2003-503420 | 1/2003 |
| JP | 2004-121061 | 4/2004 |
| JP | 2006-280620 A | 10/2006 |
| JP | 2007-061281 | 3/2007 |
| TW | 200505517 A | 2/2005 |
| WO | 1990/013285 | 11/1990 |
| WO | 1991/004011 | 4/1991 |
| WO | 1991/006287 | 5/1991 |
| WO | 1991/016038 | 10/1991 |
| WO | 1991/016882 | 11/1991 |
| WO | 1991/019524 | 12/1991 |
| WO | 1992/004069 | 3/1992 |
| WO | 1992/008509 | 5/1992 |
| WO | 1993/002712 | 2/1993 |
| WO | 1993/014110 | 7/1993 |
| WO | 1993/017728 | 9/1993 |
| WO | 1993/018754 A1 | 9/1993 |
| WO | 1994/000291 | 1/1994 |
| WO | 1994/008552 | 4/1994 |
| WO | 1994/008599 | 4/1994 |
| WO | 1994/019041 | 9/1994 |
| WO | 1994/023702 | 10/1994 |
| WO | 1994/025005 A1 | 11/1994 |
| WO | 1995/000127 A1 | 1/1995 |
| WO | 1995/005208 | 2/1995 |
| WO | 1995/011666 | 5/1995 |
| WO | 1995/024183 A1 | 9/1995 |
| WO | 1995/031979 | 11/1995 |
| WO | 1995/034294 | 12/1995 |
| WO | 1996/001105 | 1/1996 |
| WO | 1996/005810 | 2/1996 |
| WO | 1996/013250 | 5/1996 |
| WO | 1996/022802 A | 8/1996 |
| WO | 1996/027386 A1 | 9/1996 |
| WO | 1996/032149 | 10/1996 |

(56) References Cited

FOREIGN PATENT DOCUMENTS

| | | |
|---|---|---|
| WO | 1996/036314 | 11/1996 |
| WO | 1996/036317 A1 | 11/1996 |
| WO | 1996/040206 A1 | 12/1996 |
| WO | 1997/001365 | 1/1997 |
| WO | 1997/004747 | 2/1997 |
| WO | 1997/025086 A2 | 7/1997 |
| WO | 1997/030743 | 8/1997 |
| WO | 1997/035562 A1 | 10/1997 |
| WO | 1997/046206 | 12/1997 |
| WO | 1997/049386 | 12/1997 |
| WO | 1998/026827 A1 | 6/1998 |
| WO | 1998/034661 A1 | 8/1998 |
| WO | 1998/039043 | 9/1998 |
| WO | 1998/041255 A2 | 9/1998 |
| WO | 1998/043615 | 10/1998 |
| WO | 1999/014239 A1 | 3/1999 |
| WO | 1999/018939 A1 | 4/1999 |
| WO | 1999/032510 A1 | 7/1999 |
| WO | 1999/033862 | 7/1999 |
| WO | 1999/052506 | 10/1999 |
| WO | 2000/12116 | 3/2000 |
| WO | 2000/033811 A2 | 6/2000 |
| WO | 2000/059476 A1 | 10/2000 |
| WO | 2000/071154 A2 | 11/2000 |
| WO | 2001/000654 | 1/2001 |
| WO | 2001/081321 A | 1/2001 |
| WO | 2001/049274 A2 | 7/2001 |
| WO | 2001/051071 | 7/2001 |
| WO | 2001/052813 A1 | 7/2001 |
| WO | 2001/066064 | 9/2001 |
| WO | 2001/068169 | 9/2001 |
| WO | 2001/097886 A1 | 12/2001 |
| WO | 2001/007107 | 2/2002 |
| WO | 2002/011676 | 2/2002 |
| WO | 2002/012201 A1 | 2/2002 |
| WO | 2002/047659 A2 | 6/2002 |
| WO | 2002/058735 | 8/2002 |
| WO | 2002/059574 A1 | 8/2002 |
| WO | 2002/067995 A1 | 9/2002 |
| WO | 2002/085281 | 10/2002 |
| WO | 2002/098348 | 12/2002 |
| WO | 2002/102444 | 12/2002 |
| WO | 2003/000202 | 1/2003 |
| WO | 2003/015857 A1 | 2/2003 |
| WO | 2003/018059 A2 | 3/2003 |
| WO | 2003/022304 A1 | 3/2003 |
| WO | 2003/055547 A1 | 7/2003 |
| WO | 2003/057170 | 7/2003 |
| WO | 2003/061578 A2 | 7/2003 |
| WO | 2003/072195 A2 | 9/2003 |
| WO | 2003/080149 A2 | 10/2003 |
| WO | 2003/084502 A1 | 10/2003 |
| WO | 2003/086345 | 10/2003 |
| WO | 2003/094951 | 11/2003 |
| WO | 2004/012672 | 2/2004 |
| WO | 2004/012720 | 2/2004 |
| WO | 2004/033010 | 4/2004 |
| WO | 2004/035121 | 4/2004 |
| WO | 2004/041338 | 5/2004 |
| WO | 2004/050152 | 6/2004 |
| WO | 2004/054647 A1 | 7/2004 |
| WO | 2004/056314 | 7/2004 |
| WO | 2004/060458 | 7/2004 |
| WO | 2004/064862 | 8/2004 |
| WO | 2004/075919 | 9/2004 |
| WO | 2004/080401 | 9/2004 |
| WO | 2004/080482 | 9/2004 |
| WO | 2004/103304 A2 | 12/2004 |
| WO | 2005/002654 A2 | 1/2005 |
| WO | 2005/020964 | 3/2005 |
| WO | 2005/023348 A | 3/2005 |
| WO | 2005/028699 A1 | 3/2005 |
| WO | 2005/067964 | 7/2005 |
| WO | 2005/081977 A2 | 9/2005 |
| WO | 2005/089722 | 9/2005 |
| WO | 2005/089843 | 9/2005 |
| WO | 2005/102428 A1 | 11/2005 |
| WO | 2005/102429 | 11/2005 |
| WO | 2005/113042 A1 | 12/2005 |
| WO | 2005/113043 | 12/2005 |
| WO | 2005/120616 | 12/2005 |
| WO | 2006/010248 | 2/2006 |
| WO | 2006/017688 A2 | 2/2006 |
| WO | 2006/023849 | 3/2006 |
| WO | 2006/023943 | 3/2006 |
| WO | 2006/023944 | 3/2006 |
| WO | 2006/037636 | 4/2006 |
| WO | 2006/059939 | 6/2006 |
| WO | 2006/061637 A2 | 6/2006 |
| WO | 2006/086107 A2 | 8/2006 |
| WO | 2006/090149 | 8/2006 |
| WO | 2006/105501 | 10/2006 |
| WO | 2007/007110 A1 | 1/2007 |
| WO | 2007/016600 A2 | 2/2007 |
| WO | 2007/019229 | 2/2007 |
| WO | 2007/024953 A1 | 3/2007 |
| WO | 2007/030706 | 3/2007 |
| WO | 2007/033316 | 3/2007 |
| WO | 2007/033372 A2 | 3/2007 |
| WO | 2007/042822 | 4/2007 |
| WO | 2007/068896 | 6/2007 |
| WO | 2007/075534 A2 | 7/2007 |
| WO | 2007/093310 | 8/2007 |
| WO | 2007/098500 | 8/2007 |
| WO | 2007/100535 | 9/2007 |
| WO | 2007/118342 | 10/2007 |
| WO | 2007/118343 A1 | 10/2007 |
| WO | 2007/121411 | 10/2007 |
| WO | 2007/132217 | 11/2007 |
| WO | 2007/144607 | 12/2007 |
| WO | 2007/144614 | 12/2007 |
| WO | 2008/001744 | 1/2008 |
| WO | 2008/008021 | 1/2008 |
| WO | 2008/014613 A1 | 2/2008 |
| WO | 2008/020217 | 2/2008 |
| WO | 2008/060484 A2 | 5/2008 |
| WO | 2008/092864 | 8/2008 |
| WO | 2008/110809 | 9/2008 |
| WO | 2009/005546 A1 | 1/2009 |
| WO | 2009/008001 A2 | 1/2009 |
| WO | 2009/009013 A2 | 1/2009 |
| WO | 2009/047281 A1 | 4/2009 |
| WO | 2009/055030 | 4/2009 |
| WO | 2009/055740 | 4/2009 |
| WO | 2009/055742 | 4/2009 |
| WO | 2009/095684 A1 | 8/2009 |
| WO | 2009/121020 A1 | 10/2009 |
| WO | 2009/140587 A1 | 11/2009 |
| WO | 2009/152477 A2 | 12/2009 |
| WO | 2009/155581 A1 | 12/2009 |
| WO | 2010/021879 A2 | 2/2010 |
| WO | 2010/078373 A1 | 7/2010 |
| WO | 2010/080964 | 7/2010 |
| WO | 2010/102148 | 9/2010 |
| WO | 2010/105094 A1 | 9/2010 |
| WO | 2010/108046 A1 | 9/2010 |
| WO | 2010/125103 A1 | 11/2010 |
| WO | 2010/144785 A2 | 12/2010 |
| WO | 2010/144789 | 12/2010 |
| WO | 2011/017554 A2 | 2/2011 |
| WO | 2011/056889 A1 | 5/2011 |
| WO | 2011/082328 A1 | 7/2011 |
| WO | 2011/163272 | 12/2011 |
| WO | 2012/064892 A1 | 5/2012 |
| WO | 2012/135765 | 10/2012 |
| WO | 2012/174472 A1 | 12/2012 |
| WO | 2012/174556 A1 | 12/2012 |
| WO | 2013/016754 A1 | 2/2013 |
| WO | 2013/063160 A1 | 5/2013 |
| WO | 2014/012069 A2 | 1/2014 |
| WO | 2014/036323 A1 | 3/2014 |
| WO | 2014/066856 A1 | 5/2014 |
| WO | 2014/144895 A1 | 9/2014 |
| WO | 2015/010092 A1 | 1/2015 |

(56) References Cited

FOREIGN PATENT DOCUMENTS

| WO | 2015/021064 A1 | 2/2015 |
|---|---|---|
| WO | 2015/063100 A1 | 5/2015 |
| WO | 2015/148905 A1 | 10/2015 |
| WO | 2017/132601 | 8/2017 |

OTHER PUBLICATIONS

Chelikani et al., Intravenous infusion of glucagon-like peptide-1 potently inhibits food intake, sham feeding, and gastric emptying in rats. Am J Physiol. Regul. Integr. Comp. Physiol., 288(6):R1695-706, 2005.
Chemical Abstracts, vol. No. 114(22), Abstract No. 214519x (1990).
Chemicaland21.com. Solvents. Dec. 12, 2008. Available from: <http://web.archive.org/web20081212035748/http://www.chemicalland21.com/info/SOLVENTS.htm.
Chow et al., Particle Engineering for Pulmonary Drug Delivery. Pharmaceutical Research, vol. 24, No. 3, pp. 411-437 (2007).
Clee et al. Nature Genetics 38:688-693, 2006.
Cobble "Initiating and Intensifying Insulin Therapy for Type 2 Diabetes: Why, When, and How." Am J Ther. Jan. 8, 2009.
Coffey et al. "Valuing heath-related quality of life in diabetes." Diabetes Care 25:2238, 2002.
Colagiuri et al., Are lower fasting plasma glucose levels at diagnosis of type 2 diabetes associated with improved outcomes? Diabetes Care, vol. 25, pp. 1410-1417 (2002).
Combettes and Kargar, C, Newly Approved and Promising Antidiabetic Agents. Therapie, Jul.-Aug. 2007, 62 (4):293-310.
Coors et al., Polysorbate 80 in medical products and nonimmunologic anaphylactoid reactions. Ann. Allergy Astha Immunol., 95(6): 593-599 (2005).
Costello et al., "Zinc inhibition of mitochondrial aconitase and its importance in citrate metabolism in prostate epithelial cells", Journ. Biol. Chem. 272(46):28875-28881 (1997).
Cricket TM Single-Use Inhalers [on-line]. MannKind Technologies Website, posted in 2011, [retrieved on Jul. 30, 2012]. Retrieved from the Internet. <URL:mannkindtechnologies,com/DeviceTechnology/CricketSingleUseInhalers.aspx>.
Crosby, J. "Dog Normals", <http://vetmedicine.about.com/od/diseasesconditionsfaqs/tp/TP_dogfacts.htm>, copyright 2013.
Cruetzfeldt et al. "Glucagonostatic actions and reduction of fasting hyerglycemia by exogenous glucagon-like peptide i(7-36) amide in type 1 diabetic patients." Diabetes Care 19:580, 1996.
D'Alessio et al., Elimination of the action of glucagon-like peptide 1 causes an impairment of glucose tolerance after nutrient ingestion by healthy baboons. J. Clin. Invest., 97:133-38 (1996).
Database adisinsight, "Gucagon-like peptide-1 inhalation-MannKind Corporation", Database accession No. 2009:1048 Abstract.
Davis "Postprandial Physiology and the Pathogenesis of Type 2 Diabetes Mellitus." Insulin, vol. 3, Apr. 1, 2008, pp. 132-140.
De Heer et al. "Sulfonylurea compounds uncouple the glucose dependence of the insulinotropic effect of glucagon-like peptide-1." Diabetes 56:438, 2007.
Deacon "Therapeutic strategies based on glucagon-like peptide 1." Diabetes. Sep;53(9):2181-9, 2004.
Deacon et al., "Glucagon-like peptide 1 undergoes differential tissue-specific metabolism in the anesthetized pig", Am. J. Physiol. 271 (Endocrino. Metab. 34): E458-E464, 1996.
Decode study group. "Glucose tolerance and mortality: comparison of WHO and American Diabetes Association diagnostic criteria." Lancet. Aug. 21, 1999;354(9179):617-21.
DedicatedPhase, "Preclinical Trials and Research", <http://www.dedicatedphase1.com/preclinical-research.html>, copyright 2006-2011, p. 1.
Definition of analog from http://cancerweb.ncl.ac.uk/omd/about.html, pp. 1-5. Accessed by Examiner on Jul. 7, 2005 and cited in Office Action dated Jul. 26, 2013 in U.S. Appl. No. 12/830,557.
Del Prato S "Unlocking the opportunity of tight glycemic control" Diabetes Obesity and Metabolism 7:S1-S4, 2005.
Delgado-Aros et al. "Effect of GLP-1 on gastric volume, emptying, maximum volume ingested and postprandial symptoms in humans." Am J Physiol Gastrointest Liver Physiol 282:G424, 2002.
Diabetes: Counting Carbs if You Use Insulin, WedMD, http://diabetes.webmd.com/carbohydrate-counting-for-people-who-use-insulin#m Oct. 1, 2010.
Diez et al. "Inhaled insulin—a new therapeutic option in the treatment of diabetes mellitus" Expert Opin. Pharmacother., 2003, 4, 191-200.
Dorwald, F.A. Side reactions in organic synthesis. Wiley, (2005).
Doyle et al. "Glucagon-like peptide-1." Recent Prog Horm Res. 2001;56:377-99.
Dreamboat TM Reusable Inhalers [on-line]. MannKind Technologies Website, posted in 2011, Retrieved from the Internet: <URL: mannkindtechnologies.com/Device Technology/Dream Boat Reuseable Inhalers.aspx>.
Drucker "Development of glucagon-like peptide-1-based pharmaceuticals as therapeutic agents for the treatment of diabetes." Curr Pharma Design 7:1399, 2001.
Drucker et al., "The incretin system:glucagon-like peptide-1 receptor agonists and dipeptidyl peptidase-4 inhibitors in type 2 diabetes", www.thelancet.com, vol. 368, pp. 1696-1705, Nov. 11, 2006.
Drug Delivery, Easing the drug delivery route, Jun. 2006, Pharmaceutical & Medical Packaging News, Canon Communications.
Dungan et al., Glucagon-like peptide 1-based therapies for type 2 diabetes: a focus on exntadtide. Clinical Diabetes, 23: 56-62 (2005).
Dunn, "Zinc-ligand interactions modulate assembly and stability of the insulin hexamer", Biometals, 18(4):295-303 (2005).
Edelman "Type II Diabetes Mellitus." Adv Int Med, 43:449-500, 1998.
Edited by Fukushima, Masanori, "Arterial Sclerosis," Merck Manual 17th, Japanese Edition, NIKKEI BP Corp., p. 1659-1663, 1999.
Edwards CMB et al. "Cardiovascular and pancreatic endocrine response to glucagon-like peptide-1(7-36) amide in the conscious calf." Exp Physiol 82:709, 1997.
Edwards CMB et al. "Subcutaneous glucagon-like peptide-1(7-36) amide is insulinotropic and can cause hypoglycaemia in fasted healthy subjects." Clinical Science 96:719, 1998.
Edwards et al., Recent advances in pulmonary drug delivery using large, porous inhaled particles. Journal of Applied Physiology, pp. 379-385 (1998).
Eggers et al., Molecular confinement influences protein structure and enhances thermal protein stability. Protein Sci., 10:250-261 (2001).
Ehlers et al. "Recombinant glucagon-like peptide-1 (7-36 amide) lowers fasting serum glucose in a broad spectrum of patients with type 2 diabetes." Horm Metab Res 35:611, 2003.
Eissele et al., Rat gastric somatostatin and gastrin relase: interactions of exendin-4 and truncated glucagon-like peptide-1 (GLP-1) amide. Life Sci., 55(8):629-634 (1994).
Elliot et al., Parenteral absorption of insulin from the lung in diabetic children. Austr. Paediatr. J. 23: 293-297 (1987).
Elrick et al. "Plasma insulin response to oral and intravenous glucose administration." J Clin Endocr 24:1076, 1964.
Engelgau MM "Screening for type 2 diabetes." Diabetes Care 23:1563-1580, 2000.
Engwerda et al., Improved pharmackinetic and pharmacodynamic profile of rapid-acting insulin using needle-free jet injection technology. Diabetes Care, vol. 34, Aug. 2011, pp. 1804-1808.
Erlanger et al., Phosphorous pentoxide as a reagent in peptide synthesis. College of Physicians and Surgeons—Columbia Univeristy, vol. 26, pp. 2534-2536 (1960).
Exubera indications, dosage, storage, stability. Http://www.rxlist.com/cgi/generic4/exubera_ids.htm, 2008.
"An inhaled insulin formulation (Technosphere Insulin) effectively improves glycaemic control in patients with type 2 diabetes mellitus." Inpharma Weekly, vol. 1522, Jan. 28, 2006, p. 8.
ACTOS Product Insert. Aug. 2008.
Adjusting Mealtime Insulin Doses. BD Diabetes. http://www.bd.com/diabetes/page.aspx?cat=7001&id=7280 (2014).
Ahren "GLP-1 and extra-islet effects." Horm. Med Res 36:842, 2004.

(56) References Cited

OTHER PUBLICATIONS

Ahren B et al. "Characterization of GLP-1 effects on b-cell function after meal ingestion in humans." Diabetes Care 26:2860, 2003.
Ahren B., Glucagon-like peptide-1 (GLP-1): a gut hormone of potential interest in the treatment of diabetes. BioEssays, V. 20, pp. 642-651 (1998).
Akerlund et al., Diketopiperazine-based polymers from common acids. Journal of Applied Polymer Science (2000), 78(12), 2213-2218.
Alabraba et al. Diabetes Technology & Therapeutics. Jul. 2009, 11(7): 427-430.
Alcohols limited. Alcohol speciality solvents—Go green! Jul. 24, 2010. Available from: <http://webarchive.org/web/20100724193725/http://www.alcohols.co.uk/speciality_solvents.php>.
Aljada et al. "Insulin inhibits the pro-inflammatroy transcription factor early growth response gene-1 (Egr)-1 expression in mononuclear cells (MNC) and reduces plasma tissue factor (TF) and plasminogen activator inhibitor-1 (PAI-1) concentrations." The Journal of Clinical Endocrinology and Metabolism, vol. 87, No. 3, p. 1419-1422, 2002.
Al-Showair et al., Can all patients with COPD use the correct inhalation flow with all inhalers and does training help? Respiratory Medicine, vol. 101, No. 11, p. 2395-2401 (2007).
American Diabetes Association, "Standards of medical care in diabetes—2009", Diabetes Care, Jan. 2009, 32 Suppl 1: S13-61.
Amin N, Boss AH, Petrucci R, et al. Pulmonary functions (over 2 years) in diabetic subjects treated with AFRESA® or usual antidiabetic treatment ADA 2009; Poster 570.
Amin N, et al. Long-term sustained safety and efficacy of continued use of Technosphere insulin in subjects with type 2 diabetes. Abstract—Oral Presentation 215, 48th EASD Annual Meeting, Sep. 29-Oct. 2, 2009, Vienna Austria.
Amin N, Marino MT, Cassidy JP, et al. Acute pulmonary effects of Technosphere® insulin inhalation powder administered using a Gen2B inhaler compared to MedTone® C inhaler. Diabetes Technology Meeting 2010; poster.
Amin N, Phillips M, Boss AH, et al. Pulmonary functions (over 2 years) in diabetic patients treated with Technosphere® insulin (TI) or usual antidiabetic treatment. Third International Conference on Advanced Technologies and Treatments for Diabetes. 2010; Poster 290.
Angelo et al., Technosphere Insulin: Defining the Role of Technosphere Particles at the Celluar Level. J. Diabetes Sci. Technol., vol. 3, Issue 3, pp. 545-554 (2009).
Angelo et al. Technosphere® insulin inhalation powder: Defining the mechanism of action. ADA 2008; 57: Poster 428-P.
Antosiewiez et al., Prediction of pH-dependent properties of proteins. J Mol. Biol., 238:415-436 (1994).
Arakawa et al., Preferential interactions determine protein solubility in three-component solutions: the MgCl2 system. Biochemistry, 29:1914-1923 (1990).
Ashwell et al. "Twice-daily compared with once-daily insulin glargine in people with Type 1 diabetes using meal-time insulin aspart." 2006 Diabetes UK, Diabetic Medicine, 23, 879-886.
Ashwell et al., "Optimal timing of injection of once-daily insulin gargine in people with Type 1 diabetes using insulin lispro at meal-times" 2005 Diabetes UK, Diabetic Medicine, 23, 46-52.
Atherton, F. et al. "Synthesis of 2(R)-A3(S)-Acylamino-2-OXO-1-Azetidinyloxy U-Acetic Acids." Tetrahedron, vol. 40, No. 6, Jan. 1, 1984, pp. 1039-1046.
Avandia Product Insert, Oct. 2008.
Baggio et al. "A recombinant human glucagon-like peptide (GLP)-1-albumin protein (Albugon) mimics peptidergic activation of GLP-1 receptor-dependent pathways coupled with satiety, gastrointestinal motility, and glucose homeostatsis." Diabetes 53:2492, 2004.
Baggio et al. "Glucagon-like peptide-1, but not glucose-dependent insulinotropic peptide, regulates fasting glycemia and noneneteral glucose clearance in mice." Endocrinology 141:3703, 2000.
Baggio et al. "Harnessing the therapeutic potential of glucagon-like peptide-1." Treat Endocrinol 1:117, 2002.

Drucker et al., Minireview: The glucagon-like peptides. Endocrinology, vol. 142, No. 2, pp. 521-527 (2001).
Balkan B et al. "Portal GLP-1 administration in rats augments the insulin response to glucose via neuronal mechanisms." Am J. Physiol Regulatory Integrative Comp Physiol 279:R1449, 2000.
Barnett AH et al. "An open, randomized, parallel-group study to compare the efficacy and safety profile of inhaled human insulin (Exubera) with glibenclamide as adjunctive therapy in patients with Type 2 diabetes poorly controlled on metformin." Diabetes Care 29(8):1818-1825, 2006.
Barnett et al., An open, randomized, parallel-group study to compare the efficacy and safety profile of inhaled human insulin (Exubera) with metformin as adjunctive therapy in patients with type 2 diabetes poorly controlled on a sulfonylurea. Diabetes Care, 29(6): 1282-1287 (2006).
Barragan et al. "Changes in arterial blood pressure and heart rate induced by glucagon-like peptide-1-(7-36) amide in rats." Am J. Physiol 266 (Endocrinol Metab 29):E459, 1994.
Basu A et al. "Effects of a change in the pattern of insulin delivery on carbohydrate tolerance in diabetic and nondiabetic humans in the presence of differing degrees of insulin resistance." J Clin Invest 97:2351-2361, 1996.
Bauer et al., "Assessment o beta-adrenergic receptor blockade after isamoitane, a 5-HT1-receptor active compound, in healthy volunteer", Clin. Pharmacol Ther 53:76-83 (1993).
Bauer et al., "Pharmacodynamic effects of inhaled dry powder formulations of fenterol and colforsin in asthma", Clin Pharmacol Ther 53:76-83, 1993.
Baughman R, Cassidy J, Amin N, et al. A phase I, open-label study of the effect of albuterol or fluticasone on the pharmacokinetics of inhaled Technosphere® insulin inhalation powder in healty subjects. ADA 2010; Poster 528.
Baughman R, Cassidy J, Levy B, et al. Technosphere® insulin inhalation powder pharmacokinetics unchanged in subjects who smoke. Diabetes 2008; 57: A128.
Baughman R, Haworth P, Litwin J, et al. No cardiac effects found with therapeutic and suprtherapeutic doses of Technosphere® inhalation powder: results from a thorough QTc clinical study. ADA 2011. Poster 933-P.
Baughman, RA, Evans, SH, Boss, AH, et al. Technosphere insulin does not affect pulmonary function in a 6 month study of patients with type 2 diabetes. Diabetologia 2006;49:177-118.
Bayés M et al. "Gateways to clinical trials" Methods Find Exp Clin Pharmacol 24:431-455, 2002.
Beers et al., Section 2—Chapter 13—Diabetes Mellitus, The Merck Manual of Diagnosis and Therapy, Merck Research Laboratories, pp. 165-177 (1999).
Behme et al. "Glucagon-like peptide-1 improved glycemic control in type 1 diabetes." BMC Endocrine Disorders 3:3, 2003.
Bellary et al. "Inhaled insulin:new technology, new possibilities." Int J Clin Pract 60:728, 2006.
Belmin J et al. "Novel drug delivery systems for insulin. Clinical potential for use in the elderly." Drugs Aging 20:303-12, 2003.
Benita, Charaterization of Drug-Loaded Poly(d,l-lactide) Microspheres. J. Pharm. Sci., 73: 1721-1724 (1984).
Benito E et al. "Glucagon-like peptide-1-(7-36) amide increases pulmonary surfactant secretion through a cyclic adenosine 3',5'-monophosphate-dependent protein kinase mechanism in rat type II pneumocytes." Endocrinology 139:2363, 1998.
Bensch et al., Absorption of intact protein molecules across the pulmonary air-tissue barrier, Science 156: 1204-1206 (1967).
Berge et al., "Pharmaceutical Salts", J. Pharmaceutical Sciences, Review Article, 66(1):1-19 (1977).
Bergenstal R, Kapsner P, Rendell M, et al., Comparative efficacy and safety of AFRESA® and a rapid-acting analog both given with glargine in subjects with T1 DM in a 52-week study ADA 2009; Poster 479.
Bergeron et al. "Macromolecular Self-Assembly of Diketopiperazine Tetrapeptides." J. Am. Chem. Soc. 116, 8479-8484, 1994.
Exubera package insert, p. 1, 2008.
Fadl et al., Effects of MDI spray angle on aerosol penetration efficiency through an oral airway cast. Journal of Aerosol Science, vol. 38, No. 8, pp. 853-864 (2007).

(56) References Cited

OTHER PUBLICATIONS

Falsone et al., The Biginelli dihydropyrimidone synthesis using polyphosphate ester as a mild and efficient cyclocondensation/dehydration reagent. Institute of Chemistry, Organic and Bioorganic Chemistry, Karl-Franzens-University, pp. 122-134 (2001).
Farr, S.J. et al., Pulmonary insulin administration using the AERx® system:physiological and physiochemical factors influencing insulin effectiveness in healthy fasting subjects. Diabetes Tech. Ther. 2:185-197, 2000.
Fehmann et al. "Cell and molecular biology of the incretin hormones glucagon-like peptide-1 and glucose-dependent insulin releasing polypeptide." Endocrine Reviews 16:390, 1995.
Ferrin et al, Pulmonary retention of ultrafine and fine particles in rats. Am. J. Repir. Cell Mol. Biol., pp. 535-542 (1992).
Festa et al., "LDL particle size in relation to insulin, proinsulin, and insulin sensitivity" Diabetes Care, 22(10):1688-1693 (1999).
Forst et al., "Metabolic Effects of Mealtime Insulin Lispro in Comparison to Glibenclamide in Early Type 2 Diabetes", Exp. Clin. Endocrinol. Diabetes, 2003, 111, 97-103.
Fritsche et al. "Glimepiride Combined with Morning Insulin Glargine, Bedtime Neutral Protamine Hagedorm Insulin, or Bedtime Insulin Glargine in Patients with Type 2 Diabetes." American College of Physicians 2003.
Galinsky et al., A synthesis of diketopiperazine's using polyphosphoric acid. Journal of the American Pharmaceutical Association, vol. 46, No. 7, pp. 391-393 (1957).
Garber, "Premixed insulin analogues for the treatment of diabetes mellitus", Drugs, 66(1):31-49 (2006).
Garg et al. "Improved glycemic control without an increase in severe hypoglycemic episodes in intensively treated patients with type 1 diabetes receiving morning, evening, or split dose insulin glargine." Diabetes Research and Clinical Practice 66 (2004) 49-56.
Garg SK, Kelly W, Freson B, et al. Treat-to-target Technosphere® insulin in patients with type 1 diabetes. ADA 2011; Abstract 941-P.
Garg SK, McGill JB, Rosenstock J, et al. Technosphere® insulin vs insulin lispro in patients with type 1 diabetes using multiple daily injections. ADA, Abstract 917-P (2011).
Gates BJ "Update on advances in alternative insulin therapy." Advances in Pharmacy 1:159-168, 2003.
Glucagon for Injection (1999) glucagon for injection (rDNA origin), pp. 1-7.
Glucagon-like peptide-1; http://en.wikipedia.org/wiki/Glucagon-like peptide-1 (accessed Apr. 24, 2015).
Glucophage Product Insert. Jan. 2009.
Glucotrol Product Insert. Sep. 2006.
Gnudi L, Lorber D, Rosenstock J, et al. Basal/bolus with prandial inhaled Technosphere® insulin (TI) plus insulin glargine qd vs biaspart 70/30 insulin bid in type T2 diabetes mellitus inadequately controlled on insulin with/without oral agents. Diabetologia 2009; 52 (suppl 1).
Goke et al., Exendin-4 is a high potency agonist and truncated exendin-(9-39)-amide an antagonist at the glucagon-like peptide 1-(7-36)-amide receptor of insulin-secreting beta-cells. J. Biol. Chem. 268(26)19620-19655 (1993).
Golpon et al. "Vasorelaxant effect of glucagon-like peptide-(7-36) amide and amylin on the pulmonary circulation of the rat." Regulatory Peptides 102:81, 2001.
Gonzalez et al., Actualizacion del tratamiento farmacologico de la diabetes mellitus tipo 2. Del Sistema Nacional de Salud. Volumen 32, No. 1, pp. 3-16 (2008)—full article in Spanish with English abstract.
Gotfried M, Cassidy JP, Marino MT, et al. Lung deposition and absorption of insulin from Technosphere® insulin. Diabetologia 2009; 52 (suppl 1).
Grant et al "Both insulin sensitivity and maximal glucose elimination rate are reduced in type 2 diabetes." Presented at the American Diabetes Association 65th Scientific Sessions, Jun. 2005, abstract 2202-PO.
Grant et al. "The distribution of 14C-labeled particles following intra-tracheal liquid installation in the Sprague-Dawley rat." Presented at the American Diabetes Association 64th Scientific Sessions, Jun. 2004, abstract 461-P.
Grant M, Harris E, Leone-Bay A, Rousseau K. Technosphere®/insulin: Method of action. Diabetes Technology Meeting 2006; Poster.
Grant ML, Greene S, Stowell GW, et al. Mimicking endogenous peptide secretion by inhalation APS 2009; poster.
Greene et al. "Effects of GLP-1 Technosphere(TM) powder administered by pulmonary insufflation in male obese Zucker diabetic fat (ZDF) rats." Diabetes Technology Meeting, San Francisco, Oct. 2007.
Greene et al., Greene's protective groups in organic synthesis. 4th ed., pp. 781-783 (2007).
Gupta et al. "Contemporary Approaches in Aerosolized Drug Delivery to the Lung." J. Controlled Research, 17:129-148, 1991.
Gurrieri et al., Thermal condensation of some alpha-aminoacids with phatalic acid. Thermochimica Acta, 7 (1973) 231-239.
Gutniak et al. "Antidiabetogenic action of glucagon-like peptide-1 related to administration relative to meal intake in subjects with type 2 diabetes." J Int Med 250:81, 2001.
Gutniak et al. "Antidiabetogenic effect of glucagon-like peptide-1 (7-36)amide in normal subjects and patients with diabetes mellitus." NEJM 326:1316, 1992.
Gutniak et al. "GLP-1 tablet in type 2 diabetes in fasting and postprandial conditions." Diabetes Care 20:1874, 1997.
Gutniak et al. "Potential therapeutic levels of glucagon-like peptide I achieved in humans by a buccal tablet." Diabetes Care 19:843, 1996.
Gutniak et al. "Subcutaneious injection of the incretin hormone glucagon-like peptide 1 abolishes postprandial glycemia in NIDDM." Diabetes Care 17:1039, 1994.
Guyton et al., "Acute Control of Llocal Blood Flow", Textbook of Medical Physiology, Chapter 17, 10th Edition, W.B. Saunders Company, pp. 176-177, 2000.
Gyore et al., Thermal Analysis, vol. 2—Proceedding Fourth ICTA Budapest 1974; 387-394.
Haak "New developments in the treatment of type 1 diabetes mellitus." Exp Clin Endocrinol Diabetes 107:Suppl 3: S108, 1999.
Haffner et al., "Proinsulin and insulin concentrations I relation to carotid wall thickness", Strock 29:1498-1503 (1998).
Hagedorn et al. "Protamine Insulin", JAMA, 106:177-180 (1936).
Haino, Takeharu et al. "On-beads Screening of Solid-Attached Diketopiperzines for Calix[5]Arene-Based Receptor." Tetrahedron Letters, 40(20), 3889-3892, 2003.
Halozyme Press Release. Jun. 6, 2009.
Hanley et al., "Cross-sectional and prospective associations between proinsulin and cardovascular disease risk factors in a population experiencing rapid cultural transition" Diabetes Care 24(7): 1240-1247 (2001).
Harsch IA "Inhaled insulins. Their potential in the treatment of diabetes mellitus." Traat. Endicrinol 4:131-138, 2005.
Hassan et al. "A Randomized, Controlled Trial Comparing Twice-a-Day Insulin Glargine Mixed with Rapid-Acting Insulin Analogs Versus Standard Neutral Protamine Hagedorn (NPH) Therapy in Newly Diagnosed Type 1 Diabetes." Pediatrics, 121(3), e466-e472, 2008.
Hassan et al. "In vivo dynamic distribution of 131I-glucagon0like peptide-1 (7-36) amide in the rat studied by gamma camera." Nucl Med Biol 26:413, 1999.
Hausmann et al. "Inhaled insulin as adjunctive therapy in subjects with type 2 diabetes failing oral agents: a controlled proof of concept study." Diabetes Obesity and Metabolism 8:574, 2006.
Hayasaka et al. "Proliferation of type II pneumocytes and alteration in their apical surface membrane antigenicity in pulmonary sarcoidosis." Chest 116:477, 1999.
Li et al. "GLP-1; a novel zinc finger protein required in somatic cells of the gonad for germ cell development." Dev Biol 301:106, 2007.
Li, Jun. Chapter 15: Drug Therapy of Metabolic Diseases. Clinical Pharmacotherapy, People's Medical Publishing House, 1st Edition, pp. 333-335 (2007).

(56) References Cited

OTHER PUBLICATIONS

Lian et al. "A Self-Complimentary Self-Assembling Microsphere System: Application for Intravenous Delivery of the Antiepilpetic and Neuroprotectant Compound Felbanate." J Pharm Sci 89:867-875, 2000.

Lim, "Microencapsulation of Living Cells and Tissues", J. Pharm. Sci., 70: 351-354 (1981).

Linder et al., Increase in serum insulin levels is correlated with lung distribution after pulmonary delivery of Technosphere/Insulin. Diabetologia, No. 46, A277 (2003).

Liu et al., "Pulmonary delivery of free and liposomal insulin", Pharmaceuticals Res. 10:228-232, 1993.

Lorber D, Howard CP, Ren H, et al. Reduced incidence and frequency of hypoglycemia in an integrated analysis of pooled data from clinical trials of subjects with type 2 diabetes using prandial inhaled Technosphere® insulin. AACE 2010; Poster 270.

Luque et al. "Glucagon-like peptide-1 (GLP-1) and glucose metabolism in human myocytes." J. Endocrinol 173:465, 2002.

Luzi, L. and DeFronzo, R.A. "Effect of loss of first-phase insulin secretion on hepatic glucose production and tissue glucose disposal in humans." Am. J. Physiol. 257 (Endocrinol. Metab. 20):E241-E246, 1989.

Luzio, S.D., et al. "Intravenous insulin simulates early insulin peak and reduces post-prandial hyperglycaemia/hyperinsulinaemia in type 2 (non-insulin-dependent) diabetes mellitus." Diabetes Res. 16:63-67, 1991.

Malhotra et al., Exendin-4, a new peptide from Heloderma suspectum venom, potentiates cholecystokinin-induced amylase release from rat pancreatic acini. Regulatory Peptides, 41:149-56, 1992.

Mandal "Inhaled insulin for diabetes mellitus." Am J Health Sys Pharm 62:1359-64, 2005.

Mann "Pulmonary insulin—the future of prandial insulin therapy." Presented at the 5th Annual Meeting of the Diabetes Technology Society, Nov. 2005, abstract A94.

Mannkind Corporation "Postprandial hyperglycemia: clinical significance, pathogenesis and treatment." MannKind Corporation Monograph. 2009.

MannKind Corporation, Pulmonary Delivery: Innovative Technologies Breathing New Life into Inhalable Therapeutics, www.ondrugdelivery.com, 2006.

Burcelin et al., Long-lasting antidiabetic effect of a dipeptidyl peptidase IV-resistant analog of glucagon-like peptide-1. Metabolism, vol. 48, No. 2, pp. 252-258 (1999).

Marino MT, Cassidy JP, Smutney CC, et al. Bioequivalence and dose proportionality of Afrezza® inhalation powder administered using a Gen2 inhaler compared to the MedTone® inhaler. Diabetes Technology Meeting 2010; poster.

Marino MT, Cassidy JP, Smutney CC, et al. Improvement in bioavailability of FDKP with the NexGen2A device: Implications for delivery of pulmonary insulin. Third International Conference on Advanced Technologies and Treatments for Diabetes 2010; Poster 108.

Marino MT, Cassidy JP, Smutney CC, et al. Improvement in bioavailability of FDKP and insulin with the NGDSB device. Third International Conference on Advanced Technologies and Treatments for Diabetes 2010; Poster 107.

Marino MT. A pharmacokinetic/pharmacodynamic model of inhaled insulin with application to clinical trial simulation. ADA 2010; Abstract 2105-PO.

Marino MT. Cassidy JP, Baughman RA, et al. C-peptide correction method to determine exogenous insulin levels in pk studies using AFRESA® (Technosphere® insulin [TI]) ADA 2009; Poster 1451.

Marshall "Preventing and detecting complications of diabetes." BMJ 333:455, 2006.

Mastrandrea "A breath of life for inhaled insulin: severe subcutaneous insulin resistance as an indication." Pediatric Diabetes 2010: 11: 377-379.

Mathiowitz, Morphology of Polyanhydride Microsphere Delivery Systems, Scanning Microscopy, 4: 329-340 (1990).

Mathiowitz, Novel microcapsules for delivery systems. Reactive Polymers, 6: 275-283 (1987).

Mathiowitz, Polyanhydride microspheres as drug carriers I, hot-melt microencapsulation. J. Controlled Medicine, 5: 13-22 (1987).

Mathiowitz, Polyanhydride microspheres as drug carriers II, microencapsulation by solvent removal. J. Appl. Polymer Sci., 35: 755-774 (1988).

Mathiowitz, Polyanhydride microspheres IV, morphology and characterization systems made by spray drying. J. App. Polymer Sci., 45: 125-134 (1992).

Matsui et al. "Hyperplasia of type II pheumocytes in pulmonary lymphangioleiomyomatosis. Immunohistochemical and electron microscope study." Arch Pathol Lab Med 124:1642, 2000.

Matthews DR et al. "Homeostasis model assessment: insulin resistance and beta-cell function from fasting plasma glucose and insulin concentrations in man." Diabetologia. Jul. 1985;28(7):412-9.

McElduff A et al. "Influence of acute upper respiratory tract infection on the absorption of inhaled insulin using the AERx(R) insulin diabetes management system." Br J Clin Pharmacol 59:546, 2005.

McMahon et al., "Effects of basal insulin supplementation on disposition of mixed meal in obese patients with NIDDM", Diabetes, vol. 38, pp. 291-303 (1989).

Meier et al. "Absence of a memory effect for the insulinotropic action of glucagon-like peptide-1 (GLP-1) in healthy volunteers." Horm Metab Res 35:551, 2003.

Meier et al. "Secretion, degradation, and elimination of glucagon-like peptide-1 and gastric inhibitor polypeptide in patients with chronic renal insufficiency and healthy control subjects." Diabetes 53:654, 2004.

Meier et al. "The glucagon-like peptide-1 metabolite GLP-1-(9-36) amide reduces postprandial glycemia independently of gastric emptying and insulin secretion in humans." Am J Physiol Endocrinol Metab 290:E1118, 2006.

Mendes et al., A non-dimensional functional relationship for the fine particle fraction produced by dry powder inhalers, Aerosol Science 38, pp. 612-624 (2007).

Mentlein et al., Dipeptidyl peptidase IV hydrolyses gastric inhibitory polypeptide, glucagon-like peptide-1 (7-36) amide, peptide histidine methionine and is responsible for their degradation in human serum. Eur J Biochem., 214:829-835, 1993.

Merck Manual 17th, Japanese Edition, NIKKEI BP Corp., 1999, p. 167-179.

Mitchell et al. "Intranasal Insulin: PK Profile Designed Specifically for Prandial Treatment of Type 2 Diabetes." Drug Development Research 69(3):143-152 (2008).

Monnier et al. "Activation of oxidative stress by acute glucose fluctuations compared with sustained chronic hyperglycemia in patients with type 2 diabetes." JAMA 295:1681, 2006.

Montrose-Rafizadeh et al., Diabetes, 45(Suppl. 2):152A, 1996.

Moren, Aerosols in Medicine (2nd Ed.), Elsevier, pp. 321-350 (1993).

Mudaliar et al., Insulin Therapy in Type 2 Diabetes. Endocrinology and Metabolism Clinics, vol. 30, No. 4, pp. 1-32 (2001).

Nagai et al., "Powder Dosage Form of Insulin for Nasal Administration", J. Control Ref., 1:15-22 (1984).

Narayan et al. "Impact of recent increase in incidence on future diabetes burden." Diabetes Care 29:2114, 2006.

Naslund E et al. "GLP-1 slows solid gastric emptying and inhibits insulin, glucagon, and PYY release in humans." Am J Physiol (Regulatory Integrative Comp Physiol 46):R910, 1999.

Naslund E et al. "Prandial subcutaneous injections of glucagon-like petide-1 cause weight loss in obese human subjects." Br J Nutrition 91:439, 2004.

International Search Report dated Nov. 21, 2013 for International Application No. PCT/US2013/057397 filed on Aug. 29, 2013.

Eavarone et al., A voxel-based monte carlo model of drug release from bulk eroding nanoparticles. Journal of nanoscience and Nanotechnology, vol. 10, pp. 5903-5907 (2010).

Marino MT, Cassidy JP, Smutney CC, et al. Improvement in bioavailability of FDKP with the NexGen2A device: Implications for delivery of pulmonary insulin. Diabetes Technology Meeting 2009; poster.

(56) References Cited

OTHER PUBLICATIONS

Pfutzner et al. "Inhaled Technosphere/Insulin Shows a Low Variability in Metabolic Action in Type 2 Diabetic Patients." Diabetes 49 Supplement, May 2000, A121.
Pfuetzner A, Rave K, Heise T, et al. Inhaled Technosphere™/insulin results in low variability in metabolic action in type 2 diabetic patients. Exp Clin Endocrinol Diabetes 2000; 108:S161.
Pfuetzner A, Rave K, Heise T, et al. Low variability in metabolic action in type 2 diabetic patients with inhaled Technosphere/insulin. Diabetologia 2000; 43:Abstract 774.
Phillips M, Amin N, Boss AH, et al. Pulmonary functions (over 2 years) in diabetic subjects treated with Technosphere® insulin or usual antidiabetic treatment. Diabetologia 2009; 52 (suppl 1).
Pohl R, Muggenberg BA, Wilson BR, et al. A dog model as predictor of the temporal properties of pulmonary Technosphere/insulin in humans. Respiratory Drug Delivery 2000; VII: 463-465.
Polonsky et al. "Abnormal Patterns of Insulin Secretion in Non-insulin-Dependent Diabetes Mellitus." N Eng J Med 318:1231-39, 1988.
Potocka E, Amin N, Cassidy J, et al. Insulin pharmacokinetics following dosing with Technosphere® insulin in subjects with chronic obstructive pulmonary disease. Current Medical Research and Opinion 2010; 26:2347-2353.
Potocka E, Baughman R A, Derendorf H. Population pharmacokinetic model of human insulin following different routes of administration. Journal of Clinical Pharmacology 2011;51:1015-1024.
Potocka E, Baughman R, Derendorf H. Population Pharmacokinetic Model of Regular Human Insulin Following Different Routes of Administration. AAAP Journal. 2009; 11(S1). Available from: http://www.aapsj.org. Presented at the 2009 AAP (American Association of Pharmaceutical Scientists) National Biotechnology Conference, Jun. 21-24, Seattle, WA.
Potocka E, Baughman RA, Derendorf J. A population PK/PD model of Technosphere® insulin administered to healthy and type 2 diabetics. ADA 2010; Poster 624.
Potocka E, Baughman RA, Schwartz SL, et al. Pharmacokinetics of AFRESA® unchanged in patients with chronic obstructive pulmonary function ADA 2009; Poster 437.
Potocka E, Cassidy J P, Haworth P, et al. Pharmacokinetic characterization of the novel pulmonary delivery excipient fumaryl diketopiperazine. Journal of diabetes science and technology 2010;4:1164-1173.
Potocka E, Cassidy JP, Haworth P, et al. Pharmacokinetic characterization of fumaryl diketopiperazine. Third International Conference on Advanced Technologies and Treatments for Diabetes 2010; Poster 291.
Potocka E, Hovorka R, Baughman R, et al. Characterization of metabolism parameters following Technosphere® insulin and insulin Lispro. ADA 2010; Poster 1561.
Potocka E, Hovorka R, Baughman RA, et al. AFRESA™ supresses endogenous glucose production earlier than a rapid-acting analog (Lispro) and inhaled Exubera® ADA 2009; Oral 232.
Potocka E, Hovorka R, Baughman RA, et al. Technosphere® insulin suppresses endogenous glucose production earlier than a rapid-acting analog (lispro) and an inhaled insulin (exubera). Diabetologia 2009; 52 (suppl 1).
Prabhu et al. "A study of factors controlling dissolution kinetic of zinc complexed protein suspensions in various ionic species", Int. J. Pharm. 217(1-2):71-8 (2001).
Laube et al., The lung as an alternative route for delivery for insulin in controlling postrprandial glucose levels in patients with diabetes. Chest, Preliminary Report 114 (6) : 1734-1739 (1998).
Quattrin et al. "Efficacy and Safety of Inhaled Insulin (Exubera) Compared with Subcutaneous Insulin Therapy in Patients with Type 1 Diabetes." Diabetes Care, vol. 27, No. 11, Nov. 2004, p. 2622-2627.
Quddusi et al. "Differential effects of acute and extended infusions of glucagon-like peptide-1 on first- and second-phase insulin secretion in diabetic and nondiabetic humans." Diabetes Care 26:791, 2003.

Rachman et al. "Normalization of insulin responses to glucose by overnight infusion of glucagon-like peptide 1 (7-36) amide in patients with NIDDM." Diabetes 45:1524, 1996.
Raju et al., Naseseazines A and B: a new dimeric diketopiperazine framework from a marine-derived actinomycete, *Streptomyces* sp. Organic letters, vol. 11, No. 17, pp. 3862-3865 (2009).
Raskin et al. "Continuous subcutaneous insulin infusion and multiple daily injection therapy are equally effective in type 2 diabetes." Diabetes Care, vol. 26, No. 9, pp. 2598-2603, Sep. 2003.
Raskin P, Heller S, Honka M, et al. Pulmonary function over 2 years in diabetic patients treated with prandial inhaled Technosphere® Insulin or usual antidiabetes treatment: A randomized trial. Diabetes, Obesity and Metabolism 2012;14:163-173.
Raskin P, Phillips M, Amin N, et al. Hypoglycemia in patients with type 1 diabetes incorporating prandial inhaled Technosphere® insulin into their usual diabetes treatment regimen vs continuing their usual diabetes management. AACE 2010; Poster 283.
Raskin P, Phillips MD, Rossiter A, et al. A1C and hypoglycemia in patients with type 2 diabetes mellitus incorporating prandial inhaled Technosphere® insulin into their usual antihyperglycemic regimen vs continuing their usual antihyperglycemic regimen. ADA 2010; Abstract 359-OR.
Raufman et al., Exendin-3, a novel peptdie from Heloderma horridum venom, interacts with vasoactive intestinal peptide receptors and a newly described receptor on dispersed aciin from guinea pig pancreas. J. Biol. Chem. 266(5) : 2897-2902 (1991).
Raufman et al., Truncated glucagon-like peptide-1 interacts with exendin receptors on dispersed acini from guina pig pancreas. J. Biol. Chem. 267(30) : 21432-21437 (1992).
Raun et al. "Liraglutide, a long-acting glucagon-like peptide-1 analog, reduces body weight and food intake in obese candy-fed rats, where as a dipeptidyl peptidase-IV inhibitor, vildagliptin, does not." Diabetes 56:8, 2007.
Rave et al. "Coverage of Postprandial Blood Glucose Excursions with Inhaled Technosphere Insulin in Comparison to Subcutaneously Injected Regular Human Insulin in Subjects with Type 2 Diabetes." Diabetes Care, vol. 30, No. 9, pp. 2307-2308, Sep. 2007.
Rave et al. "Dose Response of Inhaled Dry-Powder Insulin and Dose Equivalence to Subcutaneous Insulin Lispro." Diabetes Care 28:2400-2405, 2005.
Rave et al. "Inhaled Technosphere Insulin in Comparison to Subcutaneous Regular Human Insulin: Time Action Profile and Variability in Subjects with Type 2 Diabetes." Journal of Diabetes Science and Technology, vol. 2, Issue 2, pp. 205-212, Mar. 2008.
Rave et al. "Results of a Dose-Response Study with a New Pulmonary Insulin Formulation and Inhaler." Diabetes 49, Supplement, May 2000, A75.
Rave et al. "Time-action profile of inhaled insulin in comparison with subcutaneously injected insulin lispro and regular human insulin." Diabetes Care 28:1077, 2005.
Rave K, Heise T, Pfuetzner A, et al. Assessment of dose-response characteristics for a new pulmonary insulin formulation and inhaler. Exp Clin Endocrinol Diabetes 2000; 108:S161.
Rave K, Potocka E, Boss AH, et al. Pharmacokinetics and linear exposure of AFRESA™ compared with the subcutaneous injection of regular human insulin Diabetes, Obesity and Metabolism 2009; 11:715-720.
Raz et al. "Pharmacodynamics and Pharmacokinetics of Dose Ranging Effects of Oralin versus S.C. Regular Insulin in Type 1 Diabetic Patients." Fourth Annual Diabetes Technology Meeting, Philadelphia PA, 2004.
Razavi et al. "TRPVI+ sensory neurons control beta cell stress and islet inflammation in autoimmune disease." Cell 127:1123, 2006.
Retrieved from website: http://groups.molbiosci.northwestern.edu/holmgren/Glossary/Definitions/Def-P/placebo.html, 1 page, Retrieved on Mar. 12, 2013.
Rhodes et al. "Technosphere: Microspherical Particles from Substituted Diketopiperazines for Use in Oral Drug Delivery." 208th ACS National Meeting, Aug. 1994.
Richardson et al. "Technosphere Insulin Technology." Diabetes Technology & Therapeutics, vol. 9, Supplement 1, pp. S65-S72, 2007.

(56) References Cited

OTHER PUBLICATIONS

Richardson PC, Potocka E, Baughman RA, et al. Pharmacokinetics of Technosphere® insulin unchanged in patients with chronic obstructive pulmonary disease. Diabetologia 2009; 52 (suppl 1).
Richter et al. "Characterization of glucagon-like peptide-1(7-36)amide receptors of rat membranes by covalent cross-linking." FEBS Letters 280:247, 1991.
Richter et al. "Characterization of receptors for glucagon-like peptide-1 (7-36)amide on rat lung membranes." FEBS Letters 267:78, 1990.
Riddle "Combining Sulfonylureas and Other Oral Agents." Am J Med, 2000, vol. 108(6A), pp. 15S-22S.
Riddle et al. "Emerging therapies mimicking the effects of amylin and glucagon-like peptide 1." Diabetes Care 29:435, 2006.
Ritzel et al. "Pharmacokinetic, insulinotropic, and glucagonostatic properties of GLP-1 (7-36 amide) after subcutaneous injection in healthy volunteers. Dose-response-relationships." Diabetologia 38:720, 1995.
Rosen et al., Substance P microinjected into the periaqueductal gray matter induces antinociception and is released folloing morphine administration. Brain Research, 1001: 87-94 (2004).
Rosenmund et al., Diketopiperazines from Leuchs Anhydrides. Angew Chem Intern. Edit. vol. , No. 2 (1970).
Rosenstock "Dual therapy with inhaled human insulin (Exubera(R)) as add-on to metformin (with stopping sulfonurea) is better than triple therapy with rosiglitazone add-on to combination metformin and sulfonurea in poorly controlled Type 2 diabetes." Diabetes 57:supplement 1:A557, Abstract 2018-PO, 2008.
Amorij et al., Development of stable infleunza vaccine powder formulations challenges and possibilities. Pharmaceutical Research, vol. 25, No. 6, pp. 1256-1273 (2008).
Audouy et al., Development of a dried influenza whole inactivated virus vaccine for pulmonary immunization. Vaccine, vol. 29, pp. 4345-4352 (2011).
Volund "Conversion of insulin units to SI units." American Journal of Clinical Nutrition, Nov. 1993, 58(5), pp. 714-715.
Wachters-Hagedoorn et al. "The rate of intestinal glucose absorption is correlated with plasma glucose-dependent insulinotropic polypeptide concentrations in healthy men." J Nutr 136:1511, 2006.
Wang et al., Glucagon-like peptide-1 is a physiological incretin in rat. J. Clin. Invest., 95 : 417-421 (1995).
Wang et al., Glucagon-like peptide-1 regulates proliferation and apoptosis via activation of protein kinase B in pancreatic INS-1 beta cells. Diabetologia, 47:478-487, 2004.
Wareham et al., "Fasting Proinsulin Concentrations Predict the Development of Type 2 Diabetes", Diabetes Care, 1999, 22, 262-70.
Warren et al. "Postprandial versus prandial dosing of biphasic insulin aspart in elderly type 2 diabetes patients." Diabetes Res Clin Pract 66:23-29, 2004.
Waterhouse et al., "Comparatie assessment of a new breath-actuated inhaler in patients with reversible airways obstruction", Respiration 59:155-158 (1992).
WebMD (retrieved from http://www.webmd.com/pain-management/tc/pain-management-side-effects-of-pain-medicines in 2012, 4 pages).
Wei et al. "Tissue-specific expression of the human receptor for glucagon-like peptide-1: brain and pancreatic forms have the same deduced amino acid sequence." FEBS Letters 358:219, 1995.
Weir et al. "Glucagonlike peptide 1 (7-37) actions on endocrine pancreas." Diabetes 38:338, 1989.
Weiss, SR et al. "Inhaled insulin provides improved glycemic control in patients with type 2 diabetes mellitus inadequately controlled with oral agents." Arch Intern Med 163:2277-2282, 2003.
Weissberger, "Mannkind: Overlooked Biotech with Excellent Prospects (Part V)," http://www.investorvillage.com/smbd.asp?mb=2885&mn=45817&pt=msg&mid=5021385 (posted on Jun. 19, 2008, accessed on Oct. 18, 2012).
West, Solid State Chemistry and its Applications, Chp 10, Solid Solutions. Wiley, New York, 358 (1998).
Wettergren A et al. "Truncated GLP-1 (proglucagon 78-107-Amide) inhibits gastric and pancreatic functions in man." Digestive Diseases and Sciences 38:665, 1993.
White JR et al. "Inhaled insulin: an overview." Clinical Diabetes 19:13-16, 2001.
Wigley et al., Insulin across respiratory mucosae by aerosol delivery. Diabetes 20(8): 552-556 (1971).
Willms B et al. "Gastric emptying, glucose responses, and insulin secretion after a liquid test meal: effects of exogenous glucagon-like peptide-1 (GLP-1)-(7-36) amide in type 2 (noninsulin-dependent) diabetic patients." J. Clin Endocrinol Metab 81:327, 1996.
Wilson BR et al. "Technospheres(TM) for pulmonary and nasal applications." Respiratory Drug Delivery VIII, 2002,p. 545.
Wilson et al., Spray-drying, a viable technosphere formulation process option to lyophilization, http://www.aapsj.org/abstracts/AM_2004/AAPS2004-002724.PDF, 1 page, 2004.
Witchert, Low molecular weight PLA: A suitable polymer for pulmonary administered microparticles. J. Microencapsulation, 10(2): 195-207 (1993).
Wright et al., Inhaled Insulin: Breathing new life into diabetes therapy. Nursing, vol. 37, No. 1, p. 46-48 (2007).
Wong et al. "From cradle to grave: pancreatic b-cell mass and glucagon-like peptide-1." Minerva Endocrinologica 31:107, 2006.
Wuts et al. "The Role of Protective Groups in Organic Synthesis," John Wiley, New York, 2nd Ed. 1991.
Yan et al., Analgesic action of microinjection of neurokinin A into the lateral reticular nucleus and nucleus raphe magnus in rats. Acta Physiologica Sinica, vol. 48, No. 5, pp. 493-496 (1996)—abstract.
Yang et al., Division and differentiation of natural antibody-producing cells in mouse spleen. PNAS, 104(11):4542-4546 (2007).
Yoshida et al., Absorption of insulin delivered to rabbit trachea using aerosol dosage form. J. Pharm. Sci. 68(5):670-671 (1979).
Yoshioka et al., "Serum proinsulin levels at fasting and after oral glucose load in patients with Type 2 (non-insulin dependent) diabetes mellitus", Diabetogia, 1988, 31, 355-60.
Yu W, Marino MT, Cassidy JP, et al. Insulin antibodies associated with Technosphere® insulin. ADA 2010; Abstract 216-OR.
Yusta B et al. "GLP-1 receptor activation improves b-cell function and survival following induction of endoplasmic reticulum stress." Cell Metabolism 4:391, 2006.
Zander et al., Effect of 6-week course of glucagon-like peptide 1 on glycaemic control, insulin sensitivity, and beta-cell function in type 2 diabetes: a parallel-group study. Lancet, 359:824-830, 2002.
Zethelius et al., "Proinsulin is an Independent Predictor of Coronary Heart Disease", Circulation 105:2153-2158 (2002).
Zimmerman, K., "Respiratory System: Fats, Function, and Diseases", <www.livescience.com/22616-respiratory-system.html>, copyright 2013, p. 1.
Zisser et al. "In Patients Using Technospere Insulin. Variation in PPG Stayed Within ADA-recommended Targets Despite Large Variations in Glucose Load." Mannkind Corporation (2010), ADA 2010; Poster 554.
Zisser H, Jovanovic L, Markova K, et al. Technosphere® insulin effectively controls postprandial glycemia in patients with type 2 diabetes mellitus. Diabetes Technology and Therapeutics 2012;14:997-1001.
Wasada, Glucagon-like peptide-1 (GLP-1). Nihon Rinsho, vol. 62, No. 6, pp. 1175-1180 (2004) (full Japanese article with English abstract).
Bosquillon et al., Pulmonary delivery of growth hormone using dry powders and visualization of its local fate in rates. Journal of Controlled Release 96: 233-244 (2004).
Cho et al., Targeting the glucagon receptor family for diabetes and obesity therapy. Pharmacology & Therapeutics 135: 247-278 (2012).
Definition of medicament from http://medical-dictionary.thefreedictionary.com/medicament, retrieved by the Examiner on Mar. 20, 2015 and cited in Office Action dated Mar. 26, 2015 in U.S. Appl. No. 13/492,482.
Definition of matrix from http://medical-dictionary.thefreedictionary.com/matrix, retrieved by the Examiner on Mar. 5, 2015 and cited in Office Action dated Mar. 26, 2015 in U.S. Appl. No. 12/471,260.

(56) References Cited

OTHER PUBLICATIONS

Diabetes Frontier, vol. 10, No. 5, p. 647-657 (1999) (full Japanese article with translated English portion provided in separate attachment, portion translated in English is the bottom of p. 655 and the left column of p. 656).
Ely et al., Effervescent dry powder for respiratory drug delivery. European Journal of Pharmaceutics and Biopharmaceutics 65: 346-353 (2007).
European Search report for European Application 14192154.4 dated Mar. 19, 2015.
Extended European Search report for European Application 14187552.6 dated Mar. 2, 2015.
Gillespie et al., Using carbohydrate counting in diabetes clinical practice. Journal of the American Diabetic Association, vol. 98, No. 8, p. 897-905 (1998).
Yamamoto et al., Engineering of Poly (DL-lactic-co-glycolic acid) Nano-composite particle for dry powder inhalation dosage forms of insulin with spray fludized bed granulating system. J. Soc. Powder Technol., Japan, 41: 514-521 (2004).
Heine "Unlocking the opportunity of tight glycaemic control. Promise ahead: the role of inhaled insulin in clinical practice." Diabetes, Obesity and Metabolism 7:S19, 2005.
Heinemann "Variability of Insulin Absorption and Insulin Action." Diabetes Technology & Therapeutics, vol. 4, No. 5, pp. 673-682. 2002.
Heinemann et al. "Current status of the development of inhaled insulin." Br. J. Diabetes Vasc. Dis. 4:295-301, 2004.
Heinemann L et al. "Time-action profile of inhaled insulin." Diabetic Med 14:63-72, 1997.
Heinemann, L. "Intra-individual Variability of the Metabolic Effect of Inhales Insulin Together with an Absorption Enhancer", Diabetes Care, vol. 23, No. 9, Sep. 2000, p. 1343-1347.
Heise et al. "The effect of insulin antibodies on the metabolic action of inhaled and subcutaneous insulin." Diabetes Care 28:2161, 2005.
Herbst et al., Insulin Strategies for Primary Care Providers. Clinical Diabetes, vol. 20, No. 1, pp. 11-17 (2002).
Heubner et al. "On inhalation of insulin" Klinische Wochenschrift 16:2342, 1924. (Original and English translation provided in one document).
Heyder "Particle Transport onto Human Airway Surfaces", Eur. J. Respir. Dis, Suppl. 119, 29-50 (1982).
Heyder, "Alveolar deposition of inhaled particles in humans", Am. Ind. Hyg. Assoc. J. 43(11): 864-866 (1982).
Hirsch IB "Insulin analogues." N Engl J Med 352:174-83, 2005.
Hirsch, "Type 1 Diabetes Mellitus and the Use of Flexible Insulin Regimens" American Family Phyician, Nov. 15, 1999, p. 1-16.
Hirshberg B et al. "Islet transplantation: where do we stand now?" Diabetes Metab Res Rev 19:175-8, 2003.
Hite et al. "Exhuberance over Exubera." Clin Diabetes 24(3):110-114, 2006.
Hoet et al., Review: Nanoparticles—known and unknown health risks. Journal of Nanobiotechnology, vol. 2, No. 12, (15 pages) (2004).
Hollander et al. "Efficacy and Safety of Inhaled Insulin (Exubera) Compared with Subcutaneous Insulin Therapy in Patients with Type 2 Diabetes." Diabetes Care, vol. 27, No. 10, Oct. 2004, p. 2356-2362.
Holst "Therapy of type 2 diabetes mellitus based on the actions of glucagon-like peptide-1." Diabetes Metab Res Rev 18:430, 2002.
Holst et al. "On the effects of glucagon-like peptide-1 on blood glucose regulation in normal and diabetic subjects." Ann N Y Acad Sci. Dec. 26, 1996;805:729-36.
Howard C, Ren H, Rossiter A, et al. Reduced incidence and frequency of hypoglycemia in an integrated analysis of pooled data from clinical trials of subjects with type 1 diabetes using prandial inhaled Technosphere® insulin. Diabetologia 2009; 52 (suppl 1).
Howard CP, Gnudi L, Lorber D, et al. Prandial inhaled Technosphere® insulin plus insulin glargine vs. biaspart 70/30 insulin in type 2 diabetes inadequately controlled with/without oral agents. Third International Conference on Advanced Technologies and Treatments for Diabetes. 2010; Poster 300.

Howard CP, Lorber D, Ren H, et al. Reduced incidence and frequency of hypoglycemia in pooled data from trials of type 2 diabetics using prandial inhaled Technosphere® insulin. Third International Conference on Advanced Technologies and Treatments for Diabetes 2010; Poster 304.
Howard CP, Petrucci R, Amin N, et al. Pulmonary function test remain similar in patients who received Technosphere® insulin and in patients currently receiving standard antidiabetic therapy. AACE 2010; Poster 267.
Howard CP, Ren H, Rossiter A, Boss AH. Reduced incidence and frequency of hypoglycemia in pooled data from trials of type 1 diabetics using prandial inhaled Technosphere® insulin. Third International Conference on Advanced Technologies and Treatments for Diabetes. 2010; Poster 302.
Howard CP, Ren H, Rossiter A, et al. Reduced incidence and frequency of hypoglycemia in an integrated analysis of pooled data from clinical trials of subjects with type 1 diabetes using prandial inhaled Technosphere® insulin. AACE 2010; Poster 269.
Howard CP, Rubin RR, Peyrot. M. Patient reported outcomes in adults with type 2 diabetes using mealtime AFRESA200 (inhaled Technosphere® insulin) and basal insulin versus premixed insulin ADA 2009; Poster 551.
http://www.bilcaresolutions.com/en/products/pharma-packaging-innovations-pvc-aclar-films <URL:http://web.archive.org/web/20110127102552/http://www.bilcaresolutions.com/en/products/pharma-packaging-innovations-pvc-aclar-films> published Jan. 27, 2011 as per "Wayback Engine".
http://www.pmpnews.com/article/blister-packaging-materials (May 26, 2009).
Huda et al. "Gut peptides and the regulation of appetite." Obesity Reviews 7:163, 2006.
Hui et al., The short half-life of glucagon-like peptide-1 in plasma does not reflect its long-lasting beneficial effects. European Journal of Endocrinology, 146: 863-869 (2002).
Hussain et al. "State of insulin self-association does not affects its absorption from the pulmonary route." Eur. J. Pharm. Sciences 25:289-298, 2005.
Ikeda, Kuniki et al. "Peptide Antibiotics. XXVI. Syntheses of Cyclodipeptides Containing N. delta.-p-aminobenzenesulfonyl Ornithine Residue." Chemical & Pharmaceutical Bulletin, 20(9), 1849-55, 1972.
Imeryuz et al. "Glucagon-like peptide-1 inhibits gastric emptying via vagal afferent-mediated central mechanisms." Am J Physiol 273 (Gastrointest Liver Physiol 36):G920, 1997.
Insulin inhalation NN 1998, Drugs R & D, 2004, pp. 46-49, Adis Data Information BV.
Insulin is a natural product from http://www.levemir.comistartingoninsulin/whatisinulin.aspx, pp. 1-3. Accessed by Examiner on Apr. 30, 2014 and in Non-Final Office Action dated May 22, 2014 for U.S. Appl. No. 13/797,657 and in Non-Final Office Action dated May 22, 2014 for U.S. Appl. No. 12/883,369.
International Search Report for PCT International Application No. PCT/US2010/055323 filed on Nov. 3, 2010.
Written Opinion dated Jul. 1, 2013 for International Application No. PCT/US2013/032162 filed on Mar. 15, 2013.
International Search Report dated Jun. 21, 2010 for International Application No. PCT/US2010/027038 filed on Mar. 11, 2010.
Written Opinion for International Application No. PCT/US2011/060057 filed on Nov. 9, 2011.
International Search Report dated Mar. 18, 2013 for International Application No. PCT/US2012/061749 filed on Oct. 24, 2012.
International Search Report dated Jun. 20, 2012 for International Applicaion No. PCT/US2012/031695 filed on Mar. 30, 2012.
International Search Report dated Nov. 19, 2014 for International Application No. PCT/US2014/049817 filed on Aug. 5, 2014.
International Search Report for International Application No. PCT/US2010/020448 filed on Jan. 8, 2010.
International Search Report dated Mar. 11, 2010 for International Application No. PCT/US2009/069745 filed on Dec. 29, 2009.
International Search Report dated Oct. 17, 2011 for International Application No. PCT/US2010/026271 filed on Mar. 4, 2010.
International Search Report for International Application No. PCT/US2010/038287 filed on Jun. 11, 2010.

(56) References Cited

OTHER PUBLICATIONS

Ishibashi, Norio et al. "Studies on Flavored Peptides. Part V. A Mechanism for Bitter Taste Sensibility in Peptides." Agricultural and Biological Chemistry, 52(3), 819-27, 1988.
Iwanij et al., Characterization of the Glucagon Receptor and its Functional Domains Using Monoclonal Antibodies. The Journal of Biological Chemistry, vol. 265, No. 34, pp. 21302-21308, 1990.
Jain et al. "Insulin Therapy in Type 2 Diabetic Subjects Suppresses Plasminogen Activator Inhibitor (PAI-1) Activity and Proinsulin-like Molecules Independently of Glycaemic Control." Diabetic Medicine, vol. 10, No. 1, p. 27-32, 1993.
Johnson et al., Peptide turn mimetics. Biotechnology and Pharmacy, p. 366-378 (1993).
International Search Report for International Application No. PCT/US2013/050392 filed on Jul. 12, 2013.
Nathan DM et al. "Management of hyperglycemia in Type 2 diabetes: a consensus algorithm for the initiation and adjustment of therapy." Diabetes Care 29:1963-1972, 2006.
Nathan DM et al. "Management of hyperglycemia in Type 2 diabetes: a consensus algorithm for the initiation and adjustment of therapy." Diabetes Care 31:173-175, 2008.
Nathan DM et al. "Management of hyperglycemia in Type 2 diabetes: a consensus algorithm for the initiation and adjustment of therapy." Diabetes Care 32:193-203, 2009.
Nathan et al. "Intensive diabetes treatment and cardiovascular disease in patients with Type 1 diabetes." New Eng. J. Med. 353:2643-2653, 2005.
Nathan, "Initial Management of Glycemia in Type 2 Diabetes Melllitus" N. Eng. J. Med., 2002, 347, 1342-9.
Nauck "Is glucagon-like peptide 1 an incretin hormone?" Diabetologia 42:373-379, 1999.
Nauck et al. "Glucagon-like peptide 1 inhibition of gastric emptying outweighs its insulinotropic effects in healthy humans." Am J Physiol 273 (Endocrinol Metabl 36):E981, 1997.
Nauck et al. "Reduced incretin effect in type 2 (non-insulin-dependent) diabetes." Diabetologia 29:46-52, 1986.
Nauck et al., Effects of glucagon-like peptide 1 on counterregulatory hormone responses, cognitive functions, and insulin secretion during hyperinsulinemic, stepped hypoglycemic clamp experiments in healthy volunteers. J Clin Endocrinol Metab., 87:1239-1246, 2002.
Nauck et al., Effects of subcutaneous glucagon-like peptide 1 (GLP-1 [7-36 amide]) in patients with NIDDM. Diabetologia, 39:1546-1553, 1996.
Nauck et al., Normalization of fasting hyperglycemia by exogenous GLP-1 (7-36 amide) in type 2 diabetic patients. Diabetologia, 36:741-744, 1993.
Nemmar et al., Passage of inhaled particles into the blood circulation in humans. Circulation pp. 411-414 (2002).
Newman, Principles of metered-dose inhaler design. Respiratory Care, vol. 50, No. 9, pp. 1177-1190 (2005).
Next Generation Inhaler Nears Market, Manufacturing Chemist, Cambridge Consultants, Polygon Media Ltd. (2006).
NHS Clinical Guidelines, "Type 1 diabetes diagnosis and mangement of type 1 diabetes in children and young people", National Collaborating Centre for Women's and Children's Health Commissioned by the National Institute for Clinical Excellence, Sep. 2004, p. 1-217.
Non-covalent interactions from UC Davis ChemWiki, pp. 1-5. Accessed by Examiner on Jul. 23, 2013 and related case U.S. Appl. No. 12/830,557.
Nystrom et al. "Effects of glucagon-like peptide-1 on endothelial function in type 2 diabetic patients with stable coronary artery disease." Am J Physiol Endocrinol Metabl 287:E1209, 2004.
Oberdorster et al., Correlation between particle size, in vivo particle persistence, and lung injury. Environ Health Perspect 102 Suppl 5, pp. 173-179 (1994).
Oberdorster et al.,Pulmonary effects of inhaled ultrafine particles. International Archives of Occupational and Environmental Health, vol. 74, pp. 1-8 (2001).
Okumura et al., Intratracheal delivery of insulin: absorption from solution and aerosol by rat lung. Int. J. Pharmaceuticals 88: 63-73 (1992).
O'Neill, Air pollution and inflammation in type 2 diabetes: a mechanism for susceptibility. Occup Environ Med. vol. 64, pp. 373-379 (2007).
Orgsoltab et al., Division of Organic Chemistry. Ohio Northern University. Nov. 24, 2009. Available from: <http://www.2.onu.edu/~b-meyers/organic_solvents.html>.
Oshima et al. "Comparison of half-disappearance times, distribution volumes and metabolic clearance rates of exogenous glucagon-like peptide 1 and glucagon in rats." Regulatory Peptides 21:85, 1988.
Ostrovsky, Gene. Mannkind Inhalation Insulin Going to FDA to Seek Approval [on-line]. MedGadget.com, posted on Mar. 17, 2009, Retrieved from the Internet: <URL:http://medgadget.com/2009/03mannkind_inhalation_insulin_going_to_fda_to_seek_approval.html>.
Owens et al. "Inhaled human insulin." Nature Reviews, Drug Discovery, vol. 5, No. 5, pp. 371-372, May 2006.
Owens et al. "Alternative routes of insulin delivery." Diabetic Medicine 20:886-898, 2003.
Ozyazgan et al. "Effect of glucagon-like peptide-1)7-36) and exendin-4 on the vascular reactivity in streptozotocin/nicotinamide-induced diabetic rats." Pharmacology 74:119, 2005.
Pacini P, Marino MT. Evaluation of endogenous and exogenous components to peripheral insulin concentration during administration of inhaled insulin. ADA 2010; Abstract 2094-PO.
Patton "Mechanisms of macromolecule absorption by the lungs." Advanced Drug Delivery Reviews 19:3, 1996.
Patton "Unlocking the opportunity of tight glycaemic control. Innovative delivery of insulin via the lung." Diabetes Obesity and Metabolism 7:S5, 2005.
Patton & Platz, Routes of Delivery: Case studies: pulmonary delivery of peptides and proteins for systemic action. Adv. Drug. Del. Rev. 8: 179-196 (1992).
Patton et al. "The lungs as a portal of entry for systemic drug delivery." Proc Am Thorac Soc 1:338, 2004.
Patton et al. "Clinical pharmacokinetics and pharmacodynamics of inhaled insulin." Clin Pharmacokinet 43:781-801, 2004.
Patton et al., "Inhaled Insulin", Advanced Drug Delivery Reviews, 35, Feb. 1999, p. 235-247.
Onoue et al., Dry powder inhalation systems for pulmonary delivery of therapeutic peptides and proteins. Expert Opin. Ther. Patents 18(4):429-442 (2008).
Pearson et al., Systematically Initiating Insulin, supplemental to vol. 32, No. 1, 19S-28S, 2006.
Perera et al. "Absorption and Metabolic Effect of Inhaled Insulin." Diabetes Care, vol. 25, No. 12, Dec. 2002, p. 2276-2281.
Pesic, Inhaler delivers more drug to the deep lung, says Cambridge Consultants. in-Pharma Technologist.com, http://www/in-pharmatechnologist.com/content/view/print/344335, Dec. 1, 2010.
Petkowicz et al., "Hypoglycemic effect of liposome-entrapped insulin adminstered by various routes into normal rats", Pol. J. Pharmacol. Pharm. 41:299-304 (1989).
Petrucci R, Amin N, Lovertin P. et al. Pulmonary function tests remain similar in patients who received Technosphere® insulin and in patients currently receiving standard antidiabetic therapy. Diabetologia 2009; 52 (suppl 1).
Peyrot et al. "Resistance to insulin therapy among patients and providers." Diabetes Care 28:2673-2679, 2005.
Peyrot M, Rubin RR, Otterbach K. Effect of Technosphere® inhaled insulin on treatment satisfaction, glycemic control and quality of life. Diabetes 2006; 55:Abstract 423-P.
Pezron et al., Insulin aggregation and asymmetric transport across human bronchial epithelial cell monolayers (Calu-3). J. Pharmaceutical Sci. 91: 1135-1146 (2002).
Pfeiffer MA et al. Insulin secretion in diabetes mellitus. Am J Med 70:579-88, 1981.
Pfutzner et al., Abstract 812: Influence of small dose i.v.s.c. and pulmonary insulin treatment on grandial glucose control in patients with type 2 diabetes. Internet Article [Online] 2001, 37th Annual Meeting of the EASD, Glasgow, Sep. 9-13, 2001.

(56) References Cited

OTHER PUBLICATIONS

Pfützner A et al. "Pulmonary insulin delivery by means of the Technosphere(TM) drug carrier mechanism." Expert Opin Drug Deliv 2:1097-1106, 2005.
Pfützner A et al. "Technosphere®/Insulin—a new approach for effective delivery of human insulin via the pulmonary route." Diab Tech Ther 4:589-594, 2002.
Pfützner A et al. "Lung distribution of radiolabeled Technosphere™/ Insulin." Diabetes 52 Supplement, Jun. 2003, A107.
Pfützner A et al. Pilot study with Technosphere/PTH(1-34)—a new approach for effective pulmonary delivery of parathyroid hormone (1-34). Horm Metab Res 35:319-323, 2003.
Pfützner A et al. "Variability of insulin absorption after subcutaneous and pulmonary application in patients with type 2 diabetes." Diabetes 51 Supplement, Jun. 2002, A47-48.
Shields, Irritable bowel syndrome, archived Jun. 21, 2009, available at: https://web.archive.org/web/200906211 00502/http://www.gastroenterologistpaloalto.com/conditions-disease-irritable-bowelsyndrome-palo-alto-ca. html; Aug. 26, 2015 in U.S. Appl. No. 14/139,714.
Smith et al., Evaluation of novel aerosol formulations designed for mucosal vaccination against infleunza virus. Vacine, vol. 21, pp. 2805-2812 (2003).
Uwaifo et al., Novel pharmacologic agents for type 2 diabetes. Endocrinology and Metabolism Clinics of North America, vol. 34, No. 1, pp. 155-197 (2005).
Xi-de Tu, et al. Pharmaceutics. Oct. 2002, 3rd edition, second printing, p. 905.
Chan et al., Physical stability of salmon calcitonin spray-dried powders for inhalation. Journal of Pharmaceutical Sciences, vol. 93, No. 3, pp. 792-804 (2004).
Young et al., Encapsulation of lysozyme in a biodegradable polymer by preparation with a vapor-over-liquid antisolvent. Journal of Pharmaceutical Sciences, 88:640-650 (1999).
Hazard Prevention and Control in the Work Environment: Airborne Dust WHO/SDE/OEH/99. 14 Chapter 1—Dust: Definitions and Concepts [retrieved from internet by Examiner in European case on Sep. 22, 2015]. <URL: http://www.who.int/occupational_health/publications/airdust/en/> published on Oct. 29, 2004 as per Wayback Machine.
Owens et al., Blood glucose self-monitoring in type 1 and type 2 diabetes: reaching a multidisciplinary consensus. Diabetes and Primary Care, vol. 6, No. 1, pp. 8-16 (2004).
Sarala et al., Technosphere: New drug delivery system for inhaled insulin. Future Prescriber, vol. 13, No. 1, pp. 14-16 (2012).
Bilheimer DW, Ren H, Boss AH. Analysis of cardiovascular adverse events in patients with type 1 or type 2 diabetes enrolled in selected therapeutic trials in the phase 2/3 Technosphere® insulin development program. ADA 2011. Poster 922-P.
Billings CC, Smutney CC, Howard CP, et al. Handleability and characterization of inhalation profiles using the Gen2 delivery system in a pediatric population. Diabetes Technology Meeting 2010; poster.
Biodel's Intellecutal Property position strengthened for ultra-rapid-acting insulin programs by notice of intent to grant from European Patent Office. Newswire Feed, published May 2, 2012.
Blazquez E et al. "Glucagon-like peptide-1 (7-36) amide as a novel neuropeptide." Mol Neurobio 18:157, 1998.
Bloomgarden "Gut-derived incretin hormones and new therapeutic approaches." Diabetes Care 27:2554, 2004.
Boer et al., Design and application of a new modular adapter for laser diffraction characterization of inhalation aerosols. International Jornal of Pharmaceutics 249, pp. 233-245 (2002).
Boer et al., Inhalation characteristics and their effects on in vitro drug delivery from dry powder inhalers. Part 1. Inhalation characteristics, work of breathing and volunteers' preference in dependence of the inhaler resistance. Int. J. Pharm. 130 (1996) 231-244.

Bojanowska "Physiology and pathophysiology of glucagon-like peptide-1 (GLP-1): the role of GLP-1 in the pathogenesis of diabetes mellitus, obesity and stress." Med Sci Monit 11:RA271, 2005.
Bonner-Weir S et al. "New sources of pancreatic beta-cells." Nat Biotechnol 23:857-61, 2005.
Boss AH et al. "Inhaled Technosphere®/Insulin: Glucose elimination at the right time?" Poster presented at the American Diabetes Association 65th Scientific Sessions, Jun. 2005, abstract 443-P.
Boss AH et al. "Insulin bio-effect is limited by speed of absorption and elimination: similarities between an inhaled insulin formulation that mimics first-phase kinetics and i.v. insulin." Diabetologia 47:A314, 2004.
Boss AH et al. "Mimicry of the early phase insulin response in humans with rapidly available inhaled insulin accelerates post prandial glucose disposal compared to slower bioavailable insulin." Presented at the American Diabetes Association 65th Scientific Sessions, Jun. 2005, abstract 1373-P.
Boss AH et al. "Does kinetics matter? Physiological consequences of the ability of Technosphere®/Insulin inhalation to mimic first phase insulin release." Presented at the 5th Annual Meeting of the Diabetes Technology Society, Nov. 2005, abstract A14.
Boss AH et al. "Markedly reduced post prandial glucose excursions through inhaled Technosphere®/Insulin in comparison to SC injected regular insulin in subjects with type 2 diabetes." 1st Annual Meeting of the European Association for the Study of Diabetes, Sep. 2005, abstract 816.
Boss AH et al. "The variability and time-action profile of inhaled Technosphere®/Insulin compares favorably to that of subcutaneous human regular insulin." Presented at the American Diabetes Association 65th Scientific Sessions, Jun. 2005, abstract 358-OR.
Boss et al. "Prandial Insulin: Is Inhaled Enough?" Drug Development Research 69(3):138-142 (2008).
Boss A H, Petrucci R, Lorber D. Coverage of prandial insulin requirements by means of an ultra-rapid-acting inhaled insulin. Journal of diabetes science and technology 2012;6:773-779.
Boss AH, Baughman RA, Evans SH, et al. A 3 month comparison in type 1 diabetes of inhaled Technosphere®/Insulin (TI) to Sc administered rapid-acting insulin analogue (RAA) as prandial insulin in a basal/prandial regimen. Diabetes 2006; 55:A97.
Boss AH, Evans SH, Firsov I, et al. Technosphere® insulin as effective as sc rapid acting insulin analogue in providing glycemic control in a 6-month study of patients with type 2 diabetes. Diabetes Technology Meeting 2006; poster.
Boss AH, Evans, SH, Ren, H, et al. Superior post prandial glucose control in patients with type 1 diabetes when using prandial technosphere insulin compared to NovoLog. Diabetologia 2006; Abstract 181.
Boss AH, Marino MT, Cassidy JP, et al. C-peptide correction method to determine exogenous insulin levels in pharmacokinetic studies using Technosphere® insulin. Diabetologia 2009; 52 (suppl 1).
Boss AH, Raskin P, Philips M, et al. Glycosylated hemoglobin and hypoglycaemia in patients with Type 2 diabetes mellitus: Technosphere® insulin and usual antihyperglycaemic regimen vs usual antihyperglycaemic regimen. Diabetologia 2010;53(suppl 1).
Brandt D, Boss AH. The next generation insulin therapy. OndrugDelivery 2006 (published online).
Brange et al., "Insulin Structure and Stability", Pharm Biotechnol, 5:315-50 (1993).
Bray "Exanatide" Am J Health-Sys Pharm 63:411, 2006.
Brownlee et al. "Glycemic variability: a hemoglobin A1c-independent risk factor for diabetic complications." JAMA 295:1707, 2006.
Bruce, D.G., et al. "Physiological importance of deficiency of early prandial insulin secretion in non-insulin-dependent diabetes." Diabetes 37:736-44, 1988.
Bullock BP et al. "Tissue distribution of messenger ribonucleic acid encoding the rat glucagon-like peptide-1 receptor." Endocrinology 137:2968, 1996.
Burcelin et al. "Encapsulated, genetically engineered cells, secreting glucagon-like peptide-1 for the treatment of non-insulin-dependent diabetes mellitus." Ann N Y Acad Sci. Jun. 18, 1999;875:277-85.

(56) References Cited

OTHER PUBLICATIONS

Calles-Escandon, J. And Robbins, D.C. "Loss of early phase insulin release in humans impairs glucose tolerance and blunts thermic effect of glucose." Diabetes 36:1167-72, 1987.
Camilleri, Clinical Practice: Diabetic Gastroparesis. The New England Journal of Medicine, 356: 820-829 (2007).
Campos et al. "Divergent tissue-specific and developmental expression of receptors for glucagon and glucagon0like peptide-1 in the mouse." Endocrinology 134:2156, 1994.
Cassidy J P, Amin N, Marino M, et al. Insulin lung deposition and clearance following Technosphere® insulin inhalation powder administration. Pharmaceutical Research 2011; 28:2157-2164.
Cassidy J, Amin N, Baughman R, et al. Insulin kinetics following Technosphere® insulin inhalation powder administration unchanged in albuterol-treated asthmatics. ADA 2010; Poster 522.
Cassidy J, Baughman RA, Tonelli G, et al. Use of rapid acting insulin analog as the baseline infusion during glucose clamping improves pharmacokinetic evaluation. ADA 2007; 56: Abstract 602-P.
Cassidy JP, Baughman RA, Schwartz SL, et al. AFRESA® (Technosphere® insulin) dosage strengths are interchangeable ADA 2009; Poster 433.
Cassidy JP, Marino MT, Amin N, et al. Lung deposition and absorption of insulin from AFRESA® (Technosphere® insulin) ADA 2009; Poster 425.
Cassidy JP, Potocka E, Baughman RA, et al. Pharmacokinetic characterization of the Technosphere® inhalation platform Diabetes Technology Meeting 2009. poster.
Caumo et al. "First-phase insulin secretion: does it exist in real life" Considerations on shape and function. Am J Physiol Endocrinol Metab 287:E371-E385, 2004.
Cefalu "Concept, Strategies and Feasibility of Noninvasive Insulin Delivery." Diabetes Care 27:239-246, 2004.
Cefalu "Novel routes of insulin delivery for patients with type 1 or type 2 diabetes." Ann Med 33:579-586, 2001.
Cefalu et al., Inhaled human insulin treatment in patients with type 2 diabetes mellitus. Ann. Int. Med., 2001, 134(3):203-207.
Ceglia et al. "Meta-analysis: efficacy and safety of inhaled insulin therapy in adults with diabetes mellitus." Ann Intern Med 145:665, 2006.
Cerasi, et al. Decreased sensitivity of the pancreatic beta cells to glucose in prediabetic and diabetic subjects. A glucose dose-response study. Diabetes 21(4):224-34, 1972.
Cernea et al. "Dose-response relationship of oral insulin spray in healthy subjects." Diabetes Care 28:1353-1357, 2005.
Cernea et al. "Noninjectable Methods of Insulin Administration." Drugs of Today 2006, 42 (6): 405-424.
Chan et al., "Pharmacological Management of Type 2 Diabetes Mellitus: Rationale for Rational Use of Insulin", Mayo Clin Proc, 2003, 78, 459-467.
Chase et al., "Redefining the clinical remission period in children with type 1 diabetes", Pediatric Diabetes, 2004, 5, 16-19.
Cheatham et al. "Desirable Dynamics & Performance of Inhaled Insulin Compared to Subcutaneous Insulin Given at Mealtime in Type 2 Diabetes: A Report from the Technosphere/Insulin Study Group." Diabetes Technology and Therapeutics, vol. 6, p. 234 (2004).
Cheatham et al. "A novel pulmonary insulin formulation replicates first phase insulin release and reduces s-proinsulin levels." Presented at the American Diabetes Association 64th Scientific Sessions, Jun. 2004, abstract 457-P.
Rosenstock et al. "Efficacy and Safety of Technosphere Inhaled Insulin Compared With Technosphere Powder Placebo in Insulin-Naive Type 2 Diabetes Suboptimally Controlled with Oral Agents." Diabetes Care, vol. 31, No. 11, pp. 2177-2182, 2008.
Rosenstock et al. "Inhaled Insulin Improves Glycemic Control when Substituted for or Added to Oral Combination Therapy in Type 2 Diabetes." Ann Intern Med 143:549-558, 2005.
Rosenstock et al., "Reduced hypoglycemia risk with insulin glargine: a meta-analysis comparing insulin glargine with human NPH insulin in type 2 diabetes", Diabetes Care, 28(4):950-5 (2005).
Rosenstock J, Baughman RA, Ribera-Schaub T, et Al. A randomized, double-blind, placebo controlled study of the efficacy and safety of inhaled Technosphere® insulin in patients with type 2 diabetes (T2DM). Diabetes 2005;54: Abstract 357-OR.
Rosenstock J, Lorber D, Petrucci R, et al. Basal/bolus with prandial inhaled Technosphere® insulin (TI) plus insulin glargine qd vs biaspart 70/30 insulin bid in T2 DM inadequately controlled on insulin with/without oral agents ADA 2009; Poster 466.
Rosenstock J, Lorger DL. Gnudi L, et al.Prandial inhaled insulin plus basal insulin glargine versus twice daily biaspart insulin for type 2 diabetes: a multicentre randomised trial. Lancet 2010;375:2244-2253.
Rossiter A, Amin N, Harris R, et al. Pulmonary safety of inhaled Technosphere® insulin therapy in adults with diabetes using high-resolution computerized tomography of the chest. Diabetologia 2009; 52 (suppl 1).
Rossiter A, Howard C, Amin N, et al. Technosphere® insulin: Safety in type 2 diabetes mellitus. ADA 2010; Poster 523.
Roumeliotis, New inhaler launched with a bag, in-Pharma Technologist.com, Decision News Media SAS (2006).
Rousseau et al. "Drug delivery by fumaryl diketopiperazine particles: evidence for passive transport." Presented at the American Diabetes Association 64th Scientific Sessions, Jun. 2004, abstract 484-P.
Rubin RR, Peyrot M. Psychometric properties of an instrument for assessing the experience of patients treated with inhaled insulin: The inhaled insulin treatment questionnaire (INTQ) Health & Quality of Life Outcomes 2010.8:32.
Rubin RR, Peyrot M; Patient reported outcomes in adults with type 1 diabetes using mealtime AFRESA® (inhaled Technosphere® insulin) or rapid acting insulin with basal insulin ADA 2009; Poster 1881.
Ryan EA et al. "Successful islet transplantation. Continued insulin reserve provides long-term glycemic control." Diabetes 51:2148-2157, 2002.
Sajeesh et al., Cyclodextrin-insulin complex encapsulated polymethacrylic acid based nanoparticles for oral insulin delivery. International Journal of Pharmaceuticals, 2006, 325, pp. 147-154.
Sakagami M et al. "Respirable microspheres for inhalation: the potential of manipulating pulmonary disposition for improved therapeutic efficacy." Clin Pharmacokinet 44(3):263-277, 2005.
Sakr, A new approach for insulin delivery via the pulmonary route: design and pharmacokinetics in non-diabetic rabbits. International Journal of Pharmaceutics, 86: 1-7 (1992).
Salib, Utilization of sodium alginate in drug microencapsulation. Pharazeutische Industrie, 40(11a): 1230-1234 (1978).
Saraceni C et al. "Effects of glucagon-like peptide-1 and long-acting analogues on cardiovascular and metabolic function." Drugs R D 8:145, 2007.
Sarrach et al., "Binding and entrapment of insulin by liposomes made of lecithin-phosphotidix acid in acid solution" Pharmazie 40:642-645, 1985 (German and English Abstract).
Savage et al., "Effects of peptide YY (PYY) on mouth to caecum intestinal transit time and on the rate of gastric emptying healthy volunteers", Gut, vol. 28, pp. 166-170, 1987.
Sawhney et al., Bioerodible hydrogels based on photopolymerized poly(ethylene glycol)-co-poly(a-hydroxy acid) diacrylate macromers. Macromolecules, 26: 581-587 (1993).
Schaffer et al. "Assembly of high-affinity insulin receptor agonists and antagonists from peptide building blocks." PNAS 100:4435-4439, 2003.
Schepp et al., Eur. J. Pharmacol., 269:183-91, 1994.
Scherbaum "Unlocking the opportunity of tight glycaemic control. Inhaled insulin: clinical efficacy." Diabetes Obesity and Metabolism 7:S9-S13, 2005.
Schirra et al. "Gastric emptying and release of incretin hormones after glucose ingestion in humans." J Clin Invest 97:92-103, 1996.
Schluter et al., "Pulmonary Administration of Human Insulin in volunteers and Type I Diabetics", Diabetes, 33, (Suppl) 298 (1984).

(56) References Cited

OTHER PUBLICATIONS

Schneider et al., "Stimulation by proinsulin of expression of plasminogen activator inhibitor type 1 in endothelial cells", Diabetes 41(7):890-895 (1992).
Schon, Istvan et al. "Formation of Aminosuccinyl Peptides During Acidolytic Deprotection Followed by their Tranformation to Piperazine-2, 5-dione Derivatives in Neutral Media." International Journal of Peptide & Protein Research, 14(5), 485-494, 1979.
Schroder, "Crystallized carbohydrate spheres as a slow release matrix for biologically active substances", Biomaterials 5:100-104, 1984.
Scrocchi et al. "Glucose intolerance but normal satiety in mice with a null mutation in the glucagon-like peptide 1 receptor gene." Nature Medicine 2:1254-1258, 1996.
Seshiah & Balaji, "Early Insulin Therapy in Type 2 Diabetics", Int. J. Diabetes in Developing Countries, 2003, 23, 90-93.
Seville, P.C. et al., Preparation of dry powder dispersions for non-viral gene delivery by freeze-drying and spray drying. J. Gene Medicine 2002; 4:428-437.
Shah et al. "Lack of suprression of glucagon contributes to postprandial hyperglycemia in subjects with type 2 diabetes mellitus." J Clin Indocrinol Metab 85:4053, 2000.
Shelly et al. "Polysorbate 80 hypersensitivity." The Lancet 345:1312, 1995.
Shimada et al. Translocation pathway of the intertracheally instilled ultrafine particles from the lung into the blood circulationin the mouse. Toxicologic Pathology pp. 949-957 (2006).
Shojania et al. "Effect of quality improvement strategies for type 2 diabetes on glycemic control." JAMA 296:427, 2006.
Silverstein et al., "Care of Children and Adolescens with Type 1 Diabetes, A Statement of the American Diabetes Association", Diabetes Care, Jan. 2005, vol. 28, p. 186-212.
Singh et al., Use of 125I-[Y39]exendin-4 to characterize exendin receptors on dispersed pancreatic acini and gastric chief cells from guinea pig. Regul. Pept. 53 : 47-59 (1994).
Simms JR, Carballo I, Auge CR, et al. Assessment of immunotoxic effects on humoral and cellular immune parameters following repeated inhalation of Technosphere insulin in the rat. Diabetes 2005;54:Abstract 2078-PO.
Skyler, Pulmonary insulin: current status. Diabetes Voice, vol. 51, Issue I, p. 23-25, 2006.
Skyler "Pulmonary Insulin Delivery—State of the Art 2007." Diabetes Tecnology & Therapeutics, vol. 9, Supplement 1, pp. S1-S3. 2007.
Skyler JS et al. "Use of inhaled insulin in a basal/bolus insulin regimen in Type 1 diabetic subjects." Diabetes Care 28:1630-1635, 2005.
Smith et al. "New-onset diabetes and risk of all-cause and cardiovascular mortality." Diabetes Care 29:2012, 2006.
Smutney CC, Friedman EM, Amin N. Inspiratory efforts achieved in use of the Technosphere® insulin inhalation system. Diabetes Technology Meeting 2008; Poster SMUT8052.
Smutney CC, Friedman EM, Amin N. Inspiratory efforts achieved in use of the Technosphere® insulin inhalation system. Journal of Diabetes Science and Technology 2009 3(5):1175-1189.
Smutney CC, Polidoro JM, Adamo B, et al. In-vitro performance improvement realized in a next generation dry powder delivery system. Diabetes Technology Meeting 2009; Poster.
Smutney CC, Polidoro JM, Adamo B, Shah S. In vitro performance improvement realized in a next generation dry powder delivery system. Third International Conference on Advanced Technologies and Treatments for Diabetes 2010; Poster 122.
Smutney CC, Polidoro JM. Easy-to-use next-generation pulmonary insulin delivery system. ADA 2010; Abstract 2093.
Smutney CC, Polidoro JM. Improvements realized in a next-generation pulmonary insulin delivery system. ADA 2010; Abstract 2097.
Sodium chloride is a natural product from http://www.wqpmag.com/potassium-chloride-vs-sodium-chloride, pp. 1-3 . Accessed by Examiner on May 16, 2014 and in Non-Final Office Action dated May 22, 2014 for U.S. Appl. No. 13/797,657 and in Non-Final Office Action dated May 22, 2014 for U.S. Appl. No. 12/883,369.

Johnson et al., "Turbuhaler a new device for dry powder terbutaline inhalation", Allergy 43(5):392-395 (1988).
Johnson et al: RyR2 and calpain-10 delineate a novel apoptosis pathway in pancreatic islets. J Biol Chem., 279(23):24794-802, 2004.
Johnson, Keith A., Preparation of peptide and protein powders for inhalation. Advanced Drug Delivery Reviews 1997; 26:3-15.
Jones et al., An investigation of the pulmonary absorption of insulin in the rat. Third European Congress of Biopharmaceutics and Pharmacokinetics, (1987).
Joseph et al. "Oral delivery of glucagon-like peptide-1 in a modified polymer preparation normalizes basal glycaemia in diabetic db/db mice." Diabetologia 43:1319-1328, 2000.
Joy et al. "Incretin mimetics as emerging treatments for type 2 diabetes." Annal Pharmacother 39:110, 2005.
Juntti-Berggren et al. "The antidiabetogenic effect of GLP-1 is maintained during a 7-day treatment period and improves diabetic dyslipoproteinemia in NIDDM patients." Diabetes Care 19:1200-1206, 1996.
Kanse et al. "Identification and characterization of glucagon-like peptide-1 7-36 amide-binding sites in the rat brain and lung." FEBS Letters 241:209, 1988.
Kapitza C et al. "Impact of particle size and aerosolization time on the metabolic effect of an inhaled insulin aerosol." Diabetes Tech Ther 6:119, 2004.
Kapitza et al. "Dose-response characteristics for a new pulmonary insulin formulation and inhaler." Presented at the 35th Annual Meeting of the EASD, Sep. 2000, abstract OP29 184.
Kapsner P, Bergenstal RM, Rendell M, et al. Comparative efficacy and safety of Technosphere® insulin and a rapid-acting analog both given with glargine in subjects with type 1 diabetes in a 52-week study. Diabetologia 2009; 52(suppl 1).
Katchalski E et al. "Synthesis of lysine anhydride", J. Amer Chem Soc 68:879-880, 1946.
Katz et al. "Quantitative insulin sensitivity check index: a simple, accurate method for assessing insulin sensitivity in humans." J. Clin. Endocrinol. Metab. 85:5402-2410, 2000.
Kaur et al. "A Delineation of Diketopiperazine Self-Assembly Processes: Understanding the Molecular Events Involved in Ne-(Fumaroyl)diketopiperazine of L-Lys (FDKP) Interactions." Molecular Pharmaceutics, vol. 5, No. 2, 294-315, Accepted and Received 2007, published on web 2008.
Kawai et al. "Evidence that glucagon stimulates insulin secretion through its own receptor in rats." Diabetologia 38:274, 1995.
Kawamori et al. "Does hyperinsulinemia accelerate atherosclerosis?" Department of Medicine, Juntendo University School, vol. 13, No. 12, p. 954-960, 1994.
Kelley, D. et al. "Impaired postprandial glucose utilization in non-insulin dependent diabetes mellitus." Metabolism 13:1549-1557, 1994.
Kenny AJ et al. "Dipeptidyl peptidase IV, a kidney brush-border serin peptidase." Biochem J. 155:169, 1976.
Kim et al. "Development and characterization of a glucagon-like peptide 1-albumin conjugate. The ability to activate the glucagon-like peptide 1 receptor in vivo." Diabetes 52:751, 2003.
Kinzig et al. "The diverse roles of specific GLP-1 receptors in the control of food intake and the response to visceral illness." J Neurosci 22:10470, 2002.
Kirk et al. "Disparities in HbA1c levels between African-American and non-hispanic white adults with diabetes." Diabetes Care 29:2130, 2006.
Kitabchi, Proinsulin and C-peptide:a review. May 26, 1977 (5):547-87, http://www//ncbi.nlm.nih.gov/pubmed/403392.
Klinger et al., Insulin-micro and nanoparticles for pulmonary delivery. International Journal of Pharmaceutics, vol. 377, pp. 173-179 (2009).
Knop et al. "No hypoglycemia after subcutaneous administration of glucagon-like peptide-1 in lean type 2 diabetic patients and in patients with diabetes secondary to chronic pancreatitis." Diabetes Care 26:2581, 2003.
Knop et al. "Reduced incretin effect in type 2 diabetes. Cause or consequence of the diabetic state?" Diabetes 56:1951, 2007.

(56) References Cited

OTHER PUBLICATIONS

Kohler D et al. Non-radioactive approach for measuring lung permeability: inhalation of insulin. Atemw Lungenkrkh 13:230-232, 1987. (English translation attached).
Kohler, "Aerosols for Systemic Treatment", Lung (Suppl.) 677-684 (1990).
Komada et al., Intratracheal delivery of peptide and protein agents: absorption from solution and dry powder by rat lung. J. Pharm. Sci. 83(6): 863-867 (1994).
Komatsu et al. "Glucagonostatic and insulinotropic action of glucagon-like peptide-1 (7-36)-amide." Diabetes 38:902, 1989.
Koning et al., Relationship between inspiratory flow through simulated dry powder inhalers and peak maximal inspiratory pressure. Flow Through a Simulated DPI, Chapter 3, pp. 43-56 (2001).
Labiris et al., Pulmonary drug delivery. Part I: Physiological factors affecting therapeutic effectiveness of aerosolized medications. British Journal of Clinical Pharmocology 56: 588-599 (2003).
Kontny et al., Issues Surrounding MDI Formulation Development with Non-CFC Propellants), J. Aerosol Med 4(3), 181-187 (1991).
Kopple et al. "A convenient synthesis of 2,5-piperazinediones." J Org Chem p. 962, 1967.
Kraft KS, Grant M. Preparation of macromolecule-containing drug powders for pulmonary delivery Methods in Molecular Biology 2009;480:165-174.
Kreymann B et al. "Glucagon-like peptide-1 7-36: a physiological incretin in man." The Lancet, Dec. 5, 1987, p. 1300.
Krssak, M. et al. "Alterations in postprandial hepatic glycogen metabolism in type 2 diabetes." Diabetes 53:3048-3056, 2004.
Krueger et al. "Toxicological profile of pulmonary drug delivery agent." Presented at the American Diabetes Association 64th Scientific Sessions, Jun. 2004, abstract 465-P.
Kwon et al. "Signaling elements involved in the metabolic regulation of mTOR by nutrients, incretins, and growth factors in islets." Diabetes 53:S225, 2004.
Lankat-Buttgereit B et al. "Molecular cloning of a cDNA encoding for the GLP-1 receptor expressed in rat lung." Exp Clin Endocrinol 102:241, 1994.
Laureano et al. "Rapid absorption and elimination of insulin from the lung following pulmonary administration of Technosphere®/Insulin: a pharmacokinetic study in a rat model." Presented at the American Diabetes Association 65th Scientific Sessions, Jun. 2005, abstract 445-P.
Leahy et al. Beta-cell dysfunction in type II diabetes mellitus. Curr Opin Endocrinol Diabetes 2:300-306, 1995.
Lebovitz "Therapeutic options in development for management of diabetes: pharmacologic agents and new technologies." Endocr Pract 12:142, 2006.
Lee et al. "Synthesis, characterization and pharmacokinetic studies of PEGylated glucagon-like peptide-1." Bioconjugate Chem 16:377, 2005.
Lee et al., "Development of an Aerosol Dosage Form Containing Insulin", J. Pharm. Sci. 65(4), 567-572 (1976).
Leiner et al. "Particles facilitate the absorption of insulin in a primary cell culture model of alveolar epithelium without evidence of cytotoxicity." Presented at the American Diabetes Association 64th Scientific Sessions, Jun. 2004, abstract 467-P.
Leiner et al. "The pharmacokinetic profile of insulin administered by inhalation in the rat." Diabetes 53 Supplement, Jun. 2004, A111.
Leone-Bay et al. "Evaluation of novel particles as an inhalation system for GLP-1." Diabetes, Obesity and Metabolism 11:1050-1059, 2009.
Leone-Bay A, Grant M. Technosphere® Technology: A Platform for inhaled protein therapeutics. OndrugDelivery 2006 (published online).
Leone-Bay A, Grant M. Technosphere®/insulin: mimicking endogenous insulin release. In: Rathbone M, Hadgraft J, Roberts M, et al, eds. Modified Release Drug Delivery, 2e. New York, NY: Informa Healthcare USA, Inc; 2008.
Kieffer et al. "The glucagon-like peptides." Endocrine Reviews 20:876, 1999.
Standl et al. "Good Glycemic Control With Flexibility in Timing of Basal Insulin Supply." Diabetes Care, vol. 28, No. 2, Feb. 2005.
Stanley et al. "Gastrointestinal satiety signals III. Glucagon-like peptide 1, oxyntomodulin, peptide YY and pacretic peptide." Am J Physiol Gastrointest Liver Physiol 286:G693, 2004.
Steinberg et al. "A new approach to the safety assessment of pharmaceutical excipients." Reg Toxicol Pharmacol 24:149, 1996.
Steiner et al. "A novel glucagon delivery system for the management of hyperinsulinemia." Diabetes 49 Supplement 1, Abstract 1545-PO, A368, 2000.
Steiner et al. "Bioavailability and pharmacokinetic properties of inhaled dry powder Technosphere®/Insulin." Diabetes 49 Supplement, May 2000, A126.
Steiner et al. "Technosphere®, a novel drug delivery system for oral administration of calcitonin." Pharmaceutical Res 11:5299, 1994.
Steiner et al. Technosphere(TM)/Insulin—proof of concept study with a new insulin formulation for pulmonary delivery. Exp Clin Endocrinol Diabetes, 110:17-21, 2002.
Steiner, K. et al. "The relative importance of first- and second-phase insulin secretion in countering the action of glucagon on glucose turnover in the conscious dog." Diabetes 31:964-972, 1982.
Steiner S, Rave K, Heise T, et al. Pharmacokinetic properties and bioavailablility of inhaled drug powder Technosphere™/insulin. Exp Clin Endocrinol Diabetes 2000; 108:S161.
Steiner S, Rave K, Heise T, et al. Technosphere™/insulin: Bioavailability and pharmacokinetic properties in healthy volunteers. Diabetologia 2000;43:Abstract 511-P.
Steiner SS, Burrell BB, Feldstein R, et Al. Pulmonary delivery of Technosphere™/insulin: Increased bioefficacy and bioavailability in clinical trials using the PDC Medtone™ inhaler. Proceed Int'l Symp Control Rel Bioact Mater 2000; 27: 1000-1001.
Stowell et al. "Development of GLP-1 Technosphere(TM) powder: an inhaled GLP-1 product." Diabetes Technology Meeting, San Francisco, Oct. 2007.
Strack "Inhaled Human Insulin." Drugs of Today 2006, 42 (4): 207-221.
Sturis et al., GLP-1 deriative liraglutide in rats with beta-cell deficiences: influence of metabolic state on beta-cell mass dynamics. British Journal of Pharmacology, 140: 123-132 (2003).
Svartengren et al., Added External Resistance Reduces Oropharyngeal Deposition and Increases Lung Deposition of Aerosol Particles in Asthmatics. Am. J. Respir. Crit. Care Med., vol. 152, pp 32-37, 1995.
Sympatecs. Dry Dispersion for Laser Diffraction and Image Analysis, 2011. XP-002586530.
Leone-Bay et al., Innovation in drug delivery by inhalation. Ondrugdelivery, No. 7, pp. 4-8 (2010).
Tack CJ, Boss AH, Baughman RA, et al. A randomized, double blind, placebo controlled study of the forced titration of prandial Technosphere®/Insulin in patients with type 2 diabetes mellitus. Diabetes 2006;55:Abstract 428-P.
Tack CJ, Christov V, deGalan BE, et al. Randomized forced titration to different doses of Technosphere® insulin demonstrates reduction in postprandial glucose excursions and hemoglobin A1c in patients with type 2 diabetes. J Diabetes Sci Technol 2008; 2(1) :47-57.
Tang-Christensen et al. "Central administration of GLP-1-(7-36) amide inhibits food and water intake in rats." Am J Physiol 271 (Regulatory Integrative Comp Physiol 40):R848, 1996.
Taylor et al. "Aerosols for macromolecule delivery. Design challenges and solutions." Am J Drug Deliv 2:143-155, 2004.
Teeter et al. "Dissociation of lung function changes with humoral immunity during inhaled human insulin therapy." Am J Resp Crit Care Med 173:1194, 2006.
Telko et al., Dry Powder Inhaler Formulation. Respiratory Care, Sep. 2005, vol. 50, No. 9, 1209-1227.
The American Diabetes Association "Insulin Administration" Diabetes Care, vol. 27, Supplement 1, S106-S109 (2004).
Gerber et al., Treatment satisfaction with inhaled insulin in patients with type 1 diabetes. Diabetes Care 24:1556-1559 (2001).
The Lancet. 1989, vol. 333, p. 1235-1236.
Thorens "Expression cloning of the pancreatic b-cell receptor for the gluco-incretin hormone glucagon-like peptide-1." PNAS 89:8641, 1992.

(56) References Cited

OTHER PUBLICATIONS

Thorens B et al. "Cloning and function expression of the human islet GLP-1 receptor: demonstration that exendin-4 is an agonist and exendin-(9-39) an antagonist of the receptor." Diabetes 42:1678, 1993.

Todd et al. "Glucagon-like peptide-1 (GLP-1: a trial of treatment in non-insulin-dependent diabetes mellitus." Eur J Clin Invest 27:533, 1997.

Todd et al. Subcutaneous glucagon-like peptide-1 improves postprandial glucaemic control over a 3-week period in patients with early type 2 diabetes. Clinical Science 95:325, 1998.

Toft-Nielson et al. "Determinants of the effectiveness of glucagon-like peptide-1 in type 2 diabetes." J Clin Endocrinol Metab 86:3853, 2001.

Toft-Nielson et al. "Exaggerated secretion of glucagon-like peptide-1 (GLP-1) could cause reactive hypoglcaemia." Diabetologia 41:1180, 1998.

Toft-Nielson et al. "The effect of glucagon-like peptide-1 (GLP-1) on glucose elimination in healthy subjects depends on the pancreatic glucoregulatory hormones." Diabetes 45:552, 1996.

Tornusciolo D.R. et al., Biotechniques 19(5):800-805, 1995. Simultaneous detection of TDT-mediated dUTP-biotin nick end-labeling (TUNEL)-positive cells and multiple immunohistochemical markers in single tissue sections.

Triantafyllidis et al., Structural, compositional and acidic characteristics of nanosized amorphous or partially crystalline ZSM-5 zeolite based materials. Microporous and Mesoporous Materials, 75:89-100 (2004).

Tu N, Kramer DA, Baughman RA. Inhaled Technosphere® Insulin improves glycemic control without weight gain. Diabetes 2007;56:Abstract 471-P.

Tuley et al., Experimental observations of dry powder inhaler dose fluidisation. International Journal of Pharmaceutics, 358, pp. 238-247 (2007).

Utah Valley University. Saponification. © 2009. Available from: <http://science.uvu.edu/ochem/index.php/alphabetical/s-t/saponification/printpage/>.

Vaczek, Accelerating drug delivery firms exploring new drug-delivery routes and devices intently awaiting the commmercial launch of Exubera. Pharmaceutical & Medical Packaging News, vol. 14, No. 6 (2006).

Vahl et al. "Effects of GLP-1-(7-36)NH2, GLP-1-(7-37), and LPp-1-(9-36)NH2 on intravenous glucose tolerance and glucose-induced insulin secretion in healthy humans." J Clin Endocrinol Metabol 88:1772, 2003.

Van Alfen-Van Der Velden et al. "Successful treatment of severe subcutaneou insulin resistance with inhaled insulin therapy", Pediatric Diabetes 2010: 11:380-382.

Vara E et al. "Glucagon-like peptide-1 (7-36) amide stimulates surfactant secretion in human type II pneumocytes." Am J Resp Crit Care Med 163:840-846, 2001.

Vella A et al. "Effect of glucagon-like peptide 1(7-36) amide on glucose effectiveness and insulin action in people with type 2 diabetes." Diabetes 49:611, 2000.

Vella A et al. "The gastrointestinal tract and glucose tolerance." Curr Opin Clin Nutr Metab Care 7:479, 2004.

Vendrame et al. "Prediabetes: prediction and prevention trials." Endocrinol Metab Clin N Am, 2004, vol. 33, pp. 75-92.

Verdich C, et al., A meta-analysis of the effect of glucagon-like peptide-1 (7-36) amide on ad libitum energy intake in humans. J Clin Endocrinol Metab., 86:4382-4389, 2001.

Vilsboll et al. "Reduced postprandial concentrations of intact biologically active glucagon-like peptide-1 in type 2 diabetic patients." Diabetes 50:609, 2001.

Vilsboll et al. "Similar elimination rates of glucagon-like peptide-1 in obese type 2 diabetic patients and healthy subjects." J Clin Endocrinol Metab 88:220, 2003.

Vilsboll et al., "Evaluation of β-Cell Secretary Capacity Using Glucagon-Like Peptide 1", Diabetes Care, vol. 23, No. 6, pp. 807-812, Jun. 2000.

Vilsboll et al., "Incretin secretion in Relation to Meal Size and Body Weight in Healthy Subjects and People with Type 1 and Type 2 diabetes Mellitus", The Journal of Clinical Endrocronology & Metabolism, vol. 88, No. 6, pp. 2706-2713, 2003.

Kim et al., Dose-response relationships of inhaled insulin delivered via the aerodose insulin inhaler and subcutaneously injected insulin in patients with type 2 diabetes. Diabetes Care, 26:2842-2847 (2003).

Klonoff, David C. M.D., Afrezza inahled insulin: the fastest-acting FDA-approved insulin on the market has favorable properties. Journal of Diabetes Science and Technology, vol. 8(6): 10-71-1073 (2014).

European Search report for European Application 16203266.8 dated Jul. 5, 2017.

Hawe et al., Towards heat-stable oxytocin formulations: Analysis of degradation kinetics and identification of degradation products. Pharmaceutical Research, vol. 26, No. 7, pp. 1679-1688 (2009).

International Search Report and Written Opinion dated Apr. 28, 2017 for International Application No. PCT/US2017/015486 filed on Jan. 27, 2017.

International Application No. PCT/US2017/033627 filed on May 19, 2017.

Journal of Technical Disclosure of Japan Institute of Invention and Innovation; Food Drying Process Techniques; Japan Institute of Invention and Innovation; Independent Administrative Agency; National Center for Industrial Property Information and Training; published Mar. 31, 2005; p. 3-6, 8, 11, and 13 (reference showing well-known technique).

Marconi et al., Chemical composition and nutritional properties of commercial products of mare milk powder. Journal of Food Composition and Analysis 11:178-187 (1998).

Amodeo et al., Pain peptides. Solution structure of orphanin FQ2. FEBS Letters, vol. 473, Issue 2, pp. 157-160 (2000).

Vanderah et al., FE200041 (D-Phe-D-Phe-D-Nle-D-Arg-NH2): A peripheral efficacious k opioid agonist with unprecedented selectivity. The Journal of Pharmacology and Experimental Therapeutics, vol. 310, No. 1, pp. 326-333 (2004).

Krondahl et al., Regional differences in bioavailability of an opioid tetrapeptide in vivo rats after administration to the respiratory tract. Peptides, vol. 23, No. 3, pp. 479-488 (2002).

Lee et al., Intrapulmonary potential of polyethylene glycol-modified glucagon-like peptide-1s as a type 2 anti-diabetic agent. Regulatory Peptides, 152:101-107 (2009).

Selam, Jean-Louis. Inhaled Insulin: Promises and Concerns. Journal of Diabetes Science and Technology, vol. 2, Issue 2, pp. 311-315 (2008).

Fabio et al., Heat-stable dry powder oxytocin formulations or delivery by oral inhalation. AAPS PharmSciTech, (2015).

Lane et al., Influence of post-emulsification drying processes on the microencapsulation of Human Serum Albumin. International Journal of Pharmaceutics, 307: 16-22 (2006).

Mumenthaler et al., Feasibility study on spray-drying protein pharmaceuticals: recombinant human growth hormone and tissue-type plasminogen activator. Pharm Res., 11(1):12-20 (1994).

U.S. Appl. No. 15/640,835, filed Jul. 3, 2017.
Design U.S. Appl. No. 29/553,303, filed Jan. 29, 2016.
Design U.S. Appl. No. 29/553,302, filed Jan. 29, 2016.
Design U.S. Appl. No. 29/553,305, filed Jan. 29, 2016.
Design U.S. Appl. No. 29/553,300, filed Jan. 29, 2016.
U.S. Appl. No. 15/629,636, filed Jun. 21, 2017.
U.S. Appl. No. 15/619,087, filed Jun. 9, 2017.
U.S. Appl. No. 15/445,539, filed Jun. 9, 2017.
Design U.S. Appl. No. 29/579,594, filed Sep. 30, 2016.
Design U.S. Appl. No. 29/604,731, filed May 19, 2017.

* cited by examiner

SUBSTITUTED DIKETOPIPERAZINE ANALOGS FOR USE AS DRUG DELIVERY AGENTS

CROSS-REFERENCE TO RELATED APPLICATIONS

This application is a continuation of U.S. patent application Ser. No. 14/945,168, filed Nov. 18, 2015, which is a divisional of U.S. patent application Ser. No. 14/536,168, filed Nov. 7, 2014, which is a continuation of U.S. patent application Ser. No. 13/649,430, filed Oct. 11, 2012, now U.S. Pat. No. 8,906,926, which is a continuation of U.S. patent application Ser. No. 12/649,210, filed Dec. 29, 2009, now U.S. Pat. No. 8,314,106, which claims priority under 35 U.S.C. § 119(e) to U.S. Provisional Patent Application No. 61/141,207 filed Dec. 29, 2008; the entire contents of each of these applications is incorporated by reference herein.

FIELD OF THE INVENTION

The disclosure is generally in the field of drug delivery systems and relates to the delivery of both small molecule and macromolecular drugs. More specifically, the disclosure relates to novel asymmetric substituted analogues of diketopiperazine (DKP). In one particular embodiment, the diketopiperazine is (E)-3,6-bis[4-(N-carboxyl-2-alkyl)amidoalkyl]-2,5-diketopiperazine (which may also be referred to as diketopiperazine or DKP), their use in the formulation of such drugs including therapeutic, prophylactic and diagnostic agents, stabilizing agents and systems for their delivery is disclosed.

BACKGROUND TO THE INVENTION

Drug delivery systems which allow for efficient absorption of biological agents into the circulation and which increase effective bioavailability of the agent in the circulation for effective therapy are available, but they are not all devoid of potential risks or unwanted side effects. To overcome these challenges, drug delivery systems, such as microparticles and microspheres that are small enough for administration by inhalation in a safe and effective manner have been developed.

For example, microparticles of 2,5 diketopiperazines have been shown to be useful in drug delivery, particularly those bearing acidic R groups (see for example U.S. Pat. No. 5,352,461 entitled "Self Assembling Diketopiperazine Drug Delivery System;" U.S. Pat. No. 5,503,852 entitled "Method For Making Self-Assembling Diketopiperazine Drug Delivery System;" U.S. Pat. No. 6,071,497 entitled "Microparticles For Lung Delivery Comprising Diketopiperazine;" and U.S. Pat. Nos. 6,331,318; 6,395,774; 6,663,898; 6,906,030; and 7,276,534 each entitled "Carbon-Substituted Diketopiperazine Delivery System)" each of which is incorporated herein by reference in its entirety, for all that it teaches regarding diketopiperazines and diketopiperazine-mediated drug delivery). Diketopiperazines can be formed into particles that incorporate a drug or particles onto which a drug can be adsorbed. The combination of a drug with a diketopiperazine can impart improved drug stability and delivery of the active agent. These particles can be administered by various routes of administration. As dry powders these particles can be delivered by inhalation to specific areas of the respiratory system, depending on particle size.

SUMMARY

The disclosure relates to diketopiperazine derivatives, pharmaceutically-acceptable salts thereof, and microparticles thereof for use as a drug delivery system in the delivery of active agents such as therapeutics or prophylactics. In a particular embodiment, the disclosure relates to substituted diketopiperazine wherein the substitution is an asymmetrical substitution at the 3- and 6-position of the diketopiperazine ring so that substituents in the R substituent differs in structure and/or length from the other side chain or pharmaceutically-acceptable salt thereof, having the general structure of Formula A:

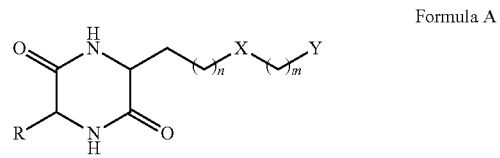

Formula A wherein R is hydrogen or an alkyl group of 1 to 10 carbons;

X is an amide bond, an ester, a sulfone, a sulfoxide, an amine, or a ketone;

n or m represents an integer from 0 to 20; and

Y represents an amide, ester, acid, hydroxyl, phenol, amine, sulfoxide, phosphoric acid, or thiol; wherein n or m can be substituted, unsubstituted, saturated, unsaturated, with and without interrupting heteroatoms, and may contain ring structures (aromatic, non-aromatic, or heterocyclic). In other embodiments, the R group can be substituted, unsubstituted, saturated, unsaturated, with and without interrupting heteroatoms, may contain ring structures (aromatic, non-aromatic, or heterocyclic), and may contain the elements of the other "arm" as long as the elements do not make the DKP symmetrical. In some embodiments, R can be hydrogen or any other substituent as long as the substituent is different from that of the side chain. In some embodiments, n can be any carbon length from 1-10. In certain embodiments, n can be any carbon length from 0-5.

In particular embodiments, the disclosure relates to a substituted diketopiperazine or pharmaceutically-acceptable salt thereof, having the general structure of Formula A wherein R is hydrogen, n equals 3, m is C=C, X is —NHC(O)—, and Y is COOH. In other particular embodiments, the disclosure relates to a substituted diketopiperazine or pharmaceutically-acceptable salt thereof, having the general structure of Formula A wherein R is hydrogen, n equals 2, m is C=C, X is —NHC(O)—, and Y is COOH. In another particular embodiment, the disclosure relates to a substituted diketopiperazine or pharmaceutically-acceptable salt thereof, having the general structure of Formula A wherein R is isopropyl, n equals 3, m is C=C, X is —NHC(O)—, and Y is COOH. In particular embodiments, the pharmaceutically-acceptable salt further comprises at least one cation and the salt is in a powder or granulated form. In some embodiments, the salt is an ester. In some embodiments the salt can be an amorphous powder or crystalline form. In one embodiment, the cation is a monovalent or divalent molecule. In other embodiments, the cation is sodium, lithium, cesium, calcium, magnesium, or potassium.

In certain embodiments, the disclosure relates to therapeutic composition comprising a pharmaceutically-acceptable salt of a substituted diketopiperazine having the general structure of Formula A wherein R is hydrogen or an alkyl group of 1 to 10 carbons; X is an amide bond, an ester, a sulfone, a sulfoxide, an amine, or a ketone; n or m represents an integer from 0 to 20, and in some embodiments an integer from 1-10, and in other embodiments an integer from 0-5; and Y represents an amide, ester, acid, hydroxyl, phenol, amine, sulfoxide, phosphoric acid, or thiol. In another particular embodiment, the disclosure relates to a therapeutic composition comprising a pharmaceutically-acceptable salt of a substituted diketopiperazine having the general structure of Formula A wherein R is hydrogen, n equals 3, m is C═C, X is —NHC(O)—, and Y is COOH. In still another particular embodiment, the disclosure relates to a therapeutic composition comprising a pharmaceutically-acceptable salt of a substituted diketopiperazine having the general structure of Formula A wherein R is hydrogen, n equals 2, m is C═C, X is —NHC(O)—, and Y is COOH. In another particular embodiment, the disclosure relates to a therapeutic composition comprising a pharmaceutically-acceptable salt of a substituted diketopiperazine having the general structure of Formula A wherein R is isopropyl, n equals 3, m is C═C, X is —NHC(O)—, and Y is COOH. In particular embodiments, the pharmaceutically-acceptable salt further comprises at least one cation and the salt is in a powder or granulated form. In some embodiments the salt can be an amorphous powder or crystalline form. In one embodiment, the cation is a monovalent or divalent molecule. In other embodiments, the cation is sodium, lithium, cesium, calcium, magnesium, or potassium. In a further embodiment, the therapeutic composition comprises an active agent. In some embodiments, the active agent is a peptide, protein, polypeptide, small molecule, or nucleic acid molecule. In particular embodiments, the active agent can be selected from the group consisting of insulin, calcitonin, parathyroid hormone 1-34 (PTH 1-34), bioactive fragment of parathyroid hormone, octreotide, leuprolide, and RSV peptide, felbamate, cannabinoid antagonists and/or agonists, muscurinic antagonists and/or agonists, heparin, low molecular weight heparin, cromolyn, sildenafil, vardenafil, tadalafil, growth hormone, AZT, DDI, granulocyte macrophage colony stimulating factor (GM-CSF), peptide YY, oxyntomodulin, lamotrigine, chorionic gonadotropin releasing factor, luteinizing release hormone, β-galactosidase Texas Red, alkynes, cyclosporins, clopidogrel and PPACK (D-phenylalanyl-L-prolyl-L-arginine chloromethyl ketone), antibodies and fragments thereof, including, but not limited to, humanized or chimeric antibodies; F(ab), F(ab)$_2$, or single-chain antibody alone or fused to other polypeptides; therapeutic or diagnostic monoclonal antibodies to cancer antigens, cytokines, infectious agents, inflammatory mediators, hormones, and cell surface antigens, tryptin, GLP-1, exendins 1-4, ghrelin, and fragments thereof. In another embodiment of the disclosure, the active agent is insulin or an analogue thereof.

In some embodiments, the therapeutic composition comprises a precipitate of the pharmaceutically-acceptable salt of a substituted diketopiperazine and an active agent formulated into a solid dosage form suitable for inhalation, or buccal, oral, rectal or vaginal delivery. In other embodiments, the therapeutic composition is formulated in a liquid such as a suspension or solution suitable for transdermal, intravenous or subcutaneous delivery. In another embodiment, the therapeutic composition comprises a dry powder. In particular embodiments, the therapeutic composition is suitable for pulmonary delivery of an active agent.

In other embodiments, the disclosure relates to a microparticle composition comprising a pharmaceutically-acceptable salt of a substituted diketopiperazine having the general structure of Formula A wherein R is hydrogen or an alkyl group of 1 to 10 carbons; X is an amide bond, an ester, a sulfone, a sulfoxide, an amine, or a ketone; n or m represents an integer from 0 to 20, and in some embodiments an integer from 1-10, and in other embodiments an integer from 0-5; and Y represents an amide, ester, acid, hydroxyl, phenol, amine, sulfoxide, phosphoric acid, or thiol. In another particular embodiment, the disclosure relates to a microparticle composition comprising a pharmaceutically-acceptable salt of a substituted diketopiperazine having the general structure of Formula A wherein R is hydrogen, n equals 3, m is C═C, X is —NHC(O)—, and Y is COOH. In still another particular embodiment, the disclosure relates to a microparticle composition comprising a pharmaceutically-acceptable salt of a substituted diketopiperazine having the general structure of Formula A wherein R is hydrogen, n equals 2, m is C═C, X is —NHC(O)—, and Y is COOH. In another particular embodiment, the disclosure relates to a microparticle composition comprising a pharmaceutically-acceptable salt of a substituted diketopiperazine having the general structure of Formula A wherein R is isopropyl, n equals 3, m is C═C, X is —NHC(O)—, and Y is COOH. In particular embodiments, the pharmaceutically-acceptable salt further comprises at least one cation and the salt is in a powder or granulated form. In some embodiments the granulated form can be an amorphous powder or crystalline form. In one embodiment, the cation is a monovalent or divalent molecule. In other embodiments, the cation is sodium, lithium, cesium, calcium, magnesium, or potassium. In another embodiment, the microparticle composition further comprises an active agent.

In further particular embodiment, the disclosure relates to a microparticle composition for delivery of an active agent comprising a pharmaceutically-acceptable salt of a substituted diketopiperazine having the general structure of Formula A wherein R is hydrogen or an alkyl group of 1 to 10 carbons; X is an amide bond, an ester, a sulfone, a sulfoxide, an amine, or a ketone; n or m represents an integer from 0 to 20, and in some embodiments an integer from 1-10, and in other embodiments an integer from 0-5; and Y represents an amide, ester, acid, hydroxyl, phenol, amine, sulfoxide, phosphoric acid, or thiol; the salt further comprises at least one cation and the salt is in a powder or granulated form. In some embodiments the salt can be an amorphous powder or crystalline form. In one embodiment, the cation is a monovalent or divalent molecule. In other embodiments, the cation is sodium, lithium, cesium, calcium, magnesium, or potassium. In another embodiment, the microparticle composition further comprises an active agent such as a peptide, protein, polypeptide, small molecule, or nucleic acid molecule. In still another embodiment, the microparticle composition is formed by precipitation of an active agent onto the substituted diketopiperazine microparticles. In another embodiment, the microparticle composition is formed by precipitation of a solution comprising the substituted diketopiperazine microparticles and the active agent. In a further embodiment, delivery of the microparticle composition is by pulmonary delivery. In particular embodiments, the disclosure relates to a microparticle composition comprising a substituted diketopiperazine having the general structure of Formula A wherein R is hydrogen or an alkyl group of 1 to 10 carbons; X is an amide bond, an ester, a sulfone, a sulfoxide, an amine, or a ketone; n or m represents an integer from 0 to 20, and in some embodiments an integer from 1-10, and in other embodiments an integer from 0-5; and Y represents an amide, ester, acid, hydroxyl, phenol, amine, sulfoxide, phosphoric acid, or thiol; or a pharmaceutical acceptable salt or solvate thereof.

In another particular embodiment, the disclosure relates to a dry powder microparticle composition for delivery of an active agent comprising a pharmaceutically-acceptable salt of a substituted diketopiperazine having the general structure of Formula A wherein R is hydrogen or an alkyl group of 1 to 10 carbons; X is an amide bond, an ester, a sulfone, a sulfoxide, an amine, or a ketone; n or m represents an integer from 0 to 20, and in some embodiments an integer from 1-10, and in other embodiments an integer from 0-5; and Y represents an amide, ester, acid, hydroxyl, phenol, amine, sulfoxide, phosphoric acid, or thiol; the salt further comprises at least one cation and the salt is in a powder or granulated form. In some embodiments the salt can be an amorphous powder or crystalline form. In one embodiment, the cation is a monovalent or divalent molecule. In other embodiments, the cation is sodium, lithium, cesium, calcium, magnesium, or potassium. In some embodiments, the composition further comprises an active agent.

In still a further particular embodiments, the disclosure relates to the method of preparing a dry powder composition for delivery of an active agent to a patient in need thereof comprising: spray drying a solution of an active agent molecule and a pharmaceutically acceptable salt of a substituted diketopiperazine to form a dry powder; wherein the pharmaceutically acceptable salt of a substituted diketopiperazine has the general structure of Formula A wherein R is an alkyl group of 1 to 10 carbons or hydrogen; X is an amide bond, an ester, a sulfone, a sulfoxide, an amine, or a ketone; n or m represents an integer from 0 to 20, and in some embodiments an integer from 1-10, and in other embodiments an integer from 0-5; and Y represents an amide, ester, acid, hydroxyl, phenol, amine, sulfoxide, phosphoric acid, or thiol. In still another embodiment the disclosure relates to the method for preparing a dry powder composition for delivery of an active agent comprising: spray drying a solution of an active agent molecule and a pharmaceutically acceptable salt of a substituted diketopiperazine to form a dry powder; wherein the pharmaceutically acceptable salt of a substituted diketopiperazine has the general structure of Formula A wherein R is hydrogen, n equals 3, m is C═C, X is —NHC(O)— and Y is COOH. In another embodiment the disclosure relates to the method for preparing a dry powder composition for delivery of an active agent comprising: spray drying a solution of an active agent molecule and a pharmaceutically acceptable salt of a substituted diketopiperazine to form a dry powder; wherein the pharmaceutically acceptable salt of a substituted diketopiperazine has the general structure of Formula A wherein R is hydrogen, n equals 2, m is C═C, X is —NHC(O)—, and Y is COOH. In still another embodiment, the disclosure relates to the method for preparing a dry powder composition for delivery of an active agent comprising: spray drying a solution of an active agent molecule and a pharmaceutically acceptable salt of a substituted diketopiperazine to form a dry powder; wherein the pharmaceutically acceptable salt of a substituted diketopiperazine has the general structure of Formula A wherein R is isopropyl, n equals 3, m is C═C, X is —NHC(O)—, and Y is COOH. In another embodiment, the delivery is to the pulmonary system.

In another particular embodiment, the disclosure relates to the method for stabilizing an active agent comprising: spray drying a solution of an active agent molecule and a pharmaceutically acceptable salt of a substituted diketopiperazine to form a dry powder; wherein the pharmaceutically acceptable salt of a substituted diketopiperazine has the general structure of Formula A wherein R is an alkyl group of 1 to 10 carbons or hydrogen; X is an amide bond, an ester, a sulfone, a sulfoxide, an amine, or a ketone; n or m represents an integer from 0 to 20, and in some embodiments an integer from 1-10, and in other embodiments an integer from 0-5; and Y represents an amide, ester, acid, hydroxyl, phenol, amine, sulfoxide, phosphoric acid, or thiol.

BRIEF DESCRIPTION OF THE DRAWINGS

The following drawings form part of the specification and are included to further demonstrate certain aspects described herein. The disclosure may be better understood by reference to one or more of these drawings in combination with the detailed description of specific embodiments presented herein.

DETAILED DESCRIPTION

Figure 1:
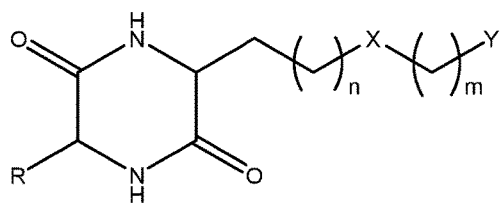
FIG. 1. depicts the general structure of the substituted DKP analogue synthesized.

The disclosure relates to a class of a substituted diketopiperazines (DKPs), characterizable as analogues of (E)-

3,6-bis[4-(N-carboxyl-2-alkyl)amidobutyl]-2,5-diketopiperazine. In certain embodiments, the alkyl is fumaryl, glutaryl, maleyl or succinyl. In certain embodiments the disclosure relates to substituted DKPs of (E)-3,6-bis[4-(N-carboxyl-2-propenyl)amidobutyl]-2,5-diketopiperazine (also referred to as fumaryl diketopiperazine or FDKP). In embodiments of the disclosure, the substituted DKP is an asymmetrical substituted DKP. In certain embodiments the disclosure relates to substituted DKPs, having the general structure of Formula A below, wherein R is hydrogen (H) or an alkyl group of 1 to 10 carbons and n or m=0-20. In some embodiments n or m=0-10. In other embodiments, n or m=0-5. In certain embodiments, n or m=2 or 3.

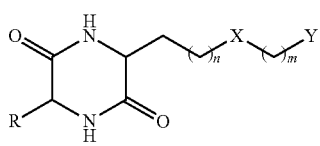

Formula A

The disclosure also relates to other analogues of Formula A wherein m or n can be substituted, unsubstituted, saturated, unsaturated, with and without interrupting heteroatoms, and may contain ring structures (aromatic, non-aromatic, or heterocyclic); X can be in a non-limiting manner an amide, ester, sulfone, sulfoxide, amine, or ketone; Y can be in a non-limiting manner, an amide, acid, ester, hydroxyl, phenol, sulfoxide, amine, phosphoric acid or thiol; and R can be substituted, unsubstituted, saturated, or unsaturated, with and without interrupting heteroatoms, carbon structures, and can contain ring structures for example, aromatic, non-aromatic, or heterocyclic. In some embodiments, R can contain the elements of the other "arm" or side chain as long as the elements do not make the DKP compound symmetrical.

These substituted diketopiperazine compounds have utility as drug delivery agents. Embodiments of the disclosure include microparticles of these DKPs and salts thereof, microparticles comprising these DKPs, that is, the free acid, and microparticles comprising salts of these DKPs. These microparticles further comprise an active agent. The disclosure also embodies methods of making such microparticles, methods of stabilizing active agents by formulating them with these DKPs, and methods of delivering active agents to a subject. The microparticles described herein can be used in other embodiments was diluents, filling agents and the like as known by those skilled in the art. Other embodiments of the disclosure relate to methods of synthesizing these DKPs. More specifically, the disclosure relates to the substituted diketopiperazines: (E)-3-(4-(3,6-dioxopiperazin-2-yl)butylcarbamoyl)-acrylic acid; (E)-3-(3-(3,6-dioxopiperazin-2-yl)propyl-carbamoyl)acrylic acid; and (E)-3-(4-(5-isopropyl-3,6-dioxopiperazin-2-yl)-butylcarbamoyl)acrylic acid, (can also be referred to as asymmetrical "one-armed" analogues of FDKP), for delivery of an active agent or molecule to the pulmonary circulation and into the arterial system in a therapeutically effective manner. This drug delivery system has advantages over other methods of drug delivery, for example, oral, subcutaneous and intravenous administration, in that it circumvents enzymatic deactivation or degradation of drug products (e.g., proteins and peptides) in the gastrointestinal tract, before they reach the target site.

Diketopiperazines and Synthesis of Substituted Diketopiperazine Derivatives

Diketopiperazines are well known in the art for their ability to form microparticles that are useful for drug delivery and stabilization. In the embodiments discussed herein, diketopiperazines are employed to facilitate the absorption of active agents to a target or site of action in the body and avoid degradation of the active agents, for example, in the gastrointestinal tract.

General methods for synthesis and preparation of diketopiperazines are disclosed in U.S. Pat. Nos. 5,352,461; 5,503,852; 6,071,497; 6,331,318; 6,428,771 and U. S. Patent Application No. 20060040953 each incorporated herein by reference in their entirety. Diketopiperazines can be formed by cyclodimerization of amino acid ester derivatives, as described by Katchalski, et al., J. Amer. Chem. Soc. 68:879-80 (1946), by cyclization of dipeptide ester derivatives, or by thermal dehydration of amino acid derivatives in high-boiling solvents, as described by Kopple, et al., J. Org. Chem. 33(2):862-64 (1968), the teachings of which are incorporated herein. 3,6-di(aminobutyl)-2,5-diketopiperazine (Katchalski et al. refer to this as lysine anhydride) was prepared via cyclodimerization of N-epsilon-P-L-lysine in molten phenol, similar to the Kopple method in J. Org Chem., followed by removal of the blocking (P)-groups with 4.3 M HBr in acetic acid. In an embodiment, this route is utilized because it uses a commercially available starting material, it involves reaction conditions that are reported to preserve stereochemistry of the starting materials in the product and all steps can be easily scaled up for manufacture.

The term "microparticle" refers to a particle with a diameter of about 0.5-1000 µm, irrespective of the precise exterior or interior structure. Within the broad category of microparticles, "microspheres" refer to microparticles with uniform spherical shape. Crystalline microparticles refer to microparticles that have the internal structure, though not necessarily the external form, of a crystal and have a regular arrangement of atoms in a space lattice. Ionizable crystalline surfaces refer to crystalline microparticles that have the additional capacity to carry an electrical charge. In some instances, the microparticle can be a single regularly shaped crystal. In various embodiments the microparticle is irregularly shaped, is porous, has dissolved active agent-accessible interior surfaces, or comprises multiple crystals, in any combination. These characteristics generally increase surface area of the microparticles and thereby absorption capacity.

In a particular embodiment, the disclosure relates to microparticles comprising substituted diketopiperazines and microparticles comprising pharmaceutically-acceptable salts of substituted diketopiperazines. General methods for synthesis and preparation of substituted diketopiperazines are disclosed in U.S. Pat. No. 5,503,852, incorporated herein by reference in their entirety.

One method for preparing substituted diketopiperazine analogues is to protect functional groups on the side chain, selectively deprotect one of the side chains, then react the deprotected functional group with an appropriate reagent. The second side-chain functional group is then deprotected and reacted with a different reagent to form the substituted analogue, such as for example, an asymmetrical analogue. Diketopiperazine derivatives with protected basic side chains, such as cyclo-Lys(P)Lys(P), wherein P is a benzyloxycarbonyl group, or other protecting group, can be partially deprotected by limiting exposure to the deprotective reagent, such as, for example, HBr in the case of the benzyloxycarbonyl group, and/or by using controlled time intervals. In this manner, reaction mixtures which contain unprotected, monoprotected and di-protected diketopiperazine derivatives can be obtained. These compounds have different solubilities in various solvents and pH ranges, and can be separated by selective precipitation and removal.

In addition to the above method for preparing substituted diketopiperazines by altering the side chains of a symmetrical diketopiperazine, the reaction of two different amino acids may also be employed to obtain a diketopiperazine that is asymmetrical. In this method, two different, appropriately protected amino acids are first coupled to form a linear dipeptide. The alpha amino and carboxylic acid groups are then deprotected, and then reacted with each other to give the diketopiperazine ring structure.

The term "protecting group" as used herein refers to a moiety which blocks a functional group from reaction, and which is cleavable when there is no longer a need to protect the functional group. Functional groups can include, in a non-limiting manner, hydroxy, thio, amine, keto, carboxy, alkenyl, alkynyl, carbonyl, and phosphorus derivatives such as phosphate, phosphonate and phosphinate in the diketopiperazines or material to be covalently attached to the diketopiperazines, that is not involved in coupling to form an ester, thioester, amide or sulfamide bond. Suitable protecting groups for the hydroxyl group include certain ethers, esters and carbonates (Greene, T. W. and Wuts, P. G. M., "Protective groups in organic synthesis," John Wiley, New York, 2nd Ed. (1991)). Suitable protecting groups for the carboxyl group include those described in Green and Wuts, Protecting Groups in Organic Synthesis, John Wiley (1991). Examples of protecting groups for amine groups include t-butyloxycarbonyl (Boc), benzyloxycarbonyl (Cbz). Side-chain functionalities such as carboxylic acids, alcohols, and amines may interfere with the coupling chemistry and must be appropriately protected.

In other particular embodiments, the disclosure relates to microparticles comprising pharmaceutically-acceptable salts of substituted diketopiperazines for delivery of an active agent to the pulmonary system. The use of diketopiperazine salts for the delivery of an active agent is described in U.S. patent application Ser. No. 11/210,709 (Patent Publication No. 20060099269), entitled "Pulmonary Delivery of Inhibitors of Phosphodiesterase Type 5"; and U.S. patent application Ser. No. 11/210,710, (Patent Publication No. 20060040953) entitled "Diketopiperazine Salts for Drug Delivery and Related Methods", both filed on Aug. 23, 2005 and incorporated herein by reference in their entirety for all they contain regarding diketopiperazine salts.

The diketopiperazine salts of the disclosure can be prepared by reacting the diketopiperazine free acid with a solution of an appropriate base, (for example, sodium hydroxide). In some embodiments, the salt is a pharmaceutically acceptable organic or inorganic salt. The salt may be a mono-, di-, or mixed salt. The salt can be sodium (Na), or cesium, potassium (K) for example. In some embodiments, the salt can be an inorganic or organic molecule. In some instances, a basic form of the active agent may be mixed with the diketopiperazine microparticles in order to form a drug salt of the diketopiperazine, such that the drug is the counter cation of the diketopiperazine. Salts as referred to herein can be in a solid form such as, but not limited to, granulated or powder form. In other embodiments, the salt can be an ester. In other embodiments the salt can be an amorphous powder or a crystalline composition.

Thus, using the methodology described above and as in Example 1 herein, the inventors obtained a group of substituted diketopiperazine compounds that readily self-assemble into microparticles for use as drug delivery agents. These novel substituted diketopiperazine compounds are: (E)-3-(4-(3,6-dioxopiperazin-2-yl)butylcarbamoyl)-acrylic acid; (E)-3-(3-(3,6-dioxopiperazin-2-yl)propyl-carbamoyl) acrylic acid; and (E)-3-(4-(5-isopropyl-3,6-dioxopiperazin-2-yl)-butylcarbamoyl)acrylic acid.

It is noted that while diketopiperazines may generally form self-assembling particles as disclosed in U.S. Pat. No. 5,503,852, each and every particular species may not exhibit the ability to form such particles, which is a key characteristic of the compounds disclosed herein. Examples of diketopiperazines that do not form self-assembling particles have been disclosed by Beregon et al., (*J Am. Chem. Soc.*, 116(19): 8479-8484:1994, *Macromolecular Self-assembly of Diketopiperazine Tetrapeptides*) and include: a diketopiperazine of $_L$-glutamic acid, a diketopiperazine of $_L$-aspartic acid, Gly-(diketo-$_L$-Asp)-Gly, $_L$-Ala(diketo-$_L$-Asp)-$_L$-Ala, $_L$-Val(diketo-$_L$-Asp)-$_L$-Val, $_L$-Tyr(diketo-$_L$-Asp)-$_L$-Tyr, $_L$-Phe(diketo-$_L$-Glu)-$_L$-Phe, and $_L$-Phe-$_L$-Phe (diketo-$_L$-Asp)-$_L$-Phe-$_L$-Phe. In addition, Kaur et al., (*Mol. Pharmaceutics*, 5 (2), 294-315, 2008), have shown that N-Et FDKP (3-{[4-(5-{4-[(3-carboxyacryloyl)ethylamino]butyl}-3,6-dioxopiperazin-2-yl)butyl]ethylcarbamoyl}acrylic acid) does not readily form microparticles.

Active Agents

In another embodiment of the disclosure, the substituted diketopiperazines described above have utility as delivery systems for the delivery of active agents to a target or site in the body. The term 'active agent' is referred to herein as the therapeutic agent, or molecule (such as protein or peptide or biological molecule), to be encapsulated, associated, joined, complexed or entrapped in or to the substituted diketopiperazine of the disclosure. Generally speaking, any form of an active agent can be combined with the microparticles discussed. For drug delivery, biologically active agents having therapeutic, prophylactic or diagnostic activities can be delivered using the substituted diketopiperazines disclosed herein.

Active agents for use in the compositions and methods described herein can include any polymer or large organic molecules, or peptides and proteins. These can include, for example, synthetic organic compounds, polysaccharides and other sugars, lipids, and nucleic acid sequences, having therapeutic, prophylactic, or diagnostic activities. Peptides, proteins, and polypeptides are all chains of amino acids linked by peptide bonds. The term 'polypeptide' as used herein, can refer to a peptide, a protein, or any other chain of amino acids of any length containing multiple peptide bonds, though generally containing at least 10 amino acids. Peptides are generally considered to be less than 30 amino acid residues but may include more. Proteins are polymers that can contain more than 30 amino acid residues. Proteins as referred to herein can also include subunits and whole proteins with multi-subunit components, at least more than one subunit or monomer of natural, synthetic or recombinant origin.

Active agents for delivery by the substituted diketopiperazine compounds described can also include small molecules and vitamins, and agents that regulate metabolism, weight, or blood glucose levels. Biological agents that are unstable in gastric acid, diffuse slowly through gastrointestinal membranes, and/or are susceptible to enzymatic destruction, for example, in the gastrointestinal tract can be delivered with the substituted diketopiperazines described herein, to more efficiently reach the target locus and retain their biological activity.

Additional examples of active agents that can be delivered to a target or site in the body using the substituted diketopiperazine microparticles described herein, include hormones, particularly endocrine hormones; anticoagulants, immunomodulating agents, cytotoxic agents, antibiotics, vasoactive agents, neuroactive agents, anesthetics or sedatives, steroids, decongestants, antivirals, antisense, antigens, and antibodies. More particularly, these compounds include insulin, heparin, calcitonin, felbamate, glucagon, glucagon like peptide 1 (GLP-1), parathyroid hormone and fragments thereof, parathyroid hormone related peptide (PTHrP), tryptin, growth hormone, erythropoietin, AZT, DDI, granulocyte macrophage colony stimulating factor (GM-CSF), lamotrigine, chorionic gonadotropin releasing factor, luteinizing releasing hormone, beta-galactosidase, exendin and argatroban. Antibodies and fragments thereof can include, in a non-limiting manner, anti-SSX-2$_{41-49}$ (synovial sarcoma, X breakpoint 2), anti-NY-ESO-1 (esophageal tumor associated antigen), anti-PRAME (preferentially expressed antigen of melanoma), anti-PSMA (prostate-specific membrane antigen), anti-Melan-A (melanoma tumor associated antigen) and anti-tyrosinase (melanoma tumor associated antigen).

In particular embodiments of the disclosure, the active agent can be insulin or an analogue thereof. Insulin analogues with faster, slower, shorter, or longer action profiles are known in the art. Such analogues include those with altered amino acid sequences and those that have been covalently modified with other moieties, such as polyethylene glycol, or additional amino acids, such as in a fusion protein. Ultimately any molecule with a substantial portion of a wild type insulin molecule and physiologically relevant insulin activity is comprehended by this term.

Formulations of Substituted DKP Microparticles and Active Agent Molecules

In particular embodiments, the disclosure relates to a microparticle composition for delivery of an active agent comprising a pharmaceutically-acceptable salt of an substituted diketopiperazine. In other embodiments, the disclosure relates to a dry powder composition comprising a pharmaceutically-acceptable salt of substituted diketopiperazine particles with an active agent. Dry powders can be prepared by spray drying a solution of an active agent molecule and a pharmaceutically acceptable salt of a substituted diketopiperazine to form the dry powder.

The substituted diketopiperazine particles described herein can be formed and loaded with active agent by a variety of methods as taught in U.S. patent application Ser. No. 11/532,063 (U.S. Publication No. 20070059373), entitled "Method of Drug Formulation Based on Increasing the Affinity of Active Agents for Crystalline Microparticle Surfaces" and U.S. patent application Ser. No. 11/532,065 (U.S. Publication No. 20070059374) entitled "Method of Drug Formulation Based on Increasing the Affinity of Active Agents for Crystalline Microparticle Surfaces"; each incorporated herein by reference in its entirety.

A solution of substituted diketopiperazine can be mixed with a solution or suspension of an active agent and then precipitated to form particles comprising the active agent. The active agent molecule can be encapsulated within microparticles by dissolving a diketopiperazine with acidic side chains in bicarbonate or other basic solution, adding the solution or suspension of active agent to be encapsulated, then precipitating the diketopiperazine to form microparticles by adding acid, such as citric acid. In instances where the diketopiperazine has basic side chains, the active agent molecule can be encapsulated within microparticles by dissolving a diketopiperazine in an acidic solution, such as citric acid, adding the solution or suspension of drug or active agent to be encapsulated, then precipitating the diketopiperazine to form microparticles by adding bicarbonate or other basic solution. Where the diketopiperazine has both acidic and basic side chains, the active agent molecule can be encapsulated within microparticles by dissolving the diketopiperazine in an acidic or basic solution, adding the solution or suspension of drug or active agent to be encapsulated, then precipitating the diketopiperazine to form microparticles by neutralizing the solution. Alternatively the substituted diketopiperazine can be precipitated to form particles and subsequently mixed with a solution of the active agent. Association between the substituted diketopiperazine particle and the active agent can be driven by solvent removal or a specific step can be included prior to drying to promote the association. Such a step can include a pH adjustment to promote the absorption/association of the active agent onto the substituted diketopiperazine. In a particular embodiment of the disclosure, the microparticles are formed by spray drying the diketopiperazine and active agent from a solution or suspension.

In a particular example, a composition or formulation comprising a substituted diketopiperazine and insulin can be prepared by precipitating substituted diketopiperazine particles; the precipitated substituted diketopiperazine particles are then washed, and a solution or suspension of insulin is added. Adsorption of insulin to the particle is promoted by adjusting the pH of the solution, and solvent removed by spray drying to obtain a dry powder comprising a substituted diketopiperazine with insulin.

In further particular embodiments, a method of preparing a dry powder composition for delivery of an active agent to a patient in need thereof is disclosed, comprising: spray drying a solution of an active agent molecule and a pharmaceutically acceptable salt of a substituted diketopiperazine to form a dry powder. The use of spray drying for the formation of dry particulate pharmaceuticals is known in the art (see for example, US Patent Publication No. 20070196503 (U.S. patent application Ser. No. 11/678,046) filed on Feb. 22, 2006 and entitled "A Method for Improving the Pharmaceutic Properties of Microparticles Comprising Diketopiperazine and an Active Agent" incorporated herein by reference for all it contains regarding spray drying; and for example, U.S. Pat. Nos. 5,976,574; 5,985,248; 6,001,336; 6,051,256; 6,077,543; 6,365,190; 6,372,258; 6,423,344; 6,479,049; 6,509,006; 6,569406; 6,572,893; 6,582,728; 6,838,076; and 6,896,906). In brevity, spray drying, is a thermal processing method used to load and/or dry particulate solids from a variety of solutions or suspensions. During spray drying, the aqueous mixture (a solution or suspension) of substituted diketopiperazine particles or substituted diketopiperazine-active agent particles, is formed into droplets through aerosolization and then passed through a heated gas stream having sufficient heat energy to evaporate water and solvents in the particles, thereby producing dry powder compositions. The resulting dry powder is of homogeneous constitution having a particle size that is respirable, with low moisture content and other characteristics that allow for aerosolization.

Administration of Therapeutic Formulations of Substituted Diketopiperazines

The disclosure relates to pharmaceutical compositions comprising substituted diketopiperazine salts and active agents that can be delivered to a target or site in the body. In particular embodiments, an active agent such as insulin, for example, can be delivered by inhalation to specific areas of the respiratory system, by the drug delivery agents described herein. More particularly, dry powder compositions comprising a substituted diketopiperazine with an active agent are suitable pulmonary delivery. Pulmonary delivery can lead to quicker absorption into the systemic blood circulation and/or delivery in the lung. Direct delivery of the pharmaceutical composition into the pulmonary circulation and into the arterial system, avoids, circumvents or delays degradation or deactivation of active agents, (e.g., peptides), by enzymes or other mechanisms in the local peripheral and/or venous vasculature of the lungs, and increases its effective bioavailability. Therefore, with drug delivery systems described herein, effective lower dosages of a pharmaceutical substance can be delivered, for example, by pulmonary administration instead of higher dosages that are often required with other routes of administration in order to achieve delivery of the effective amount to the target site. This method can also provide a route for reducing metabolite formation and therefore, a reduction in toxicity or side effects from products delivered into a patient by other routes. In some aspects, the pulmonary drug delivery system is not limited to delivery of peptides, but can be used with other types of pharmaceutical substances that can be rapidly metabolized and/or degraded by direct contact with the local degradative enzymes in the peripheral or vascular venous tissue as encountered with other routes of administration such as oral, intravenous, transdermal, and subcutaneous administration.

In one embodiment, the dry powder composition delivers insulin in a biologically active form to a patient, which provides a spike of serum insulin levels, which simulates the normal response to eating. In some embodiment, the patient is a human suffering from Type II diabetes. The Examples below show administration of various substituted diketopiperazines compounds loaded with insulin formulations to a subject by pulmonary insufflation, which leads to a reduction in glucose levels and a spike of serum insulin levels.

Additionally, the particles containing an active agent can be made small enough for incorporation into an intravenous suspension dosage form. The substituted diketopiperazine and active agent compositions described can be administered as a liquid or solid form. These can include solutions, suspensions, dry powders, tablets, capsules, suppositories, patches for transdermal delivery, and the like. These different forms offer distinct, but overlapping advantages. The solid forms provide convenient bulk transport of active agents and can improve their stability. They can also be formed into microparticles enabling administration by inhalation specifically to the nasal mucosa or deep lung, depending on the size of the microparticle. For oral delivery the compositions disclosed herein can be incorporated into a suspension, tablets or capsules.

The compositions of the disclosure can be administered to any targeted biological membrane, such as, for example, a mucosal membrane of a patient. For parenteral administration, formulations, described herein, of less than five microns readily pass through a needle for intravenous administration. Similarly, substituted diketopiperazine and active agent compositions can be injected or implanted subcutaneously, intramuscularly, or intraperitoneally. Additionally, the formulations described herein can be placed in an implantable device to facilitate sustained and/or controlled delivery. For topical or transdermal administration, formulations can be suspended in a suitable pharmaceutical carrier for administration using methods appropriate for the carrier and site of administration. The substituted diketopiperazine microparticles or aggregations of microparticles into films, disks, or tablets, with the loaded active agent can be administered to the skin in an ointment, cream, or patch. Suitable pharmaceutical carriers, for example, phosphate buffered saline, are known and commercially available. Mucosal administration, including buccal, vaginal, rectal, nasal administration is also contemplated herein.

The compositions described herein, are can be stored in a dry powder form until immediately before administration. The dry powder formulations can then be administered directly, such as by inhalation, using dry powder inhalers. Dry powder inhalers are known in the art and particularly suitable inhaler systems are described in U.S. Pat. No. 7,305,986 and U.S. Patent Application Publication No. 20040182387 (patent application Ser. No. 10/655,153), both entitled "Unit Dose Capsules and Dry Powder Inhaler", which are hereby incorporated by reference in their entirety. Pulmonary delivery using diketopiperazine microparticles can be found in U.S. Pat. No. 6,428,771 entitled "Method for Drug Delivery to the Pulmonary System," which is hereby incorporated by reference in its entirety. The formulation of substituted diketopiperazine with an active agent discussed herein may be delivered from an inhalation device, such as a nebulizer, a metered-dose inhaler, a dry powder inhaler, and a sprayer. Alternatively, the microparticles can be suspended in a sufficient volume of pharmaceutical carrier, for example, as an aqueous suspension for administration as an aerosol.

The term "powder" means a composition that consists of fine solid particles that are capable of being dispersed in an inhalation device and inhaled by a subject. In one embodiment, the particles reach the lungs or alveoli. Such a powder is said to be "respirable." In another embodiment, the average particle size is less than about 10 microns (μm) in diameter with a relatively uniform spheroidal shape distribution. In yet another embodiment, the diameter is less than about 7.5 μm and can be less than about 5.0 μm. Usually the particle size distribution is between about 0.1 μm and about 8 μm in diameter, particularly about 0.3 μm to about 5 μm.

The term "dry" means that the powder composition is not suspended or dissolved in a propellant, carrier, or other liquid. It is not meant to imply a complete absence of water. The composition can have a moisture content such that the particles are readily dispersible in an inhalation device to form an aerosol. This moisture content is generally below about 10% by weight (% w) water, usually below about 5% weight and can be less than about 3% weight.

The term "effective amount" is the amount that is needed to provide a desired response in the subject to be treated. The precise dosage will vary according to a variety of factors including, but not limited to, the age and size of the subject, the disease and the treatment being affected. The "effective amount" will also be determined based on the anticipated pharmacodynamic response. In further embodiments, administration of an "effective amount" of a formulation of a substituted diketopiperazine with an active agent to a patient in need thereof is contemplated. An "effective amount" of a substituted diketopiperazine and an active agent formulation as contemplated herein, refers to that amount of the active agent being administered which will relieve to some extent one or more of the symptoms of the disease, condition or disorder being treated. In one embodiment an "effective amount" of a substituted diketopiperazine and an active agent dry powder formulation would be that amount of the active agent molecule for treating a disease or disorder or condition such as, but not limited to, diabetes for example, by increasing plasma insulin levels, reducing or lowering fasting blood glucose levels.

EXAMPLES

The following examples are included to demonstrate particular embodiments of the disclosure. It should be appreciated by those of skill in the art that the techniques disclosed in the examples elucidate representative techniques that function well in the practice of the invention, and thus can be considered to constitute preferred modes for its practice. However, those of skill in the art should, in light of the disclosure, appreciate that many changes can be made in the specific embodiments which are disclosed and still obtain a like or similar result without departing from the spirit and scope herein.

Example 1

Synthesis of Substituted DKP Analogs

Preparation of diketopiperazine microparticles cyclo-Lys (Z)-Lys(Z) has been disclosed in U.S. Pat. No. 5,352,461, incorporated herein by reference in its entirety. This process involves the steps of: cyclodimerization of N-epsilon-(Z)-L-lysine, protection of the amino group, and deprotection of Lys(Z)-Lys(Z).

Substituted diketopiperazines particles described herein were prepared by the reaction of two different amino acids of a symmetrical diketopiperazine such as FDKP. In this method, two different, appropriately protected amino acids are first coupled to form a linear dipeptide. The alpha amino and carboxylic acid groups are then deprotected, and then reacted with each other to give the diketopiperazine ring structure.

Using this methodology, the inventors prepared a group of substituted diketopiperazine formulations that readily self-assemble into microparticles for use as delivery agents. Examples of these substituted diketopiperazine compounds are shown in Table 1. The general structure of these compounds is illustrated below as Formula A (FIG. 1).

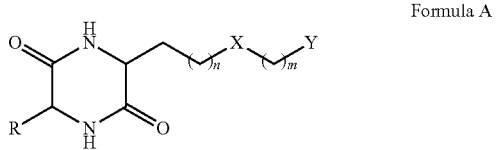

Formula A

TABLE 1

Substituted diketopiperazine Compounds

| Compound | Compound Name | R | n |
|---|---|---|---|
| 3 | (E)-3-(4-(3,6-dioxopiperazin-2-yl)butylcarbamoyl)-acrylic acid | H | 3 |
| 4 | (E)-3-(3-(3,6-dioxopiperazin-2-yl)propyl-carbamoyl)acrylic acid | H | 2 |
| 5 | (E)-3-(4-(5-isopropyl-3,6-dioxopiperazin-2-yl)-butylcarbamoyl)acrylic acid | $CH(CH_3)_2$ | 3 |

Figure 2:
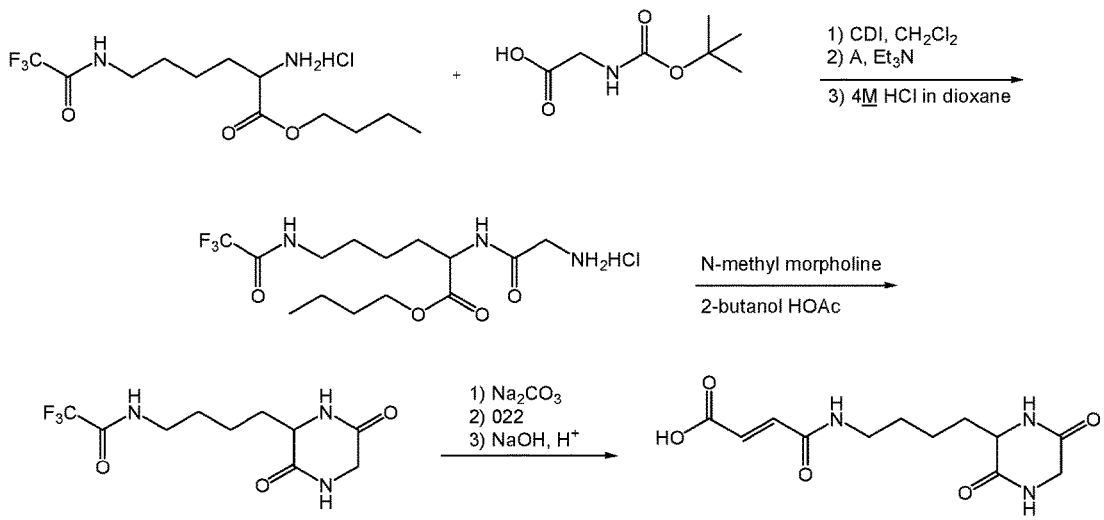
FIG. 2. depicts the initial route of synthesis of the substituted DKP analogue (E)-3-(4-(3,6-dioxopiperazin-2-yl)butylcarbamoyl)-acrylic acid.
Figure 3:
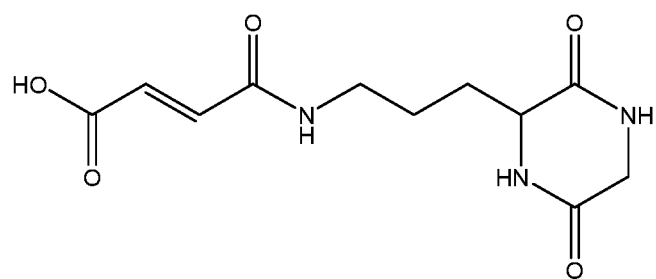
FIG. 3. depicts the structure of the substituted DKP analogue ((E)-3-(3-(3,6-dioxopiperazin-2-yl)propyl-carbamoyl)acrylic acid.
Figure 4:
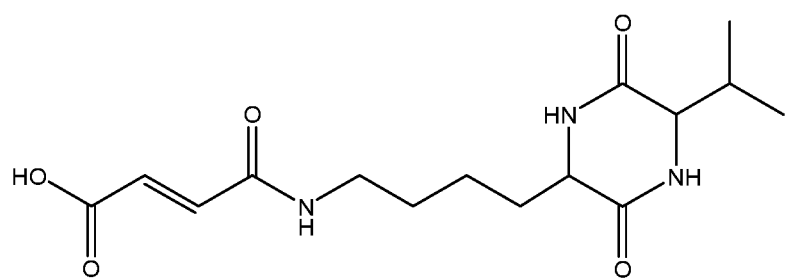
FIG. 4. depicts the structure of the substituted DKP analogue (E)-3-(4-(5-isopropyl-3,6-dioxopiperazin-2-yl)-butylcarbamoyl)acrylic acid.

In one embodiment, the synthesis of the asymmetrically substituted diketopiperazine (E)-3-(4-(5-isopropyl-3,6-dioxopiperazin-2-yl)-butylcarbamoyl)acrylic acid (Compound 3, Table 1; FIG. 4), via coupling of the appropriately protected glycine and lysine amino acids is illustrated below (FIG. 2). FIGS. 3 and 4 depict Compounds 4 and 5 respectively. Test powders for in vivo evaluation were prepared by spray drying as described elsewhere herein.

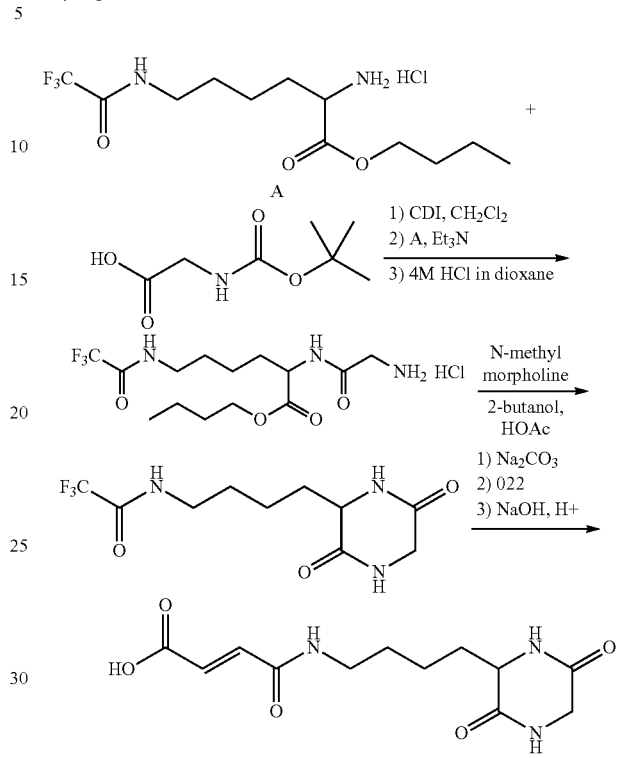

Example 2

Pharmacokinetics of GLP-1/DKP Analogues Administered Via Pulmonary Insufflation in Rats To determine whether different DKPs (also referred to as xDKPs or substituted DKPs, or asymmetrical substituted DKPs) may influence the pharmacokinetic profile of GLP-1/FDKP formulations, various GLP-1/xDKP substituted analogue formulations were made and administered to rats via pulmonary insufflation.

Animals were divided into 6 treatment groups consisting of five animals per group. The control group (n=3) received GLP-1 via liquid instillation. GLP-1/FDKP (0.3 mg GLP-1), administered by pulmonary insufflation, was also used as a second control. Each of the GLP-1/xDKP treated groups received GLP-1/DKP formulations via pulmonary insufflation at ~2.0 mg doses of xDKP containing GLP-1 at 10% and 15%. The substituted diketopiperazines (xDKPs) used were: (E)-3-(4-(3,6-dioxopiperazin-2-yl)butylcarbamoyl)-acrylic acid, (3,6-bis(4-carboxypropyl)amidobutyl-2,5-diketopiperazine), and ((E)-3,6-bis(4-(carboxy-2-propenyl)amidobutyl)-2,5-diketopiperazine disodium salt) loads. Whole blood was collected for evaluation of GLP-1 concentrations at 5, 10, 20, 30, 45, 60 and up to 90 minutes post dose.

Based on the preliminary analysis with insulin, the GLP-1/xDKP formulation have been shown to have comparable or better pharmacokinetics than GLP-1/FDKP and/or Exendin/FDKP (data not shown).

Example 3

Glucose Reduction in Rats Administered xDKP/Insulin (TI) Powders

Figure 5:
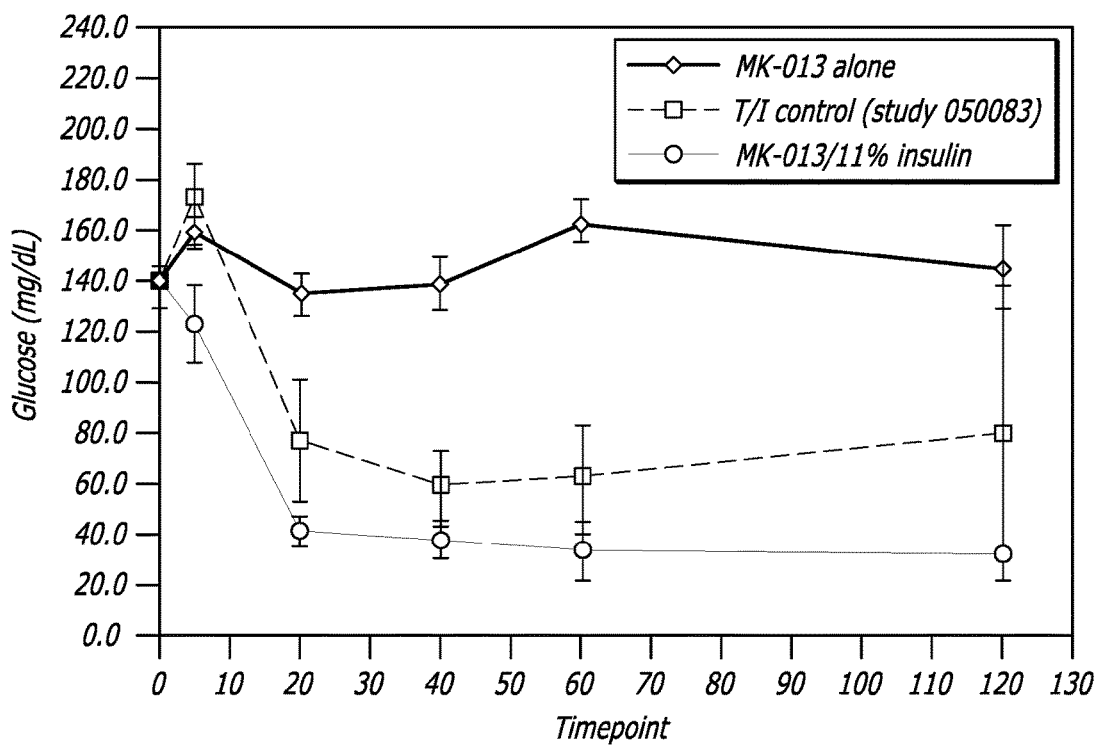
FIG. 5. depicts glucose reduction upon administration by pulmonary insufflation to female rats of a formulation of insulin (11%) with the pharmaceutically-acceptable salt of a substituted DKP analogue (E)-3-(4-(3,6-dioxopiperazin-2-yl)butylcarbamoyl)-acrylic acid, compared to the DKP analogue (E)-3-(4-(3,6-dioxopiperazin-2-yl)butylcarbamoyl)-acrylic acid alone (also referred to herein as Compound 3); and a control containing DKP with insulin (11%).

An initial study was conducted to determine whether substituted DKP/insulin powders have an effect on the pharmacokinetic or pharmacodynamic profiles of rats administered these powders. For this study, a substituted DKP/insulin powders were prepared containing (E)-3-(4-(3, 6-dioxopiperazin-2-yl)butylcarbamoyl)-acrylic acid (referred to herein as Compound 3 (MK-013 alone); table 1 above) and Compound 3 formulated with insulin (MK-013/; 11% load) as the active ingredient, and administered to rats via pulmonary insufflation. Formulation containing Compound 3 alone was administered to a control group of rats and an additional group of rats received a formulation comprising a symmetrically substituted diketopiperazine (E)-3,6-bis[4-(N-carboxy-2-propenyl)amidobutyl]-2,5-diketopiperazine, (FDKP) and insulin (11% load) (TI control) by pulmonary insufflation. Blood samples were taken on the day of dosing for each rat per group at pre-dose (0 minutes), 5, 20, 40, 60, and 120 minutes post dose. At each time point, approximately 104 of whole blood was collected from the lateral tail vein of rats in each group and analyzed for glucose levels using a monitor glucose strip. The results illustrate that rats administered a dry powder composition containing Compound 3 and insulin exhibited the lowest blood glucose levels as depicted in FIG. 5. At 20 minutes post dose, the blood glucose level was 40 mg/dL from a pre-dose level of 140 mg/dL. At 1 hour and 2 hours post dose, the blood glucose level was about 35 mg/dL and 33 mg/dL respectively. Rats administered the formulation of Compound 3/insulin powder exhibited about a 2 fold to about a 4 fold reduction in the blood glucose level as compared to the groups administered formulation containing Compound 3 alone or FDKP/insulin (TI).

Example 4

Insulin Analysis in Rats Administered Substituted DKP/Insulin

Figure 6:
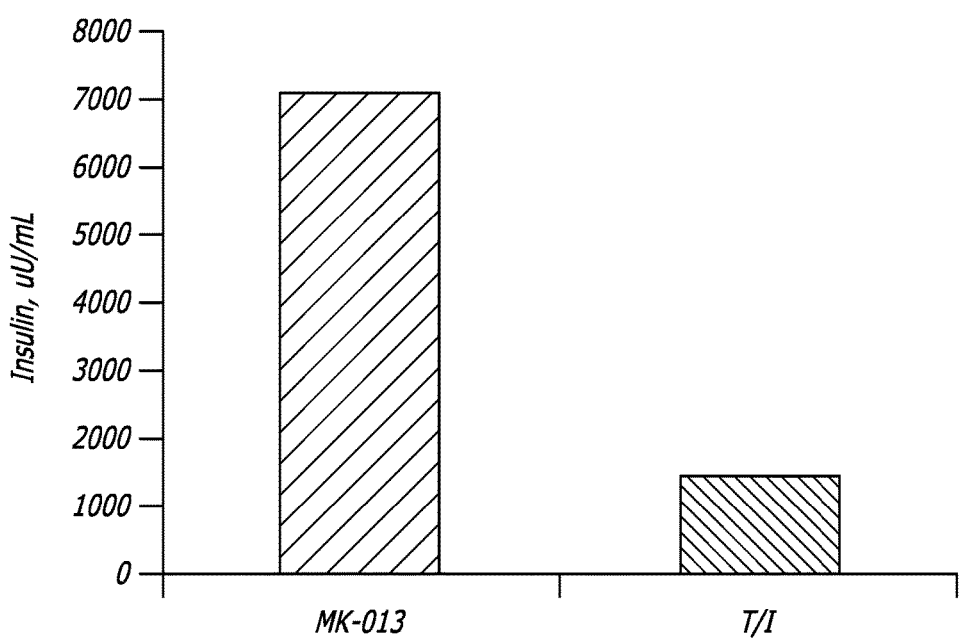
FIG. 6. depicts serum insulin levels upon administration by pulmonary insufflation to female rats of a formulation of insulin (11%) with the pharmaceutically-acceptable salt of a substituted DKP analogue (E)-3-(4-(3,6-dioxopiperazin-2-yl)butylcarbamoyl)-acrylic acid, compared to a control formulation of insulin (11%) with DKP.

Animals were treated as described in the Example above and serum insulin levels determined. Blood samples were taken on the day of dosing for each rat per group at pre-dose and 20 minutes post dose. At each time point, approximately 150 µL of whole blood was collected from the lateral tail vein of rats in each group and analyzed for insulin levels by ELISA. As depicted in FIG. 6 serum levels were about 3.5 fold higher for the group receiving the formulation of (E)-3-(4-(3,6-dioxopiperazin-2-yl)butylcarbamoyl)acrylic acid with insulin (11% load)) compared to the control group receiving FDKP/insulin (TI). The data indicate that Compound 3 may be more effective in delivering insulin to the rat circulation than the formulation comprising FDKP.

Example 5

Glucose and Insulin Analysis in Rats Administered Substituted DKP Powders

To determine whether different DKPs may influence the pharmacokinetic profile of xDKP/insulin formulations various DKP and insulin powders were tested. For this study, a substituted diketopiperazine/insulin powder was prepared containing (E)-3-(4-(3,6-dioxopiperazin-2-yl)butylcarbam-oyl)-acrylic acid (Compound 3, Group rats) and Compound 3 with 10.6% insulin content (Formulation 3). Dry powders compositions of symmetrical substituted diketopiperazine and insulin were also prepared containing either 3,6-bis[(N-carboxypropyl)amidobutyl]-2,5-diketopiperazine (Compound 1) and a formulation of Compound 1 with an insulin content of 10.7%, (Formulation 1), or (E)-3,6-bis[(N-carboxy-2-propenyl)-amidopropyl]-2,5-diketopiperazine (Compound 2) and and Compound 2 with insulin at a 10.5% content (Formulation 2). Each of Compounds 1 (Group 1), 2 (Group 2) or 3 (Group 3) alone was administered to each of 3 female rats. Each group included three rats and the powders were delivered via pulmonary insufflation. Similarly, each of Formulation 1 (Group 4), 2 (Group 5) or 3 (Group 6) containing 10.7%, 10.5% or 10.6% insulin content, respectively, was administered to each of 3 female Sprague Dawley rats (three rats per group) via pulmonary insufflation. Control rats received 1.4 mg of insulin in saline solution by pulmonary liquid instillation.

Figure 7:
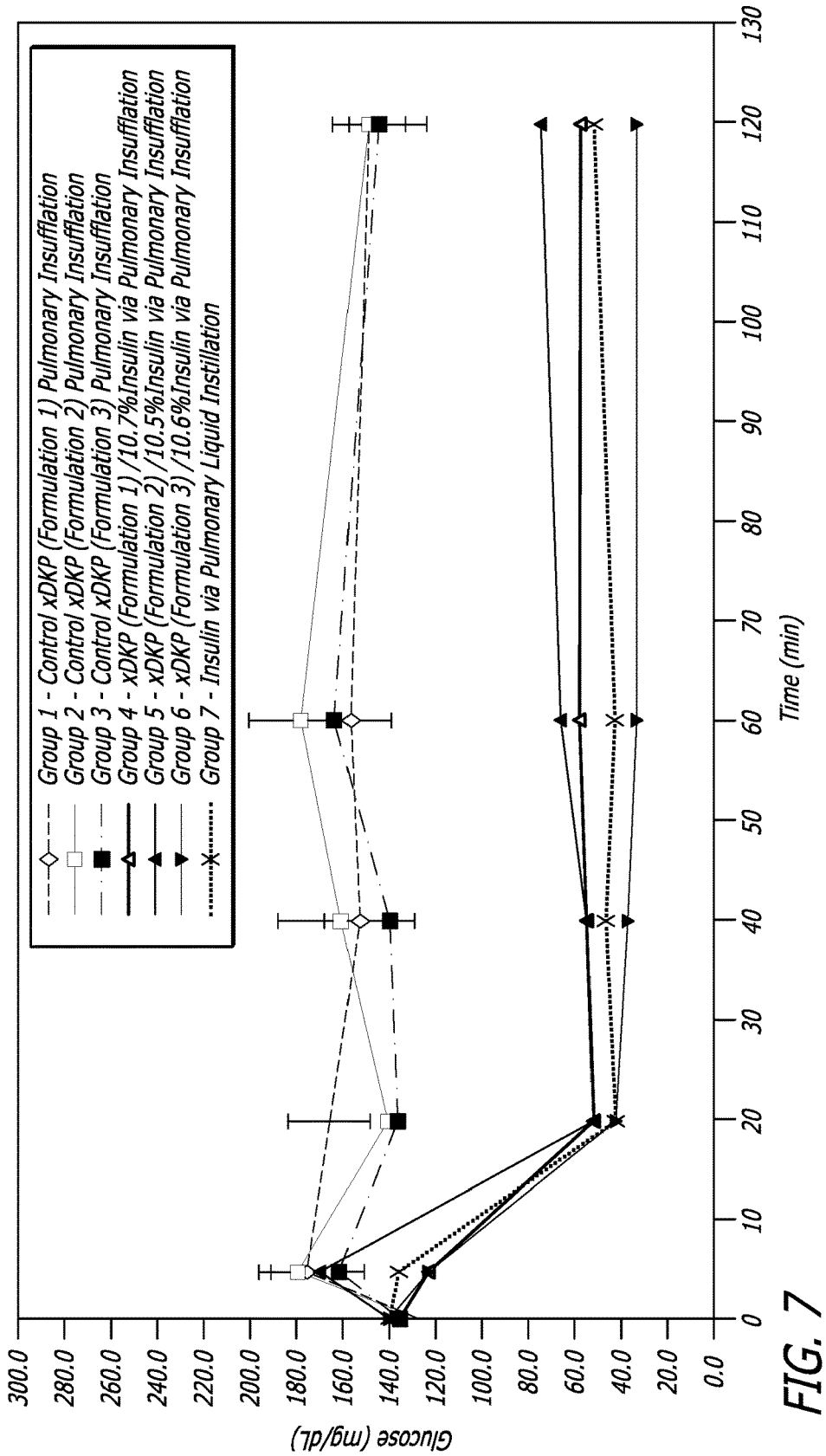
FIG. 7. depicts mean glucose levels in female rats administered a formulation of insulin (11%) with the pharmaceutically-acceptable salt of a substituted DKP analogue (E)-3-(4-(3,6-dioxopiperazin-2-yl)butylcarbamoyl)-acrylic acid compared to formulations of asymmetrical analogues, (referred to as Formulations 1 and 2), loaded with insulin at 10.7% load and 10.5% load respectively, via a single pulmonary insufflation.

Blood samples were taken on the day of dosing for each rat per group at pre-dose (0 minutes), 5, 20, 40, 60, and 120 minutes post dose. At each time point, approximately 104 of whole blood was collected from the lateral tail vein of rats in each group and analyzed for glucose levels as depicted in FIG. 7, using a monitor glucose strip. All the rats survived to scheduled sacrifice except for one. Body weights ranged from 214-250 grams.

Figure 8:
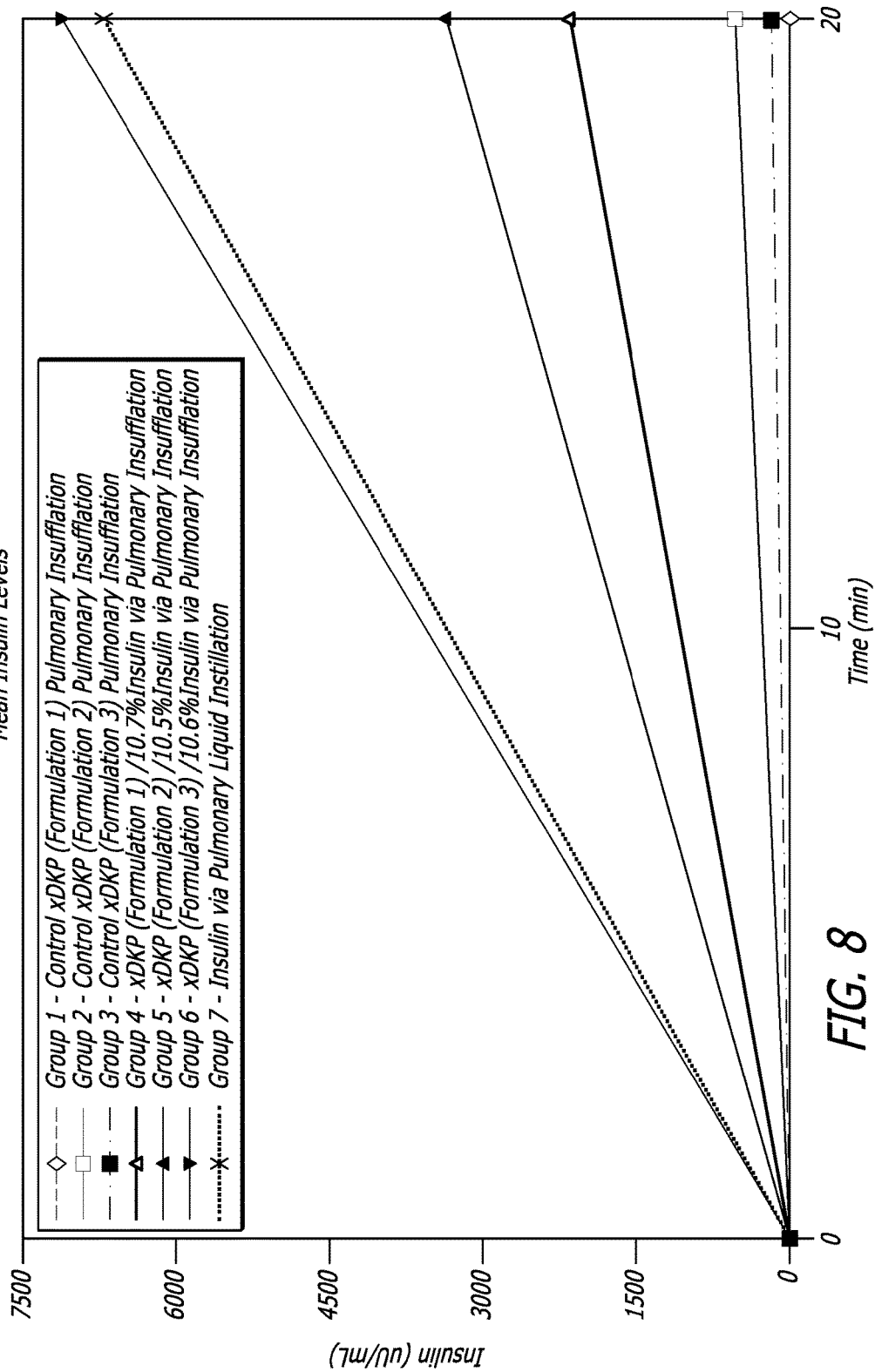
FIG. 8. depicts mean insulin levels in female rats administered a formulation of insulin (11%) with the pharmaceutically-acceptable salt of a substituted DKP analogue (E)-3-(4-(3,6-dioxopiperazin-2-yl)butylcarbamoyl)-acrylic acid compared to formulations of symmetrical analogues, (referred to as Formulations 1 and 2), loaded with insulin at 10.7% load and 10.5% load respectively, via a single pulmonary insufflation.

FIGS. 7 and 8 depict the results of these experiments. FIG. 7 illustrates the mean glucose levels measured in each of the rat groups. FIG. 7 shows that Group 6 rats had the lowest concentration of glucose in the blood, which were the rats receiving the formulation containing the substituted diketopiperazine (E)-3-(4-(3,6-dioxopiperazin-2-yl)butyl-carbamoyl)-acrylic acid (Compound 3) with a 10.6% content of insulin as depicted in FIG. 7. FIG. 7 shows that at 20 minutes after administration of the formulation, the glucose levels decreased to 40 mg/dL from the pre-dose level at 139.3 mg/dL. At 1 hour after dosing, the glucose levels decreased to 33.3 mg/dL, which was a 76% decrease from the pre-dose level at 139.3 mg/dL. At 2 hours after dosing, the blood glucose levels remained at 33.5 mg/dL.

FIG. 8 depicts the mean insulin concentrations. The control groups (Groups 1, 2 and 3) exhibited maximum concentration of insulin measured at 20 minutes after dosing. The insulin concentration in Group 2 rats were 505 µU/mL after dosing. In comparison, serum insulin levels at 20 minutes post dose in rats administered a diketopiperazine and insulin composition were as follows: Group 4 (Compound 1 and 10.7% insulin load), had a serum insulin concentration of 2136 µU/mL (IS); Group 5 (Compound 2 and 10.5% insulin load), had a serum insulin concentration of 3373 µU/mL (IS); Group 6 (Compound 3 and 10.6% insulin load), had a serum insulin concentration of 7110 µU/mL (IS); Group 7 (1.4 mg insulin in saline), had a serum insulin concentration of 6703 µU/mL (INS).

Example 6

Glucose Reduction in Rats Administered Various Substituted DKP/Insulin Powders As discussed in Example 2 above, additional substituted diketopiperazine analogs were tested to determine whether these powders have an effect on the pharmacokinetic or pharmacodynamic profiles of substituted DKP/insulin formulations. For this study, substituted diketopiperazine/insulin powders were made each containing either (E)-3-(4-(3, 6-dioxopiperazin-2-yl)butylcarbamoyl)-acrylic acid (Compound 3) and insulin; or (E)-3-(3-(3,6-dioxopiperazin-2-yl)propylcarbamoyl)-acrylic acid (Compound 4) and insulin; or (E)-3-(4-(5-isopropyl-(3,6-dioxopiperazin-2-yl)butylcarbamoyl)-acrylic acid (Compound 5) and insulin, and administered to each of 3 female Sprague Dawley rats per group via pulmonary insufflation.

The rats were divided into 5 groups as follows. Group 1 rats received a formulation containing Compound 3 with an 11.4% insulin content (Formulation 3) via pulmonary insufflation. Group 2 rats were administered a formulation Compound 3 with a 25% insulin content (Formulation 3) by pulmonary insufflation. Group 3 rats received a formulation of Compound 4 with an 11.4% insulin content (Formulation 4) by pulmonary insufflation. Group 4 rats received a formulation of Compound 5 with 11.4% insulin content by pulmonary insufflation. Group 5 rats received insulin (0.5 U/kg) via subcutaneous administration.

Figure 9:
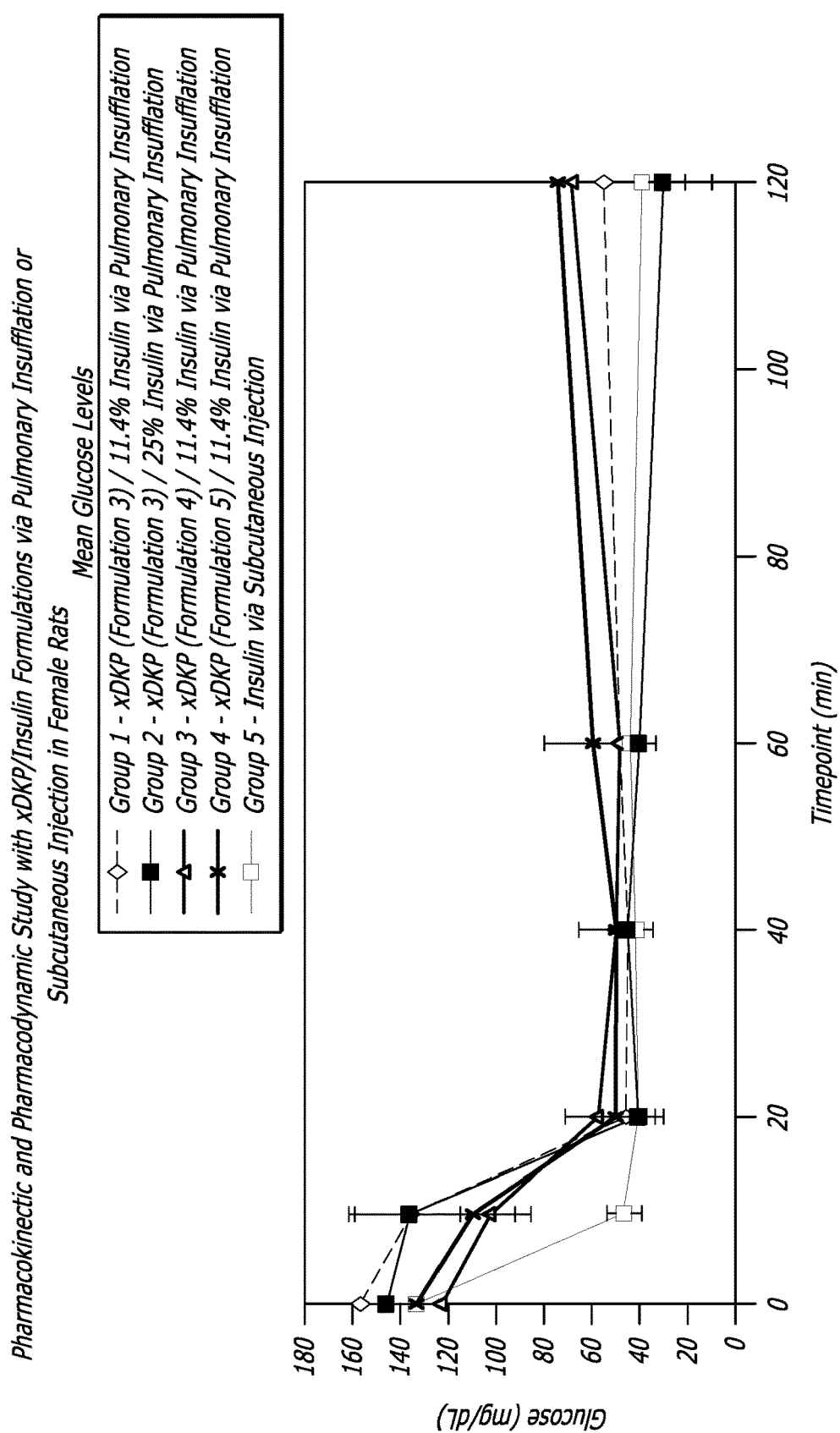
FIG. 9. depicts mean glucose levels in female rats administered various dry powder formulations containing the pharmaceutically-acceptable salt of a substituted diketopiperazine with insulin, via a single pulmonary insufflation.
Figure 10:
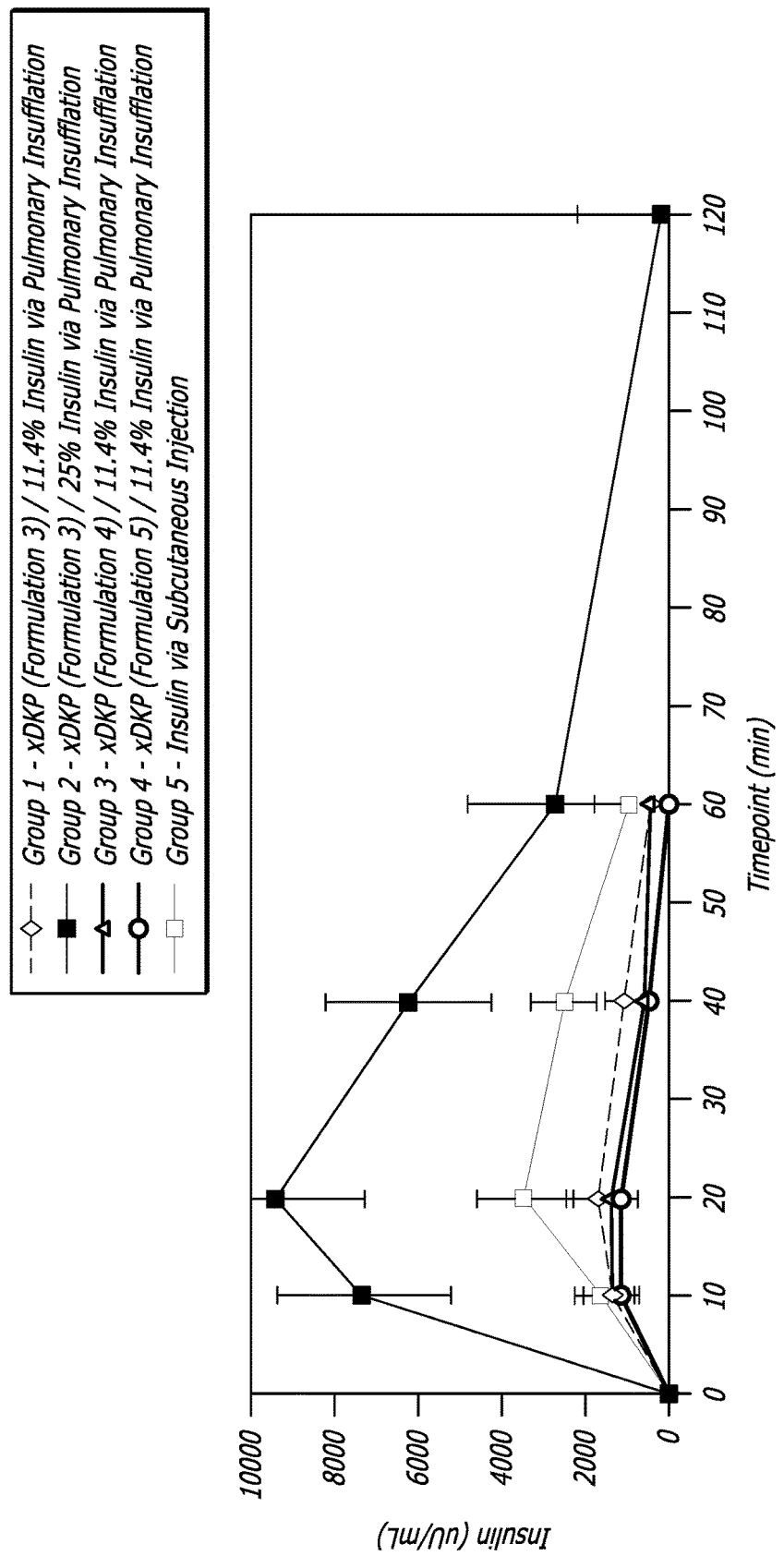
FIG. 10. depicts mean insulin levels in female rats administered various dry powder formulations containing the pharmaceutically-acceptable salt of a substituted diketopiperazine with insulin, via a single pulmonary insufflation.

Blood samples were taken on the day of dosing for each rat per group before (0 minutes) and 10, 20, 40, and 60 minutes after administration of the formulations, except for the insulin control group (group 5), for which an additional sample was collected at 120 minutes after dosing. At each time point, approximately 10 µL of whole blood was collected from the lateral tail vein of rats in each group and analyzed for measurements of insulin and glucose concentrations. The results of the study are shown in FIGS. 9 and 10. FIG. 9 shows the glucose levels as measured from blood samples using a monitor glucose strip. All the rats survived to scheduled sacrifice. Body weights were measured and ranged from 213-269 grams.

FIG. 9 illustrates the mean glucose levels measured for all groups. The lowest concentration of glucose in the blood was seen in Group 2 rats which were administered, the substituted diketopiperazine (E)-3-(4-(3,6-dioxopiperazin-2-yl)butylcarbamoyl)-acrylic acid (Formulation 3) and insulin (25%). The pre-dose level of blood glucose in Group 2 was at 145 mg/dL dropped after 20 and 40 minutes post dose, to about 40 mg/dL and decreased to 38 mg/dL after one hour, and reached 25 mg/dL at 2 hours post dose. Group 1 rats, administered approximately half the percentage of insulin as the Group 2 rats, showed the next lowest levels of glucose in blood which was about 42 mg/dL at 40 minutes post dose from as a pre-dose of 159 mg/dL. At 2 hours post dose, the glucose level measured was 49 mg/dL In the control group administered insulin only by subcutaneous injection, the lowest concentration of glucose in the blood was seen at 2 hours post dose measured at 34 mg/dL. The pre-dose level of blood glucose in this group was at 132 mg/dL. At 40 minutes post dose, the blood glucose level decreased to 43 mg/dL, and at 1 hour post dose was 42 mg/dL.

The blood glucose levels of rats administered (E)-3-(3-(3,6-dioxopiperazin-2-yl)propylcarbamoyl)-acrylic acid (Compound 4) and insulin (Formulation 4), was lowest at 60 minutes post dose at 45 mg/dL from a pre-dose level of 122 mg/dL and at 2 hours post dose at 64 mg/dL. At 40 minutes post dose, rats administered (E)-3-(4-(5-isopropyl-(3,6-dioxopiperazin-2-yl)butylcarbamoyl)-acrylic acid (Compound 5) and insulin (Formulation 5) showed the lowest glucose levels at 40 minutes post dose at 46 mg/dL from a pre-dose level of 131 mg/dL and at 2 hours post dose at 69 mg/dL.

FIG. 10 illustrates the mean insulin concentration of all groups tested. The graphs illustrate that the highest concentration of serum insulin in all groups tested was seen in Group 2 rats showing that at 20 minutes post dose the insulin concentration reached 3432 µU/mL. The data also show that at 60 minutes post dose the serum insulin level was measured at 920 µU/mL in this rats (FIG. 10). In Group 2 rats, the bioavailability of dry powder composition (E)-3-(4-(3,6-dioxopiperazin-2-yl)butylcarbamoyl)-acrylic acid (Compound 3) and insulin (25%, Formulation 3) delivered via pulmonary insufflation was 33.5% at Tmax of 20 minutes (Table 2). Group 1 rats at 20 minutes post dose showed the next highest serum insulin concentration at 1605 µU/mL and the bioavailability of dry powder composition (E)-3-(4-(3,6-dioxopiperazin-2-yl)butylcarbamoyl)-acrylic acid (Compound 3) and insulin (11.4%, Formulation 3) delivered via pulmonary insufflation was 18% at Tmax of 20 minutes. The highest serum insulin concentration for Groups 3 and 4 was at 1393 µU/mL and 1176 µU/mL, respectively, at 10 minutes post dose. The bioavailability of (E)-3-(3-(3,6-dioxopiperazin-2-yl)butylcarbamoyl)-acrylic acid (Compound 4) and insulin (11.4%, Formulation 4) delivered via pulmonary insufflation to Group 3 rats was 15% at Tmax of 10 minutes; and the bioavailability of (E)-3-(4-(5-isopropyl-(3,6-dioxopiperazin-2-yl)butylcarbamoyl)-acrylic acid (Compound 5) and insulin (11.4%; Formulation 5) delivered via pulmonary insufflation to Group 4 rats was 10% at Tmax of 10 minutes. In the control group wherein insulin was administered by subcutaneous injection, the serum insulin concentration was measured at 9360 µU/mL at 20 minutes post dose.

TABLE 2

Relative Bioavailability of Substituted Diketopiperazine Powders

| Group | Cmax (U/mL) | Tmax (min) | AUC (all) | T½ (min) | BIOAVAILABILITY (%) |
|---|---|---|---|---|---|
| 1 (Formulation 3/ 0.5 mg of 11.4%) | 1605.01 | 20 | 60867.63 | 18.72 | 17.86 |
| 2 (Formulation 3/ 0.25 mg of 25%) | 3431.71 | 20 | 125104.89 | 21.06 | 33.49 |
| 3 (Formulation 4/ 0.5 mg of 11.4%) | 1392.5 | 10 | 49520.53 | 20.02 | 14.53 |
| 4 (Formulation 5/ 0.5 mg of 11.4%) | 1175.58 | 10 | 33361.02 | 20.17 | 9.79 |
| 5 (SC-Insulin Control) | 9359.6 | 20 | 442689.37 | 9.18 | 100 |

Based on the results from this study, the dry powder composition of (E)-3-(4-(3,6-dioxopiperazin-2-yl)butylcarbamoyl)-acrylic acid (Compound 3) and insulin (25% or 11.4%, Formulation 3) showed the highest levels of insulin in the serum and showed the lowest concentration of glucose in the blood compared to other novel substituted diketopiperazine and insulin compositions tested A 2-fold bioavailability was also observed for the formulation containing Compound 3 when the insulin load was increased from 11.4% to 25%. The data from these experiments show that all the formulations lowered serum glucose levels as well as delivered insulin effectively into the pulmonary circulation.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the embodiments (especially in the context of the following claims) are to be construed to cover both the singular and the plural, unless otherwise indicated herein or clearly contradicted by context. As used in this specification and claim(s), the term "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the embodiment and does not pose a limitation on the scope of the disclosure otherwise claimed. No language in the specification should be construed as indicating any non-claimed element essential to the practice of the disclosure.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments described herein, include the best mode known to the inventors for carrying out the embodiments disclosed. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments disclosed herein are illustrative of the principles of the disclosure. Other modifications that may be employed are within the scope described. Thus, by way of example, but not of limitation, alternative configurations of the disclosure may be utilized in accordance with the teachings herein. Accordingly, the disclosure is not limited to that precisely as shown and described.

What is claimed:

1. A dry powder composition comprising an active agent and a diketopiperazine of the formula:

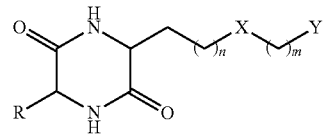

wherein R is H or an alkyl group of 1-10 carbons; n or m=0-20; X is an amide, ester, sulfone, sulfoxide, amine, or ketone; and Y is an amide, acid, hydroxyl, phenol, phosphonic acid, or thiol.

2. The dry powder composition of claim 1 wherein R is hydrogen, n=3, m is C=C, X is —NHC(O)—, and Y is COOH.

3. The dry powder composition of claim 1 wherein R is hydrogen, n=2, m is C=C, X is —NHC(O)—, and Y is COOH.

4. The dry powder composition of claim 1 wherein R is an isopropyl, n=3, m is C=C, X is —NHC(O)—, and Y is COOH.

5. The dry powder composition of claim 1 wherein the active agent is a peptide, protein, polypeptide, small molecule, or nucleic acid molecule.

6. The dry powder composition of claim 5, wherein the active agent is selected from the group consisting of insulin, glucagon, glucagon like peptide 1 (GLP-1), calcitonin, parathyroid hormone 1-34, bioactive fragment of parathyroid hormone, octreotide, leuprolide, and RSV peptide, granulocyte colony stimulating factor (GM-CSF), peptide YY, oxyntomodulin, felbamate, cannabinoid antagonists, cannabinoid agonists, muscurinic antagonists, muscarinic agonists, heparin, low molecular weight heparin, cromolyn, sildenafil, vardenafil, tadalafil, growth hormone, AZT, DDI, lamotrigine, chorionic gonadotropin releasing factor, luteinizing release hormone, beta-galactosidase, exendins 1-4, ghrelin, tryptin, and analogs and fragments thereof.

7. The dry powder composition of claim 6, wherein the active agent is insulin or an insulin analog.

8. The dry powder of claim 6, wherein the active agent is parathyroid hormone 1-34 or a bioactive fragment thereof.

9. The dry powder of claim 6, wherein the active agent is leuprolide.

10. The dry powder of claim 6, wherein the active agent is GLP-1 or an analog thereof.

11. The dry powder of claim 6, wherein the active agent is granulocyte macrophage colony stimulating factor.

12. The dry powder of claim 6, wherein the active agent is a cannabinoid agonist.

13. The dry powder of claim 6, wherein the active agent is a cannabinoid antagonist.

14. The dry powder of claim 6, wherein the active agent is sildenafil.

15. A method of increasing plasma level of an active agent in a patient in need thereof, comprising administering to the patient by inhalation the dry powder composition of claim 1.

16. A dry powder composition comprising a cannabinoid and a diketopiperazine of the formula:

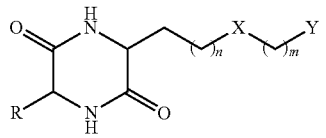

wherein R is H or an alkyl group of 1-10 carbons; n or m=0-20; X is an amide, ester, sulfone, sulfoxide, amine, or ketone; and Y is an amide, acid, hydroxyl, phenol, phosphonic acid, or thiol.

* * * * *